(12) United States Patent
Kim et al.

(10) Patent No.: US 11,365,249 B2
(45) Date of Patent: Jun. 21, 2022

(54) BINDING MOLECULE SPECIFIC FOR LRIG-1 PROTEIN AND USE THEREOF

(71) Applicant: GOOD T CELLS, INC., Seoul (KR)

(72) Inventors: Jung Ho Kim, Seoul (KR); Beom Seok Kim, Seoul (KR)

(73) Assignee: GOOD T CELLS, INC., Seoul (KR)

(*) Notice: Subject to any disclaimer, the term of this patent is extended or adjusted under 35 U.S.C. 154(b) by 232 days.

(21) Appl. No.: 16/606,138

(22) PCT Filed: Apr. 18, 2018

(86) PCT No.: PCT/KR2018/004524
§ 371 (c)(1),
(2) Date: Oct. 17, 2019

(87) PCT Pub. No.: WO2018/194381
PCT Pub. Date: Oct. 25, 2018

(65) Prior Publication Data
US 2020/0048343 A1 Feb. 13, 2020

(30) Foreign Application Priority Data

Apr. 18, 2017 (KR) .................. 10-2017-0049854

(51) Int. Cl.
| | | |
|---|---|---|
| *C07K 16/28* | (2006.01) | |
| *A61P 35/00* | (2006.01) | |
| *A61K 39/00* | (2006.01) | |
| *A61P 37/06* | (2006.01) | |

(52) U.S. Cl.
CPC .............. *C07K 16/28* (2013.01); *A61P 35/00* (2018.01); *A61P 37/06* (2018.01); *A61K 2039/505* (2013.01); *C07K 2317/21* (2013.01); *C07K 2317/52* (2013.01); *C07K 2317/565* (2013.01); *C07K 2317/76* (2013.01)

(58) Field of Classification Search
CPC .............. C07K 16/28; C07K 2317/565; C07K 2317/76; A61K 2039/505; A61P 35/00
See application file for complete search history.

(56) References Cited

U.S. PATENT DOCUMENTS

| 9,213,032 B2 | 12/2015 | Lee et al. |
|---|---|---|
| 9,556,275 B2 | 1/2017 | Jeong et al. |
| 2015/0239964 A1 | 8/2015 | Lee |
| 2017/0081410 A1 | 3/2017 | Crawley et al. |
| 2020/0048343 A1 | 2/2020 | Kim et al. |
| 2020/0131261 A1 | 4/2020 | Kim et al. |

FOREIGN PATENT DOCUMENTS

| KR | 10-2012-0085593 A | 8/2012 |
|---|---|---|
| KR | 10-2014-0013873 A | 2/2014 |
| KR | 10-2014-0120572 A | 10/2014 |
| KR | 10-2086656 B1 | 3/2020 |
| KR | 10-2086649 B1 | 4/2020 |
| WO | 2015/187359 A1 | 12/2015 |

OTHER PUBLICATIONS

Paul, William, Fundamental Immunology, 3rd Edition, Raven Press, New York, 1993, pp. 292-295.*
Vajdos et al., Comprehensive functional maps of the antigen-binding site of an anti-ErbB2 antibody obtained with shotgun scanning mutagenesis. J. Mol. Biol. 320:415-428, 2002.*
Rudikoff et al., Single amino acid substitution altering antigen-binding specificity. Proc. Natl. Acad. Sci. USA 79:1979-1983, 1982.*
Brown et al., Tolerance of single, but not multiple, amino acid replacements in antibody VH CDR 2: a means of minimizing B cell wastage from somatic hypermutation? J. Immunology 156: 3285-3291, 1996.*
Zhang et al., Clinicopathological and prognostic significance of leucine-rich repeats and immunoglobulin-like domains protein 1 (LRIG1) in malignant tumors: A meta-analysis. Journal Cancer 9 (16):2895-2909, 2018.*
Lindquist et al. LRIGand cancer prognosis. Acta Oncologica 53 (9): 1135-1142, 2014.*
French, How to make bispecific antibodies, Methods Mol. Med., 40:333-339 (2000).
GenBank Accession No. AAN86780.1; Immunoglobulin Heavy Chain, Partial [Mus musculus], Jul. 24, 2016.
GenBank Accession No. CAC20700.1: Immunoglobulin Light Chain Constant Region Kappa, Partial [Mus musculus], Jun. 11, 2015.
Houshmand et al., Targeting tumor cells, Curr. Opin. Cell Biol., 15(5):640-644 (2003).
Jackson et al., In vitro antibody maturation. Improvement of a high affinity, neutralizing antibody against IL-1 beta, J. Immunol., 154(7):3310-3359 (1995).
Nilsson et al., LRIG1 protein in human cells and tissues, Cell and Tissue Research, 312:65-71 (2003.).
Pearson, Using the FASTA program to search protein and DNA sequence databases, Meth. Mol. Biol., 24:307-331(1994).
Schier et al., Identification of functional and structural amino-acid residues by parsimonious mutagenesis, Gene., 169(2):147-155 (1995).
Suzuki et al., Targeted disruption of LIG-1 gene results in psoriasiform epidermal hyperplasia, FEBS Letters, 521(1-3):67-71 (2002).
Tanemura et al., LRIG-1 Provides a Novel Prognostic Predictor in Squamous Cell Carcinoma of the Skin: Immunohistochemical Analysis for 38 Cases, Dermatologic Surgery, 31(4):423-430 (2005).

* cited by examiner

*Primary Examiner* — Ruixiang Li
(74) *Attorney, Agent, or Firm* — Marshall, Gerstein & Borun LLP

(57) ABSTRACT

The present invention relates to a binding molecule capable of specifically binding to Lrig-1 protein, which is on the surface of regulatory T cells. The binding molecule provided in the present invention can suppress the function of regulatory T cells to effectively prevent, ameliorate, or treat cancer, particularly solid tumor. The binding molecule has advantages of more effectively targeting the Lrig-1 protein as compared with antibodies against Lrig-1 which are previously commercially available, and also possessing very good binding capacity thereto.

15 Claims, 13 Drawing Sheets

Specification includes a Sequence Listing.

[FIG. 1]
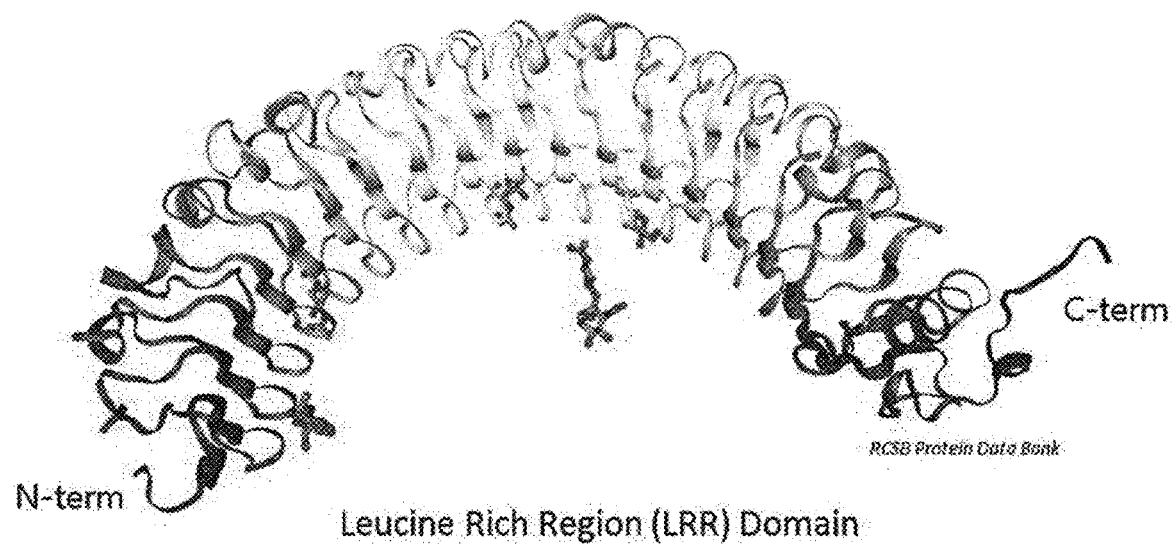
Leucine Rich Region (LRR) Domain
[FIG. 2]
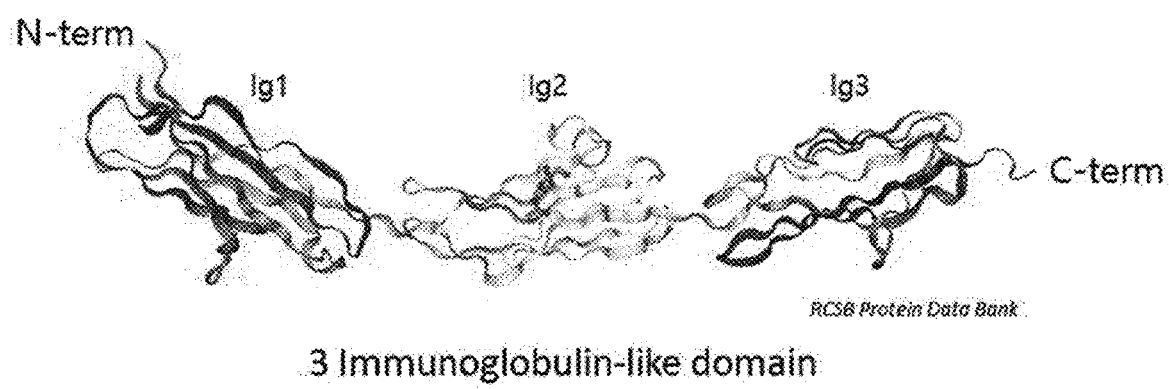
3 Immunoglobulin-like domain

| No. | Chain | Start | End | Peptide | Number of Residues | Score |
|---|---|---|---|---|---|---|
| 1 | A | 9 | 56 | GDSLDGGGRGLAALPGDLRSSTRSLNLSYNKLSEDPAGFEDLPVLGE | 48 | 0.86 |
| 2 | A | 399 | 455 | SDSFLCDCCLKWLPRWLGRMLDAFVTATCAHFESLKGCDSFSVPRESFVCDDFLKA | 57 | 0.853 |
| 3 | A | 60 | 66 | NMNELTA | 7 | 0.814 |
| 4 | A | 376 | 393 | NARGVCFDAFVRQMNLK | 18 | 0.588 |
| 5 | A | 85 | 89 | MKRS | 5 | 0.561 |
| 6 | A | 232 | 237 | VEYNSG | 6 | 0.841 |
| 7 | A | 256 | 261 | ARHPK | 6 | 0.538 |
| 8 | A | 109 | 117 | NMTEVRNT | 9 | 0.52 |
| 9 | A | 183 | 196 | RLESLTPQSLNS | 14 | 0.52 |
| 10 | A | 207 | 220 | BKLTDGAFWGLSK | 14 | 0.514 |
| 11 | A | 158 | 170 | NPATQLPVPARL | 13 | 0.501 |
| 12 | A | 96 | 101 | KAYLSL | 6 | 0.5 |
| 13 | A | 631 | 659 | KKDMEVLTWLDMENFVHVHAVNEYT | 25 | 0.82 |
| 14 | A | 517 | 527 | SAASSSSSPVT | 11 | 0.817 |
| 15 | A | 727 | 744 | FKGDRPLSLTERHHLTPD | 18 | 0.791 |
| 16 | A | 777 | 786 | QLSVLLENLY | 10 | 0.772 |
| 17 | A | 494 | 501 | KPQITDP | 8 | 0.732 |
| 18 | A | 697 | 711 | VPLERVVSVGETVA | 15 | 0.721 |
| 19 | A | 649 | 658 | HVNPDDDVFF | 10 | 0.69 |
| 20 | A | 579 | 590 | ITNHFGSTYSHK | 12 | 0.679 |
| 21 | A | 746 | 760 | QLLWDNVAEDAGR | 15 | 0.669 |
| 22 | A | 562 | 570 | HLRQVTFG | 9 | 0.564 |

[FIG. 3]

| No. | Peptide | Number of Residue | Score |
|---|---|---|---|
| 1 | C1, P2, S3, R4, C5, T6, C7, S8, G9, D10, S11, L12, D13, C14, G15, G16, R17, G18, L19, A20, A21, L22, P23, G24, D25, L26, P27, S28, S29, T30, R31, S32, L33, N34, L35, S36, Y37, N38, K39, L40, S41, E42, K43, D44, P45, A46, G47, F48, E49, D50, L51, P52, N53, L54, C55, E56, L59, N60, N61, N62, E63, L64, T65, A66, P68, S69, L70, G71, A72, A73, S74, S75, H78, V79, H84, N85, K86, R87, R82, S89, K90, K95, A97, Y98, L99, S100, L101, P103, H121, G122, P123, P124 | 91 | 0.747 |
| 2 | N109, M110, I111, T112, E113, R115, N116, T117, N132, R134, I135, G138, T137, E139, L140, G141, A142, N158, R159, H160, T161, Q162, L183, P164, V165, R166, A167, K169, L170, P171, R182, L183, L185, E187, G188, L193, T190, Q192, Q193, L194, N195, S198, S207, S209, K209, T211, D212, A214, F215, W216, G217, L218, S219, K220, S230, L231, V232, E233, V234, N235, S236, G237, Y240, G241, L242, T243, A244, A256, R257, S260, K261, S264, F265, G267, E294, E285, S288, L287, A298, E289, L290, S291, A307, E308, G309, K312, G313, R315, S318, S335, G336, G338, S339, G340, L341, C342, I343, I354, A355, K358, G364, L385, E366, G367, E269, N370, A377, I378, R379, S380, V381, C382, F383, D384, A385, V387, K388, M389, N391, L392, K393, S399, D400, S401, F402, L403, C404, D405, C406, Q407, L408, K409, W410, L411, P412, P413, W414, L415, K416, G417, R418, L420, Q421, A422, F423, V424, T425, A426, T427, C428, A429, H430, P431, E432, S433, L434, K435, G436, K438, S437, S439, H39, F440, S441, V442, P443, P444, E445, S446, S448, F447, V448, C449, Q450, D451, R452, L453, K454, A455 | 178 | 0.636 |
| 1 | N784, L785, Y788 | 3 | 0.677 |
| 2 | K494, P495, Q498, H97, K98, T499, Q500, P501, S517, A518, L519, S520, S521, S522, S523, S524, P525, M526, T527, E543, N544, F546, V546, H547, V548, H549, V555, M556, E557, Y558, T559, E79, T580, M581, H582, F583, G584, S585, T586, Y587, S638, H589 | 42 | 0.789 |
| 3 | V697, R598, L699, E700, D701, R702, V703, V704, S705, V706, G707, E708, T709, V710, A711, F727, K729, G729, D730, R731, P732, L733, S734, L735, T736, E737, R738, H739, H740, L741, T742, P742, D744, N745, L747, V748, V750, Q751, N752, V753, V754, A755, E756, D757, A758, R760, Q777, L778, S779, V780, L781, L782, E783 | 63 | 0.739 |
| 4 | D511, K531, K532, D533, N534, E536, V536, L537, T538, N539, A540, D541, M542, H583, R565 | 15 | 0.689 |
| 5 | T614, M615, H649, V653, M651, P652, D653, D654, D655, V656, F656, T660 | 12 | 0.669 |
| 6 | V608, C609, K510, Q666, V667, T668, F669, G670 | 8 | 0.639 |

[FIG. 4]

[FIG. 5]
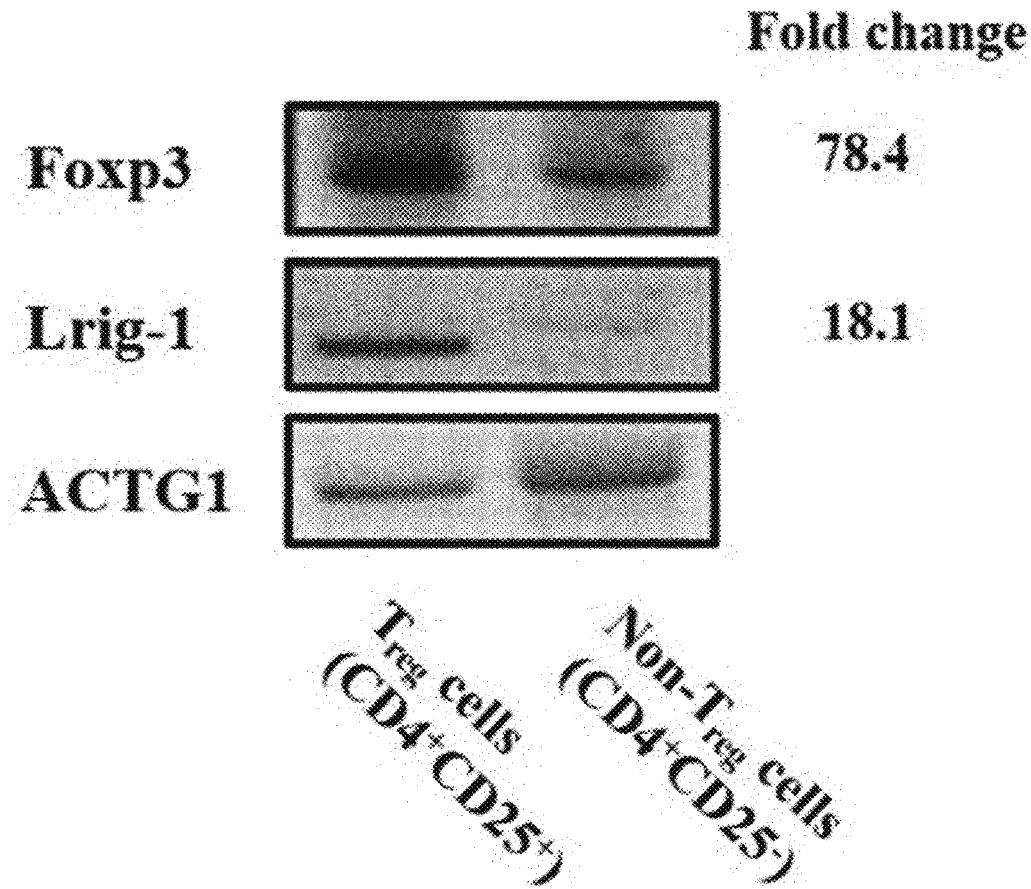

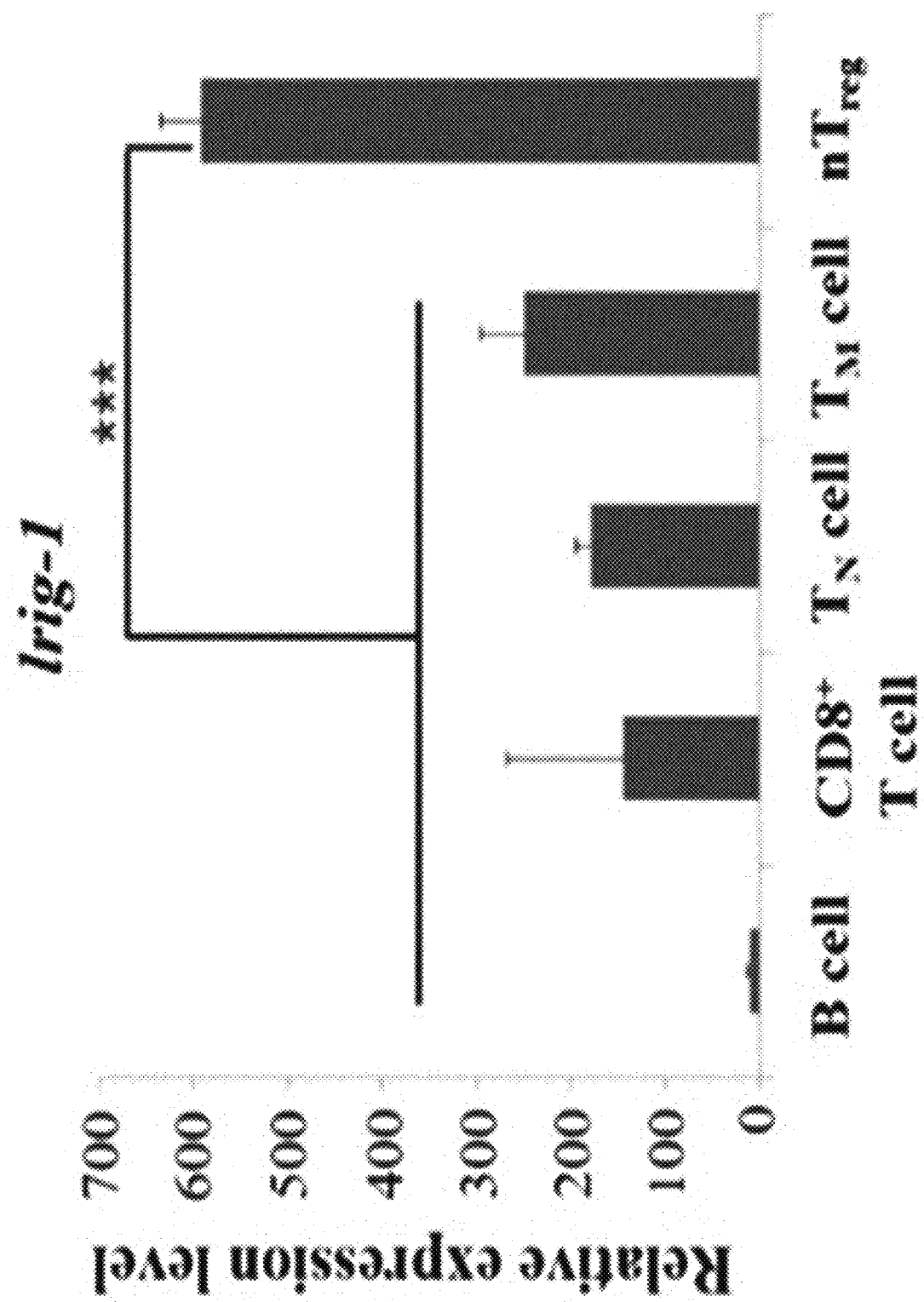
[FIG. 6]

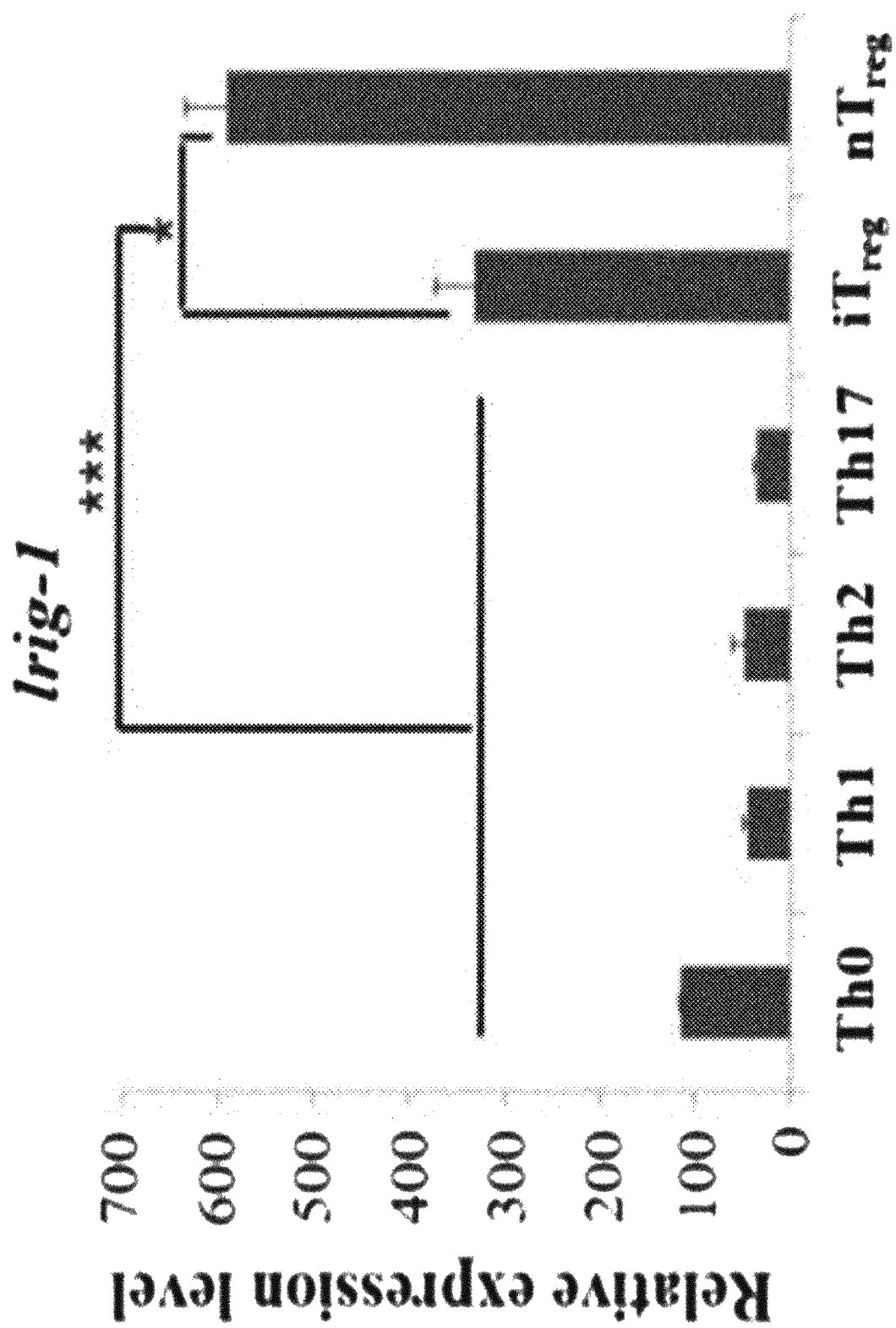
[FIG. 7]

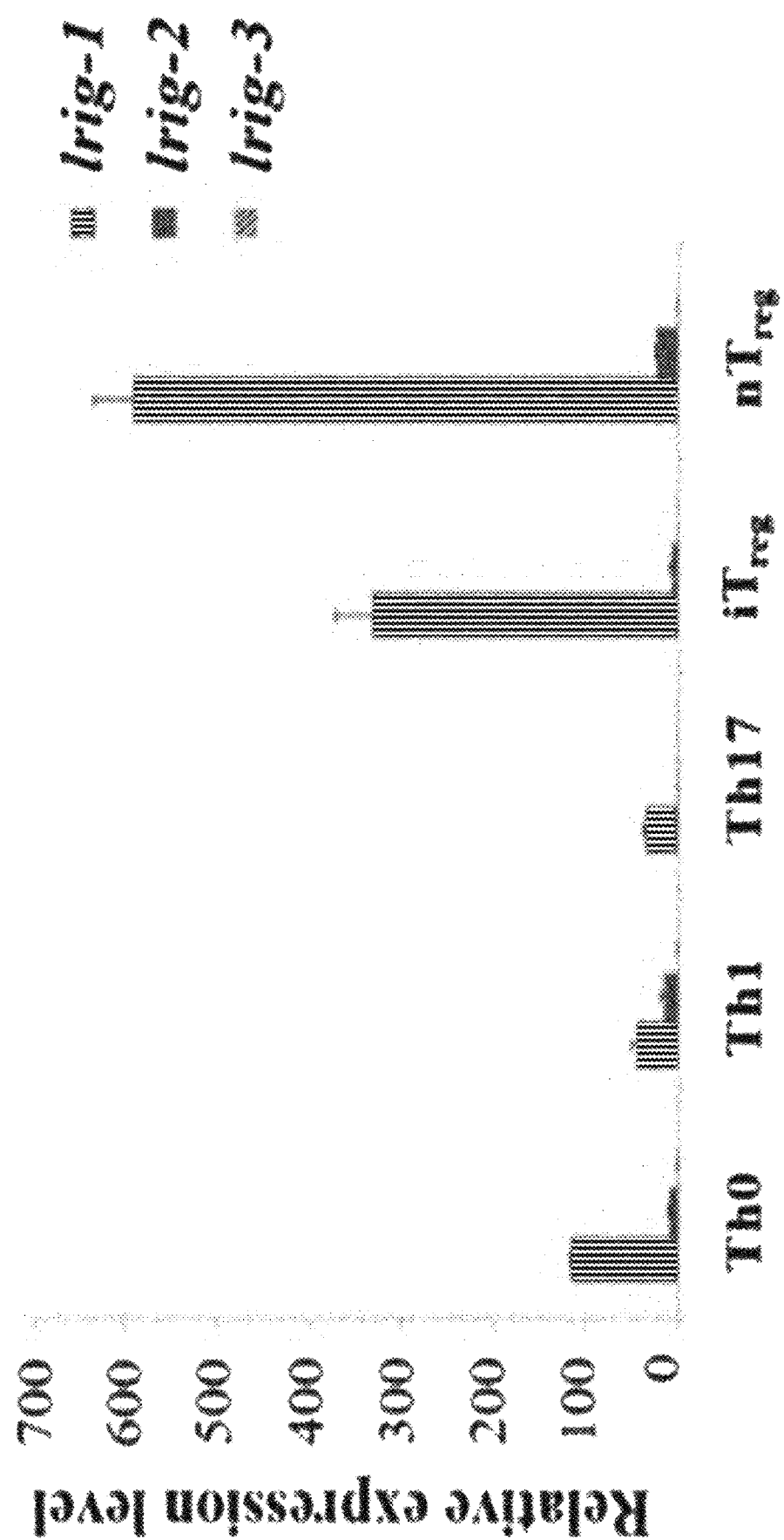
[FIG. 8]

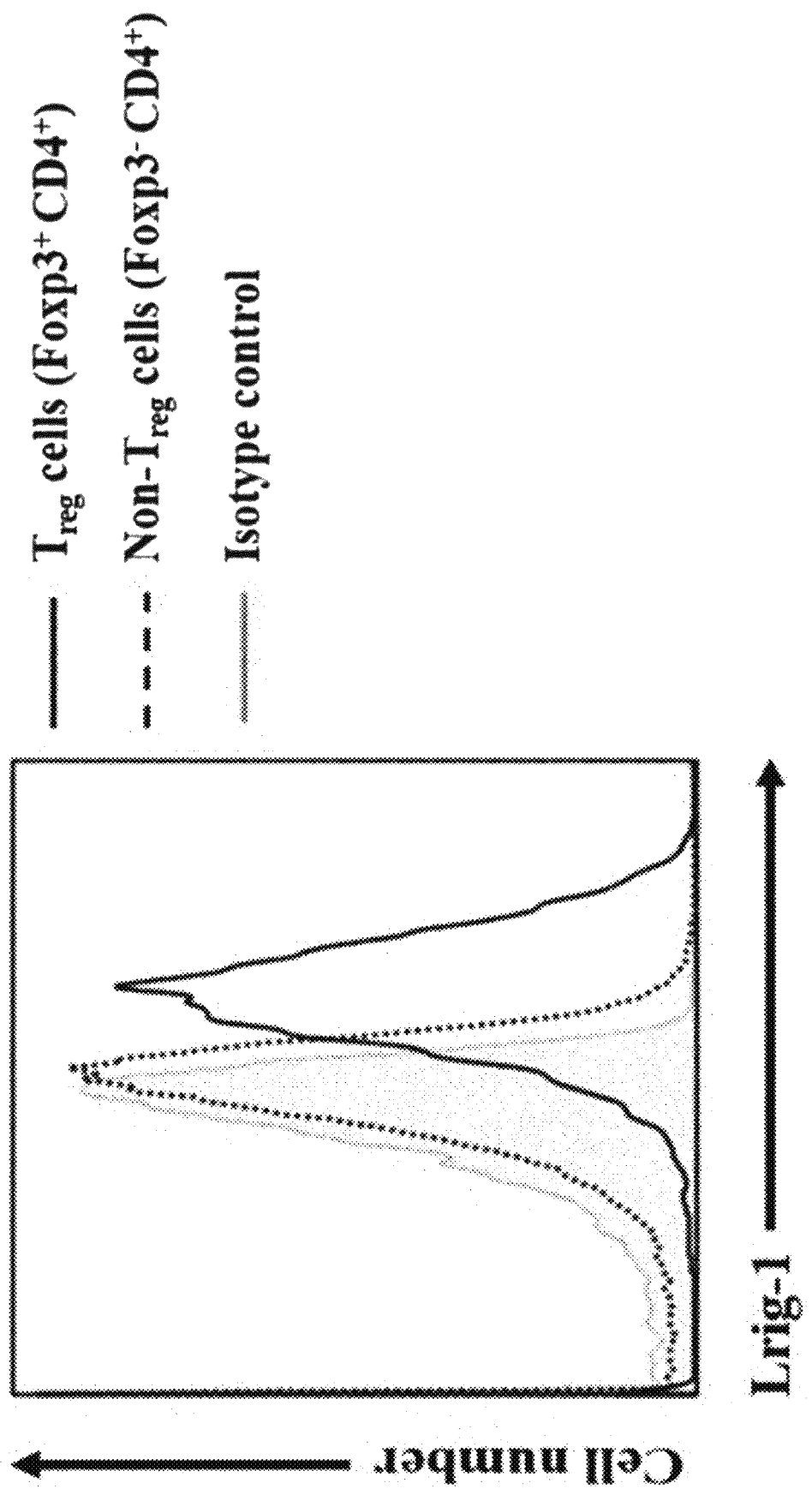
[FIG. 9]

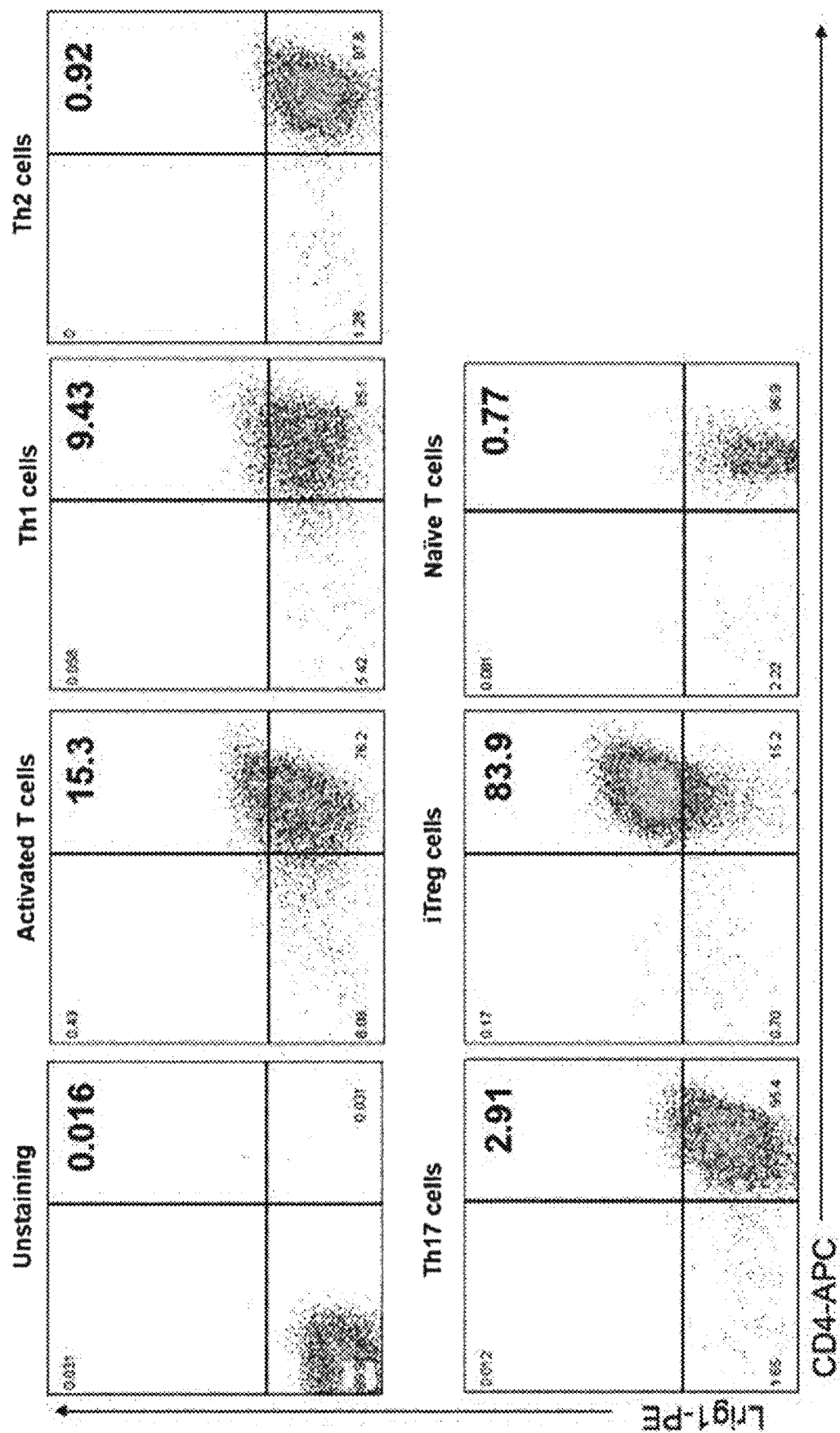
[FIG. 10]

[FIG. 11]
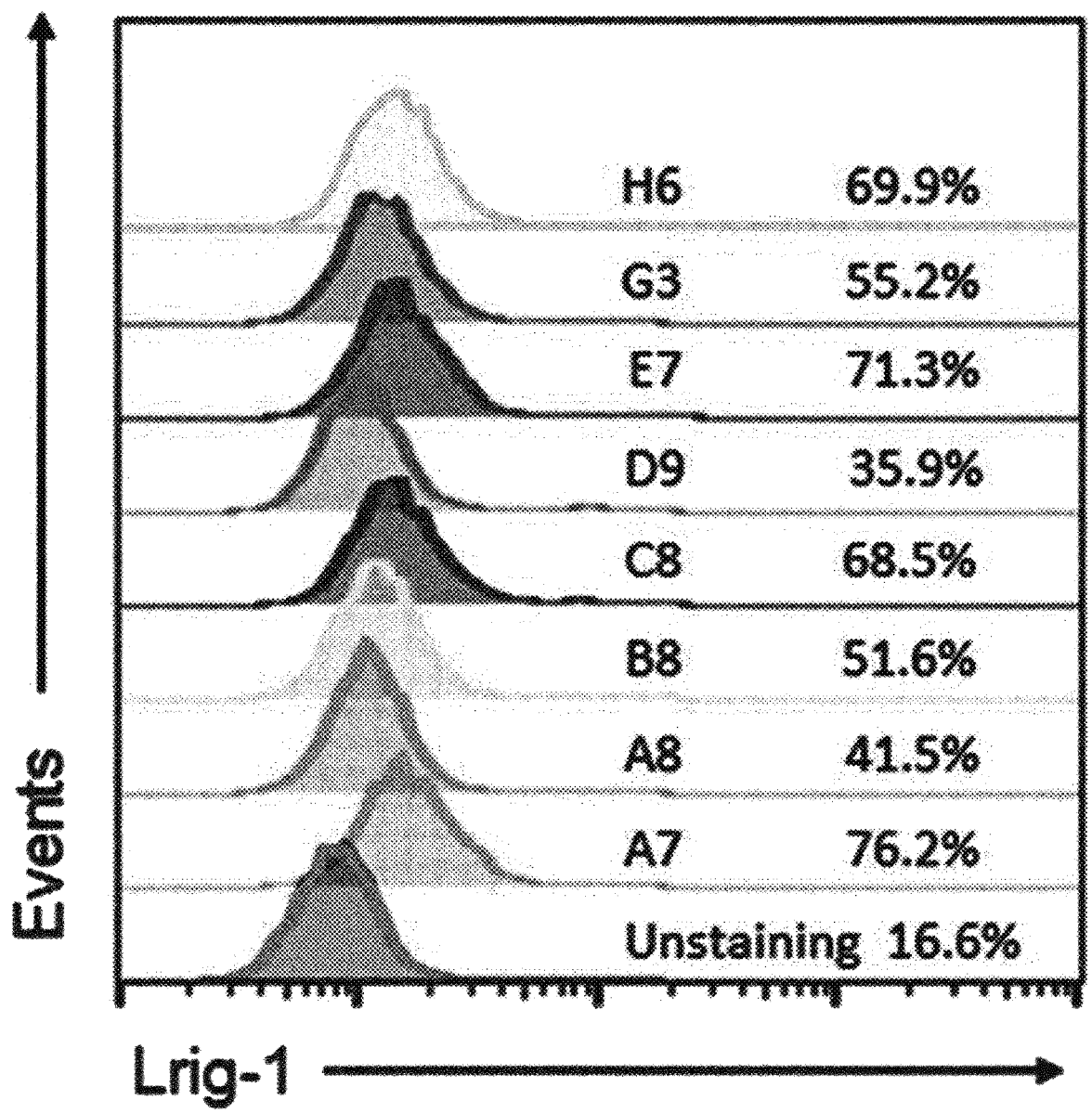

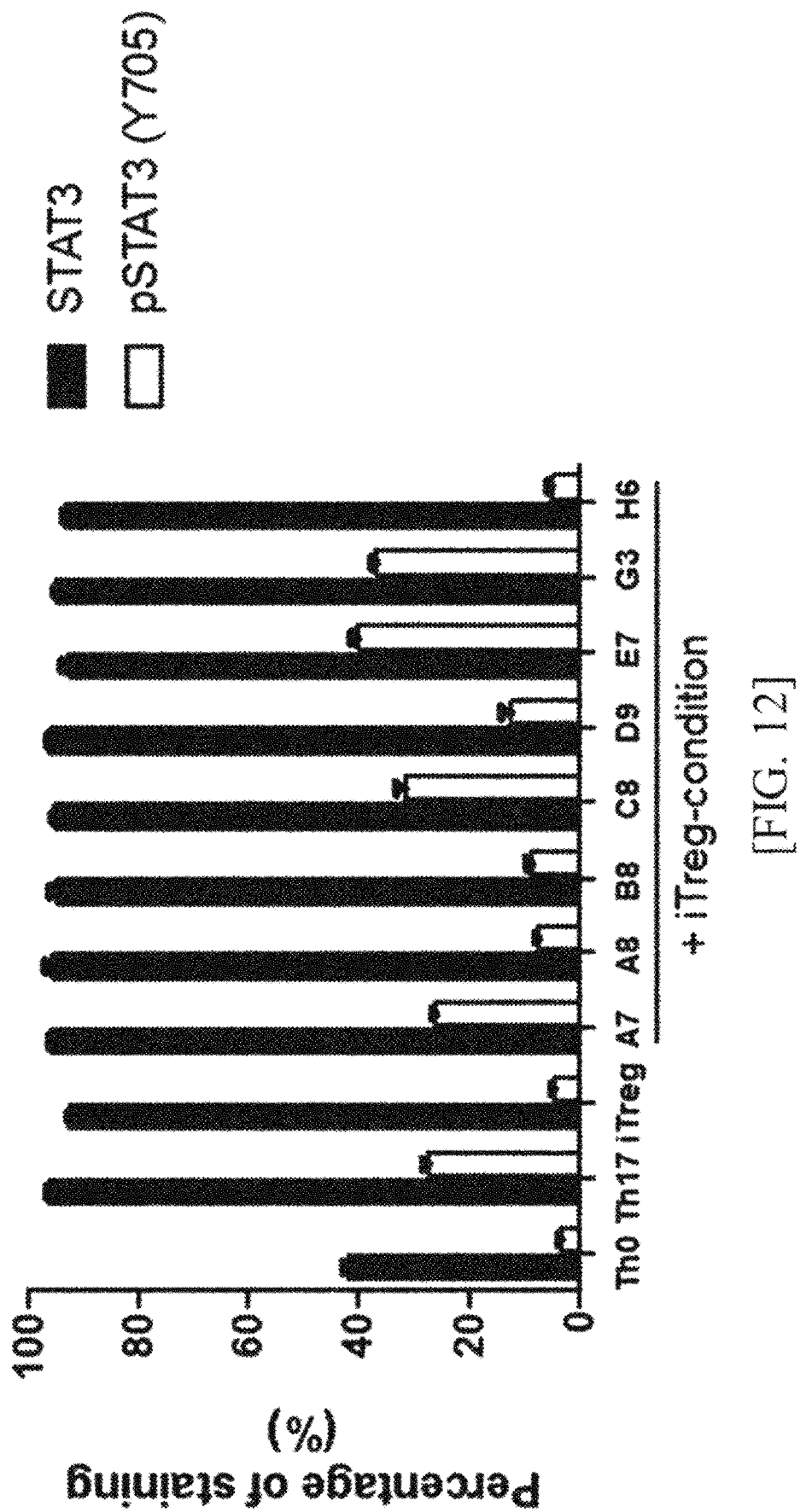
[FIG. 12]

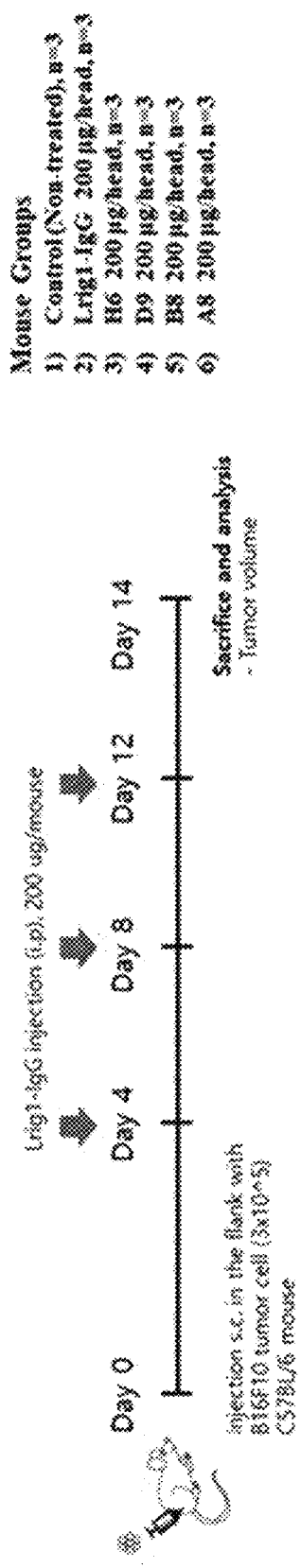
[FIG. 13]

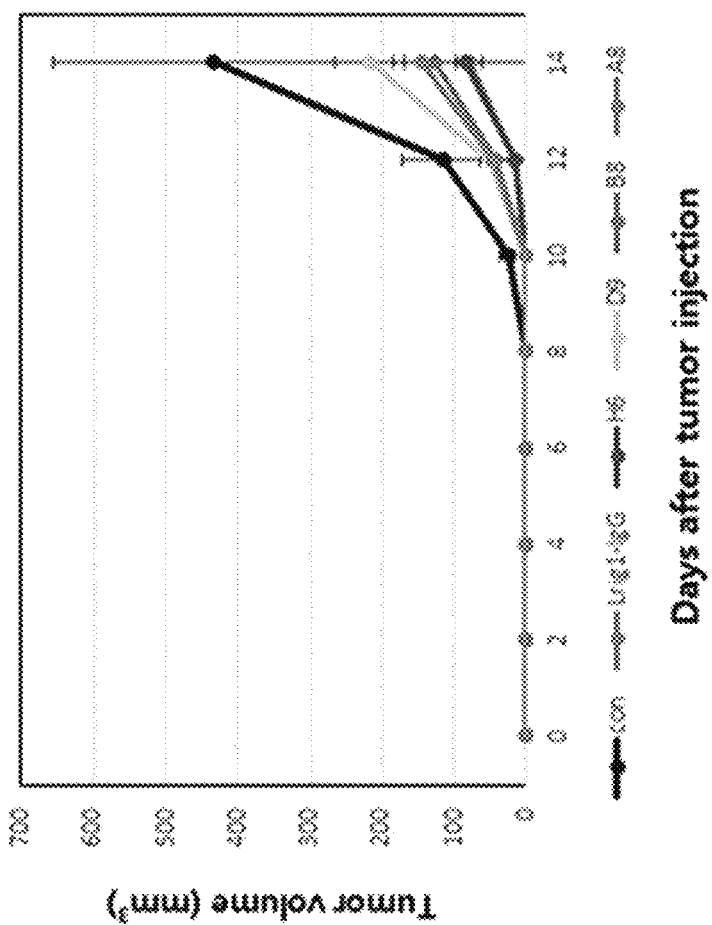
[FIG. 14]

BINDING MOLECULE SPECIFIC FOR LRIG-1 PROTEIN AND USE THEREOF

CROSS REFERENCE TO RELATED APPLICATIONS

This application is a U.S. National Stage of International Application No. PCT/KR2018/004524, filed Apr. 18, 2018, which claims the benefit of Korean Patent Application No. 10-2017-0049854, filed Apr. 18, 2017, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "54881_Seqlisting.txt." The Sequence Listing was created on Oct. 17, 2019, and is 78,941 bytes in size. The subject matter of the Sequence Listing is incorporated herein in its entirety by reference.

TECHNICAL FIELD

The present invention relates to a binding molecule capable of specifically binding to leucine-rich and immunoglobulin-like domains 1 (Lrig-1) protein, which is a protein present on the surface of regulatory T cells (Treg cells), and a use thereof.

BACKGROUND ART

Cancer cells are widely thought to express immunogenic antigens that can induce an effective immune response against tumor formation. In addition, the tumor microenvironment is rich in components that can trigger TLR signal transduction to activate anti-tumor responses (see Standiford T J, Keshamouni V G (2012) Breaking the tolerance for tumor: Targeting negative regulators of TLR signaling. Oncoimmunology 1: 340-345). This means that at the early stages of the disease, cancer cells may have opportunities to be recognized and rejected by the immune system which exerts both host-protective and tumor-modeling actions against developing tumors. Nonetheless, cancer cells also have numerous negative regulatory mechanisms for evading immune surveillance, such as downregulation of MHC molecules or antigen processing and presentation machinery, which increase secretion of suppressive cytokines and express suppressive molecules so that immune tolerance to cancer cells is induced. Thus, cancer patients are often considered to have poor immunity. Accordingly, there is still a need to develop agents or therapies for reversal of cancer-related immunosuppression.

Meanwhile, antibody-based cancer therapies have characteristics of potentially high specificity and low side effects, as compared with conventional drugs. This is because antibodies allow precise differentiation between normal and neoplastic cells and their mode of action depends on less toxic immunological antitumor mechanisms such as influx of cytotoxic immune cells and complementary activation.

Targets for antibody-based therapies need to have particular properties which form the basis for proper differentiation between normal and neoplastic cells. Needless to say, in developing effective and safe antibody therapies, a target which is exclusively restricted only to tumor cells or which is not detected at all on normal tissue would be ideal. In another aspect, high overexpression may be the basis for the therapeutic window, and low side effects exemplified by human epidermal growth factor receptor type 2 (HER-2) as a result of gene amplification make HER-2 an excellent target for the antibody trastuzumab (Herceptin).

Other targets for antibodies which have already been approved in tumor therapies or are in clinical development have distinct properties which are not based on numerical overexpression of target molecules on tumor cells. In a case of antibodies against proteoglycan MUC-1, a peptide repeat epitope in the backbone of the target is underglycosylated in tumor cells and thus altered to its normal counterpart. In a case of antibodies against CD20 (rituximab), CD52 (Campath-1H), and CD22 (epratuzumab), antibody targets have comparable expression levels on tumor cells and normal lymphocytes. In this regard, elimination of normal cells by the antibodies is tolerable since target-negative stem cells restore the normal lymphocyte repertoire. Other examples of different accessibility of antibody targets are carcinoembryonic antigen (CEA) and carboanhydrase IX (CA9). Both of these antigens are expressed on normal epithelia of colon and kidney, respectively. However, radioactively labeled imaging antibodies do distinguish well between tumor and normal tissue, and thus cytotoxic antibodies are well tolerated. This is probably because expression of CA9 and CEA is restricted only to the lumen side of normal epithelial tissue to which IgG antibodies do not have access. Antigen epithelial cell adhesion molecule (Ep-CAM) also belongs to this category. As a homotypic cell adhesion molecule for epithelial cells, it is located in the intercellular space. Interestingly, high-affinity anti-Ep-CAM antibodies are very toxic, whereas moderate-affinity antibodies are well tolerated. This suggests that not only accessibility of Ep-CAM targets to normal cells but also kinetics of antibody binding may open new therapeutic windows.

Eight antibodies have been approved for treating neoplastic tissue-related diseases, but most of them are against lymphoma and leukemia (Adams, G. P. & Weiner, L. M. (2005) Nat. Biotechnol. 23, 1147-1157). Only three monoclonal antibodies, that is, Herceptin, Avastin, and Erbitux, address solid tumor types, which account for more than 90% of cancer-evoked mortality. mAbs for which substantially remaining medical requests and remarkable clinical benefits are approved have already been provided, and their significant commercial success has also provided a motivation to develop new innovative approaches, in which that development of antibody-based therapies is well balanced with enhanced efficacy thereof, for different groups of patients (Brekke, O. H. & Sandlie, I. (2003) Nat. Rev. Drug Discov. 2, 52-62; Carter, P. (2001) Nat. Rev. Cancer 1, 118-129).

One of the challenges to be mastered with emergence of upgraded next-generation antibody-based cancer therapies is to select appropriate target molecules which are key factors for a favorable toxicity/efficacy profile.

Current antibodies available for the treatment of solid tumor do not fully exert the cumulative force of the mode of action inherent in the antibody molecules due to expression of their targets on normal tissues. For example, Her2/neu, a target of Herceptin, is expressed in many normal human tissues, including heart muscle (Crone, S. A., Zhao, Y. Y., Fan, L., Gu, Y., Minamisawa, S., Liu, Y., Peterson, K. L., Chen, J., Kahn, R., Condorelli, G. et al. (2002) Nat. Med. 8, 459-465). As a result, Herceptin is designed to have decreased immunity, and thus cannot be dosed at the maximum effective amount, because otherwise unacceptable toxicity occurs. As such, the "measures of blunting a potentially sharp blade" limit therapeutic efficacy of Herceptin.

In addition to preventing expression in normal tissues associated with toxicity, the desirable features of ideal antibody targets are to exhibit potent and high expression levels on the surface of tumor cells while exhibiting the tumor-promoting function (Houshmand, P. & Zlotnik, A. (2003) Curr. Opin. CellBiol. 15, 640-644).

Technical Problem

An object of the present invention is to provide a binding molecule specific for Lrig-1 protein present on the surface of regulatory T cells (Treg cells).

Another object of the present invention is to provide a nucleic acid molecule which encodes the binding molecule according to the present invention.

Yet another object of the present invention is to provide an expression vector into which the nucleic acid molecule according to the present invention is inserted.

Still yet another object of the present invention is to provide a host cell line transfected with the expression vector according to the present invention.

Still yet another object of the present invention is to provide an antibody-drug conjugate according to the present invention.

Still yet another object of the present invention is to provide a pharmaceutical composition for preventing or treating cancer, comprising the binding molecule according to the present invention.

However, the technical problem to be solved by the present invention is not limited to the above-mentioned problems, and other problems which are not mentioned will be clearly understood by those skilled in the art from the following description.

Solution to Problem

The present inventors have discovered Lrig-1 protein that is present specifically on the surface of regulatory T cells, have selected an epitope on the protein, and have produced a monoclonal antibody capable of specifically binding to the Lrig-1 protein, thereby completing the present invention.

According to an embodiment of the present invention, there is provided a binding molecule which specifically binds to leucine-rich and immunoglobulin-like domains 1 (Lrig-1) protein.

As used herein, the term "binding molecule" refers to a variable domain comprising an intact immunoglobulin that includes a monoclonal antibody, such as a chimeric, humanized, or human monoclonal antibody, or an immunoglobulin that binds to an antigen, for example, an immunoglobulin fragment that competes with intact immunoglobulins for binding to monomeric HA or trimeric HA of influenza A virus. Regardless of the structure, an antigen-binding fragment binds to the same antigen recognized by intact immunoglobulins. The antigen-binding fragment may include a peptide or polypeptide which contains, out of the amino acid sequence of the binding molecule, an amino acid sequence of two or more contiguous residues, 20 or more contiguous amino acid residues, 25 or more contiguous amino acid residues, 30 or more contiguous amino acid residues, 35 or more contiguous amino acid residues, 40 or more contiguous amino acid residues, 50 or more contiguous amino acid residues, 60 or more contiguous amino acid residues, 70 or more contiguous amino acid residues, 80 or more contiguous amino acid residues, 90 or more contiguous amino acid residues, 100 or more contiguous amino acid residues, 125 or more contiguous amino acid residues, 150 or more contiguous amino acid residues, 175 or more contiguous amino acid residues, 200 or more contiguous amino acid residues, or 250 or more contiguous amino acid residues. The term "antigen-binding fragment", in particular, includes Fab, F(ab'), F(ab')2, Fv, dAb, Fd, complementarity determining region (CDR) fragments, single-chain antibodies (scFvs), bivalent single-chain antibodies, single-chain phage antibodies, diabodies, triabodies, tetrabodies, polypeptides containing at least one fragment of immunoglobulin which is sufficient for a particular antigen to bind to the polypeptide, and the like. The fragment may be produced synthetically or by enzymatic or chemical digestion of a complete immunoglobulin, or may be produced by genetic engineering methods using recombinant DNA techniques. Production methods are well known in the art.

In the present invention, the Lrig-1 protein is a transmembrane protein consisting of 1091 amino acids present on the surface of regulatory T cells, and is composed of leucine-rich repeats (LRRs) and three immunoglobulin-like domains on the extracellular or lumen side, a cell transmembrane sequence, and a cytoplasmic tail portion. The LRIG gene family includes LRIG1, LRIG2, and LRIG3, and the amino acids therebetween are highly conserved. The LRIG1 gene is highly expressed in normal skin and can be expressed in basal and hair follicle cells to regulate proliferation of epithelial stem cells. Therefore, the LRIG1 gene plays an important role in maintaining homeostasis of the epidermis, and its absence may develop psoriasis or skin cancer. It has been reported that in a case where chromosome 3p14.3 portion in which LRIG1 is located is cut off, there is a possibility of developing into cancer cells. In fact, it was identified that expression of LRIG1 is greatly decreased in renal cell carcinoma and cutaneous squamous cell carcinoma. Recently, it has been also found that Lrig-1 is expressed in only about 20 to 30% of cancers. On the other hand, for the purpose of the present invention, the Lrig-1 protein may be, but is not limited to, a protein present in humans or mice.

In the present invention, the Lrig-1 protein may be, but is not limited to, a human-derived polypeptide represented by SEQ ID NO: 1 or a mouse-derived polypeptide represented by SEQ ID NO: 3.

In addition, in the present invention, the Lrig-1 protein represented by SEQ ID NO: 1 may be encoded by a polynucleotide represented by SEQ ID NO: 2, but is not limited thereto.

In addition, in the present invention, the Lrig-1 protein represented by SEQ ID NO: 3 may be encoded by a polynucleotide represented by SEQ ID NO: 4, but is not limited thereto.

In the present invention, the binding molecule may be a binding molecule, comprising:
a heavy chain variable region that contains a heavy chain CDR1 consisting of an amino acid sequence selected from the group consisting of SEQ ID NOs: 5, 13, 21, and 29; a heavy chain CDR2 consisting of an amino acid sequence selected from the group consisting of SEQ ID NOs: 6, 14, 22, and 30; a heavy chain CDR3 consisting of an amino acid sequence selected from the group consisting of SEQ ID NOs: 7, 15, 23, and 31; and a light chain variable region that contains a light chain CDR1 consisting of an amino acid sequence selected from the group consisting of SEQ ID NOs: 8, 16, 24, and 32; a light chain CDR2 consisting of an amino acid sequence selected from the group consisting of SEQ ID NOs: 9, 17, 25, and 33; a light chain CDR3 consisting of an amino acid sequence selected from the group consisting of SEQ ID NO: 10, 18, 26, and 34.

In the present invention, the binding molecule may be a binding molecule, comprising:

a heavy chain variable region, selected from the group consisting of the following (a) to (d):

(a) a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7;

(b) a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15;

(c) a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and (d) a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region, selected from the group consisting of the following (e) to (h):

(e) a light chain variable region that contains a light chain CDR1 represented by SEQ ID NO: 8, a light chain CDR2 represented by SEQ ID NO: 9, and a light chain CDR3 represented by SEQ ID NO: 10;

(f) a light chain variable region that contains a light chain CDR1 represented by SEQ ID NO: 16, a light chain CDR2 represented by SEQ ID NO: 17, and a light chain CDR3 represented by SEQ ID NO: 18;

(g) a light chain variable region that contains a light chain CDR1 represented by SEQ ID NO: 24, a light chain CDR2 represented by SEQ ID NO: 25, and a light chain CDR3 represented by SEQ ID NO: 26;

(h) a light chain variable region that contains a light chain CDR1 represented by SEQ ID NO: 32, a light chain CDR2 represented by SEQ ID NO: 33, and a light chain CDR3 represented by SEQ ID NO: 34.

In the present invention, the binding molecule may be a binding molecule selected from the group consisting of the following (1) to (4):

(1) a binding molecule comprising a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7; and a light chain variable region that contains a light chain CDR1 represented by SEQ ID NO: 8, a light chain CDR2 represented by SEQ ID NO: 9, and a light chain CDR3 represented by SEQ ID NO: 10;

(2) a binding molecule comprising a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15; and a light chain variable region that contains a light chain CDR1 represented by SEQ ID NO: 16, a light chain CDR2 represented by SEQ ID NO: 17, and a light chain CDR3 represented by SEQ ID NO: 18;

(3) a binding molecule comprising a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and a light chain variable region that contains a light chain CDR1 represented by SEQ ID NO: 24, a light chain CDR2 represented by SEQ ID NO: 25, and a light chain CDR3 represented by SEQ ID NO: 26;

(4) a binding molecule comprising a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region that contains a light chain CDR1 represented by SEQ ID NO: 32, a light chain CDR2 represented by SEQ ID NO: 33, and a light chain CDR3 represented by SEQ ID NO: 34.

In the present invention, the binding molecule may be a binding molecule, comprising:

a heavy chain variable region consisting of any one amino acid sequence selected from the group consisting of SEQ ID NOs: 11, 19, 27, and 35; and a light chain variable region consisting of any one amino acid sequence selected from the group consisting of SEQ ID NO: 12, 20, 28, and 36.

In the present invention, the binding molecule may be a binding molecule selected from the group consisting of the following binding molecules:

a binding molecule comprising a heavy chain variable region represented by SEQ ID NO: 11, and a light chain variable region represented by SEQ ID NO: 12;

a binding molecule comprising a heavy chain variable region represented by SEQ ID NO: 19, and a light chain variable region represented by SEQ ID NO: 20;

a binding molecule comprising a heavy chain variable region represented by SEQ ID NO: 27, and a light chain variable region represented by SEQ ID NO: 28; and a binding molecule comprising a heavy chain variable region represented by SEQ ID NO: 35, and a light chain variable region represented by SEQ ID NO: 36.

In the present invention, the binding molecule may further comprise a fragment crystallization (Fc) region or a constant region. Here, the Fc region may be an Fc region of an IgG1, IgG2, IgG3, or IgG4 antibody, or may be derived therefrom. Alternatively, the Fc region may be a hybrid Fc region.

In the present invention, the Fc region may be an Fc region of a mammalian-derived IgG1, IgG2, IgG3, or IgG4 antibody, and may preferably be an Fc region of a human-derived IgG1, IgG2, IgG3, or IgG4 antibody.

In the present invention, the Fc region may be an Fc region of a mammalian-derived IgG1, IgG2, IgG3, or IgG4 antibody, and may preferably be an Fc region of a human-derived IgG1, IgG2, IgG3, or IgG4 antibody. However, the Fc region is not limited thereto.

As an example of the present invention, the constant region may be a mouse-derived IgG2a constant region represented by SEQ ID NO: 37, but is not limited thereto.

As an example of the present invention, the constant region may be a mouse-derived immunoglobulin kappa constant region represented by SEQ ID NO: 38, but is not limited thereto.

As an example of the present invention, the constant region may be a human-derived IgG1 constant region represented by SEQ ID NO: 39, but is not limited thereto.

As an example of the present invention, the constant region may be a human-derived immunoglobulin kappa constant region represented by SEQ ID NO: 40, but is not limited thereto.

As an example of the present invention, the constant region may be a human-derived IgG2 constant region represented by SEQ ID NO: 41, but is not limited thereto.

As an example of the present invention, the constant region may be a human-derived IgG3 constant region represented by SEQ ID NO: 42, but is not limited thereto.

As an example of the present invention, the constant region may be a human-derived IgG4 constant region represented by SEQ ID NO: 43, but is not limited thereto.

As an example of the present invention, the Fc region may be a human-derived immunoglobulin lambda constant region, but is not limited thereto.

In the present invention, the "hybrid Fc" may be derived from a combination of human IgG subclasses or a combination of human IgD and IgG. In a case where the hybrid Fc binds to a biologically active molecule, polypeptide, or the like, the hybrid Fc has effects of not only increasing a serum half-life of the biologically active molecule, but also increasing an expression level of the polypeptide when a nucleotide sequence encoding the Fc-polypeptide fusion protein is expressed.

As an example of the present invention, the hybrid Fc region may be represented by SEQ ID NO: 44, but is not limited thereto.

In the binding molecule of the present invention, the Fc or constant region may be linked, via a linker, to the variable region. Here, the linker may be linked to the C-terminus of the Fc, and the N-terminus of the binding molecule of the present invention may be linked to the linker. However, the present invention is not limited thereto.

In the present invention, the "linker" may contain a sequence that can be cleaved by an enzyme that is overexpressed in a tissue or cell having a target disease. In a case where the linker may be cleaved by the overexpressed enzyme as described above, it is possible to effectively prevent activity of a polypeptide from decreasing due to the Fc portion. In the present invention, an example of the linker may be preferably a peptide linker consisting of 33 amino acids located in the $282^{nd}$ to $314^{th}$ portion of human albumin which is most abundantly present in the blood, and more preferably a peptide linker consisting of 13 amino acids located in the $292^{nd}$ to $304^{th}$ portion of the human albumin. Such portions are portions which are mostly exposed to the outside in three-dimensional structure, and thus has a minimum possibility of inducing an immune response in the body. However, the linker is not limited thereto.

The binding molecule of the present invention may further comprise a heavy chain constant region consisting of an amino acid sequence selected from the group consisting of SEQ ID NOs: 37, 39, 41, 42, 43, and 44.

The binding molecule of the present invention may further comprise a light chain constant region consisting of an amino acid sequence represented by SEQ ID NO: 38 or 40.

The binding molecule of the present invention may further comprise:

a heavy chain constant region consisting of an amino acid sequence represented by SEQ ID NO: 37; and a light chain constant region consisting of an amino acid sequence represented by SEQ ID NO: 38.

The binding molecule of the present invention may further comprise:

a heavy chain constant region consisting of an amino acid sequence represented by SEQ ID NO: 39, 41, 42, or 43; and a light chain constant region consisting of an amino acid sequence represented by SEQ ID NO: 40.

The binding molecule of the present invention may further comprise:

a heavy chain constant region consisting of an amino acid sequence represented by SEQ ID NO: 44.

The binding molecule of the present invention may be a binding molecule selected from the group of the following binding molecules:

a binding molecule comprising a heavy chain represented by SEQ ID NO: 45, and a light chain represented by SEQ ID NO: 46;

a binding molecule comprising a heavy chain represented by SEQ ID NO: 47, and a light chain represented by SEQ ID NO: 48;

a binding molecule comprising a heavy chain represented by SEQ ID NO: 49, and a light chain represented by SEQ ID NO: 50; and a binding molecule comprising a heavy chain represented by SEQ ID NO: 51, and a light chain represented by SEQ ID NO: 52.

The binding molecule of the present invention is characterized by being an antibody, but is not limited thereto. The antibody includes all of a monoclonal antibody, a full-length antibody, or an antibody fragment which is a portion of an antibody, has the ability to bind to Lrig-1 protein, and competes with the binding molecule of the present invention in binding to an epitope on Lrig-1.

As used herein, the term "antibody" refers to a protein molecule which serves as a receptor that specifically recognizes an antigen, including an immunoglobulin molecule that is immunologically reactive with a particular antigen. For the purpose of the present invention, the antigen may be Lrig-1 protein present on the surface of regulatory T cells. Preferably, the antibody may specifically recognize the leucine-rich region or immunoglobulin-like domain of the Lrig-1 protein, but is not limited thereto.

In the present invention, the "immunoglobulin" has a heavy chain and a light chain, and each of the heavy chain and the light chain comprises a constant region and a variable region. The variable region of each of the light chain and the heavy chain contains three hypervariable regions called complementarity determining regions (hereinafter referred to as "CDRs") and four framework regions. The CDRs primarily serve to bind to an epitope on an antigen. The CDRs of each chain are typically referred to as CDR1, CDR2, and CDR3 sequentially starting from the N-terminus, and are also distinguished by the chain where particular CDRs are located.

In addition, as used herein, the term "monoclonal antibody" refers to an antibody molecule of a single molecular composition which is obtained from substantially the same antibody population, and exhibits single binding specificity and affinity for a particular epitope.

In the present invention, the "full-length antibody" has a structure with two full-length light chains and two full-length heavy chains in which each light chain is linked to a heavy chain by disulfide bond, and includes IgA, IgD, IgE, IgM, and IgG. The IgG includes, as subtypes thereof, IgG1, IgG2, IgG3, and IgG4.

In addition, as used herein, the term "antigen fragment" refers to a fragment that retains an antigen-binding function, and includes Fab, Fab', F(ab')$_2$, Fv, and the like. The Fab has a structure with variable regions of light and heavy chains, a constant region of the light chain, and a first constant region (CH1 domain) of the heavy chain, and has one antigen-binding site. In addition, Fab' is different from Fab in that Fab' has a hinge region containing at least one cysteine residue at the C-terminus of the heavy chain CH1 domain. F(ab')$_2$ antibodies are produced with cysteine residues at the hinge region of Fab' forming disulfide bond. Fv (variable fragment) refers to the smallest antibody fragment having only a heavy chain variable region and a light chain variable region. Double-chain Fv (dsFv) is configured to be such that a heavy chain variable region and a light chain variable region are linked to each other by disulfide bond, and single-chain Fv (scFv) is configured to be such that a heavy chain variable region and a light chain variable region are covalently linked to each other, in general, via a peptide linker. The antibody fragment may be obtained as Fab or F(ab')2 fragment in a case where a proteolytic enzyme, for example, papain or pepsin is used, and may be produced through a genetic recombinant technique.

In addition, in the present invention, the antibody may be, but is not limited to, a chimeric antibody, a humanized antibody, a bivalent, bispecific molecule, a minibody, a domain antibody, a bispecific antibody, an antibody mimetic, a diabody, a triabody, or a tetrabody, or a fragment thereof.

In the present invention, the "chimeric antibody" is an antibody which is obtained by recombination of a variable region of a mouse antibody and a constant region of a human antibody, and has a greatly improved immune response as compared with the mouse antibody.

In addition, as used herein, the term "humanized antibody" refers to an antibody obtained by modifying a protein sequence of an antibody derived from a non-human species so that the protein sequence is similar to an antibody variant naturally produced in humans. For example, the humanized antibody may be prepared as follows. Mouse-derived CDRs may be recombined with a human antibody-derived FR to prepare a humanized variable region, and the humanized variable region may be recombined with a constant region of a preferred human antibody to prepare a humanized antibody.

In the present invention, the binding molecule may be provided as a bispecific antibody or a bispecific antigen-binding fragment which is capable of binding to Lrig-1 protein and also binding to another protein.

In the present invention, the bispecific antibody and the bispecific antigen-binding fragment may comprise the binding molecule according to the present invention. As an example of the present invention, the bispecific antibody and the bispecific antigen-binding fragment comprise an antigen-binding domain capable of binding to Lrig-1 protein, wherein the antigen-binding domain capable of binding to Lrig-1 may comprise or consist of the binding molecule according to the present invention.

The bispecific antibody and the bispecific antigen-binding fragment provided in the present invention comprise an antigen-binding domain, which is a binding molecule capable of binding to Lrig-1 protein according to the present invention, and an antigen-binding domain capable of binding to another target protein. Here, the antigen-binding domain capable of binding another target protein may be an antigen-binding domain capable of binding to a protein other than Lrig-1 protein, for example, PD-1 or a cell surface receptor. However, the antigen-binding domain is not limited thereto.

The bispecific antibody and the bispecific antigen-binding fragment according to the present invention may be provided in any suitable format, for example, that described in Kontermann MAbs 2012, 4(2): 182-197, which is incorporated herein by reference in its entirety. For example, the bispecific antibody or the bispecific antigen-binding fragment may be a bispecific antibody conjugate (for example, IgG2, F(ab')2, or CovX-body), a bispecific IgG or IgG-like molecule (for example, IgG, scFv4-Ig, IgG-scFv, scFv-IgG, DVD-Ig, IgG-sVD, sVD-IgG, or 2 in 1-IgG, mAb2, or Tandemab common LC), an asymmetric bispecific IgG or IgG-like molecule (for example, kih IgG, kih IgG common LC, CrossMab, kih IgG-scFab, mAb-Fv, charge pair, or SEED-body), a small bispecific antibody molecule (for example, diabody (db), dsDb, DART, scDb, tandAb, tandem scFv (taFv), tandem dAb/VHH, triple body, triple head, Fab-scFv, or F(ab')2-scFv2), a bispecific Fc and CH3 fusion protein (for example, taFv-Fc, di-diabody, scDb-CH3, scFv-Fc-scFv, HCAb-VHH, scFv-kih-Fc, or scFv-kih-CH3), or a bispecific fusion protein (for example, scFv2-albumin, scDb-albumin, taFv-toxin, DNL-Fab3, DNL-Fab4-IgG, DNL-Fab4-IgG-cytokine 2). See, in particular, FIG. 2 in Kontermann MAbs 2012, 4(2): 182-19. The bispecific antibody and the bispecific antigen-binding fragment according to the invention may be designed and prepared by those skilled in the art.

A method for producing the bispecific antibody in the present invention comprises forming a reducing disulfide or non-reducing thioether bond, and chemical crosslinking of an antibody or antibody fragment as described, for example, in Segal and Bast, 2001. Production of Bispecific Antibodies. Current Protocols in Immunology. 14:IV:2.13:2.13.1-2.13.16, which is incorporated herein by reference in its entirety. For example, N-succinimidyl-3-(-2-pyridyldithio)-propionate (SPDP) may be used, for example, for chemically crosslinking an Fab fragment through an SH-group at the hinge region, to generate a disulfide-linked bispecific F(ab)2 heterodimer.

In addition, an alternative method for producing the bispecific antibody in the present invention comprises fusing an antibody-producing hybridoma with, for example, polyethylene glycol, to produce quadroma cells capable of secreting bispecific antibodies, as described, for example, in D. M. and Bast, B. J. 2001. Production of Bispecific Antibodies. Current Protocols in Immunology. 14:IV:2.13: 2.13.1-2.13.16.

The bispecific antibody and the bispecific antigen-binding fragment according to the invention may also be, for example, recombinantly produced by expression from a nucleic acid construct that encodes a polypeptide for an antigen-binding molecule, as described, for example, in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339, both of which are incorporated herein by reference in their entireties.

For example, a DNA construct that contains a sequence encoding light and heavy chain variable domains for two antigen-binding domains (that is, light and heavy chain variable domains for an antigen-binding domain capable of binding to PD-1, and light and heavy chain variable domains for an antigen-binding domain capable of binding to another target protein), and a sequence encoding a suitable linker or dimerization domain between the antigen-binding domains may be prepared by molecular cloning techniques. Subsequently, a recombinant bispecific antibody may be produced by expression of the construct (for example, in vitro) in a suitable host cell (for example, a mammalian host cell), and then the expressed recombinant bispecific antibody may be optionally purified.

Antibodies may be produced by an affinity maturation process in which a modified antibody with improved affinity for an antigen as compared with an unmodified parent antibody is produced. An affinity matured antibody may be produced by a procedure known in the art, for example, in Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7): 3310-159 (1995); and Hawkins et al, J. Mol. Biol. 226:889-896 (1992).

In addition, the binding molecule provided in the present invention may include a variant of the amino acid sequence as long as the variant can specifically bind to Lrig-1 protein. For example, in order to improve binding affinity and/or other biological properties of an antibody, modifications may be made to an amino acid sequence of the antibody. Such modifications include, for example, deletions, insertions, and/or substitutions of amino acid sequence residues of the antibody.

Such amino acid variations are made based on relative similarity of amino acid side chain substituents such as hydrophobicity, hydrophilicity, charge, and size. According to analysis on sizes, shapes, and types of amino acid side chain substituents, it can be seen that arginine, lysine, and histidine are all positively charged residues; alanine, glycine, and serine have similar sizes; and phenylalanine, tryptophan, and tyrosine have similar shapes. Thus, based on these considerations, it can be said that arginine, lysine, and histidine; alanine, glycine, and serine; and phenylalanine, tryptophan, and tyrosine are biologically functional equivalents.

In introducing variations, the hydropathic index of amino acids may be considered. Each amino acid has been assigned hydropathic index depending on its hydrophobicity and charge: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The hydropathic amino acid index is very important in conferring the interactive biological function on a protein. It is known that substitution with an amino acid having similar hydropathic index allows a protein to retain similar biological activity. In a case where variations are introduced with reference to the hydropathic index, substitutions are made between amino acids that exhibit a hydropathic index difference of preferably within ±2, more preferably within ±1, and even more preferably within ±0.5.

Meanwhile, it is also well known that substitutions between amino acids having similar hydrophilicity values result in proteins with equivalent biological activity. As disclosed in U.S. Pat. No. 4,554,101, respective amino acid residues have been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In a case where variations are introduced with reference to the hydrophilicity values, substitutions may be made between amino acids that exhibit a hydrophilicity value difference of preferably within ±2, more preferably within ±1, and even more preferably within ±0.5.

Amino acid exchanges in proteins which do not entirely alter activity of a molecule are known in the art (H. Neurath, R. L. Hill, The Proteins, Academic Press, New York (1979)). The most commonly occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Gln/Glu.

Given the above-described variations with biologically equivalent activity, it is interpreted that the binding molecule of the present invention also includes sequences that exhibit substantial identity with the sequences listed in the Sequence Listing.

As used herein, the term "substantial identity" refers to a sequence showing at least 61% homology, more preferably 70% homology, even more preferably 80% homology, and most preferably 90% homology when the sequence of the present invention is aligned with any other sequence so that they maximally correspond to each other, and the aligned sequence is analyzed by using an algorithm typically used in the art. Alignment methods for comparison of sequences are known in the art. Various methods and algorithms for alignment are disclosed in Smith and Waterman, Adv. Appl. Math. 2:482 (1981); Needleman and Wunsch, J. Mol. Bio. 48:443 (1970); Pearson and Lipman, Methods in Mol. Biol. 24: 307-31(1988); Higgins and Sharp, Gene 73:237-44 (1988); Higgins and Sharp, CABIOS 5:151-3(1989); Corpet et al., Nuc. Acids Res. 16:10881-90(1988); Huang et al., Comp. Appl. BioSci. 8:155-65(1992); and Pearson et al., Meth. Mol. Biol. 24:307-31(1994). NCBI Basic Local Alignment Search Tool (BLAST) (Altschul et al., J. Mol. Biol. 215: 403-10 (1990)) is accessible from the National Center for Biological Information (NBCI), or the like, and may be used in conjunction with sequencing programs, such as blastp, blasm, blastx, tblastn, and tblastx, on the internet. BLSAT is accessible at www.ncbi.nlm.nih.gov/BLAST/. Sequence homology comparison methods using this program can be identified online (www.ncbi.nlm.nih.gov/BLAST/blast_help.html).

In the present invention, the binding molecule, preferably the antibody, may be produced by a conventional method for producing an antibody, and may be produced by affinity maturation.

As used herein, the term "affinity maturation" refers to a process in which antibodies having increased affinity for an antigen are produced by activated B cells in the course of an immune response. For the purpose of the present invention, the affinity maturation allows antibodies or antibody fragments to be produced due to affinity maturation based on the principles of mutation and selection, in the same process that occurs in nature.

The binding molecule, preferably the antibody, provided in the present invention may suppress the function, particularly of regulatory T immune cells (Treg cells), among immune cells, thereby effectively preventing, ameliorating, or treating cancer.

In the present invention, the term "cancer" refers to or indicates a physiological condition characterized by cell growth in mammals which is not regulated in a typical manner. The cancer to be prevented, ameliorated, or treated in the present invention may be solid tumor formed of agglomerates caused by abnormal growth of cells in a solid organ, and may be, but is not limited to, gastric cancer, liver cancer, gliocytoma, ovarian cancer, colorectal cancer, head and neck cancer, bladder cancer, renal cell cancer, breast cancer, metastatic cancer, prostate cancer, pancreatic cancer, melanoma, lung cancer, or the like, depending on location of the solid organ, with melanoma being preferred.

According to another embodiment of the present invention, there is provided a nucleic acid molecule encoding the binding molecule provided in the present invention.

The nucleic acid molecule of the present invention includes all nucleic acid molecules obtained by translating the amino acid sequences of the binding molecules provided in the present invention to polynucleotide sequences, as known to those skilled in the art. Therefore, various polynucleotide sequences may be prepared by an open reading frame (ORF), and all of these polynucleotide sequences are also included in the nucleic acid molecule of the present invention.

According to yet another embodiment of the present invention, there is provided an expression vector into which the isolated nucleic acid molecule provided in the present invention is inserted.

In the present invention, the "vector" is a nucleic acid molecule capable of transporting another nucleic acid linked thereto. One type of vector is a "plasmid," which refers to circular double-stranded DNA into which an additional DNA segment can be ligated. Another type of vector is a phage vector. Yet another type of vector is a viral vector, where an additional DNA segment can be ligated into the viral genome. Certain vectors are capable of autonomous replication in a host cell into which they are introduced (for example, bacterial vectors having a bacterial origin of replication are episomal mammalian vectors). Other vectors (for example, non-episomal mammalian vectors) can be integrated into the genome of a host cell upon introduction into the host cell, and thus are replicated along with the host genome. In addition, certain vectors are capable of directing expression of genes to which they are operatively linked. Such vectors are referred to herein as "recombinant expression vectors" or simply "expression vectors." In general, expression vectors useful in recombinant DNA techniques are often in the form of plasmids. In the present specification, "plasmid" and "vector" may be used interchangeably as the plasmid is the most commonly used form of vector.

Specific examples of the expression vector in the present invention may be selected from, but are not limited to, the group consisting of commercially widely used pCDNA vectors, F, R1, RP1, Col, pBR322, ToL, Ti vectors; cosmids; phages such as lambda, lambdoid, M13, Mu, p1 P22, Qμμ, T-even, T2, T3, T7; plant viruses. Any expression vector known, to those skilled in the art, as expression vectors can be used in the present invention, and the expression vector is selected depending on the nature of the target host cell. Introduction of a vector into a host cell may be performed by calcium phosphate transfection, viral infection, DEAE-dextran-mediated transfection, lipofectamine transfection, or electroporation. However, the present invention is not limited thereto, and those skilled in the art may adopt and use an introduction method appropriate for the expression vector and the host cell which are used. The vector may preferably contain at least one selection marker. However, the present invention is not limited thereto, and selection can be made using the vector that contains no selection marker, depending on whether or not a product is produced. The selection marker is selected depending on the target host cell, which is done using methods already known to those skilled in the art, and thus the present invention has no limitation thereon.

In order to facilitate purification of the nucleic acid molecule of the present invention, a tag sequence may be inserted into and fused to an expression vector. The tag includes, but is not limited to, hexa-histidine tag, hemagglutinin tag, myc tag, or flag tag, and any tag known to those skilled in the art which facilitates purification can be used in the present invention.

According to still yet another embodiment of the present invention, there is provided a host cell line transfected with the expression vector provided in the present invention.

In the present invention, the "host cell" includes individual cells or cell cultures which may be or have been recipients of the vector(s) for incorporation of a polypeptide insert. The host cell includes progeny of a single host cell, and the progeny may not necessarily be completely identical (in morphology or in genomic DNA complement) to the original parent cell due to natural, accidental, or intentional mutation. The host cell includes cells transfected in vivo with the polynucleotide(s) herein.

In the present invention, the host cell may include cells of mammalian, plant, insect, fungal, or cellular origin, and may be, for example, bacterial cells such as *E. coli, Streptomyces, Salmonella typhimurium*; fungal cells such as yeast cells and *Pichia pastoris*; insect cells such as *Drosophila* and *Spodoptera* Sf9 cells; animal cells such as Chinese hamster ovary (CHO) cells, SP2/0 (mouse myeloma), human lymphoblastoid, COS, NSO (mouse myeloma), 293T, Bowes melanoma cells, HT-1080, baby hamster kidney (BHK) cells, human embryonic kidney (HEK) cells, or PERC.6 (human retinal cells); or plant cells. However, the host cell is not limited thereto, and any cell known to those skilled in the art which can be used as a host cell line is available.

According to still yet another embodiment of the present invention, there is provided an antibody-drug conjugate (ADC) comprising the antibody provided in the present invention and a drug.

As used herein, the term "antibody-drug conjugate (ADC)" refers to a form in which the drug and the antibody are chemically linked to each other without degrading biological activity of the antibody and the drug. In the present invention, the antibody-drug conjugate denotes a form in which the drug is bound to an amino acid residue at the N-terminus of the heavy and/or light chain of the antibody, specifically, a form in which the drug is bound to an α-amine group at the N-terminus of the heavy and/or light chain of the antibody.

As used herein, the term "drug" may mean any substance having a certain biological activity for a cell, which is a concept including DNA, RNA, or a peptide. The drug may be in a form which contains a reactive group capable of reacting and crosslinking with an α-amine group, and also includes a form which contains a reactive group capable of reacting and crosslinking with an α-amine group and to which a linker is linked.

In the present invention, examples of the reactive group capable of reacting and crosslinking with the α-amine group are not particularly limited in terms of type as long as the reactive group can react and crosslink with an α-amine group at the N-terminus of a heavy or light chain of an antibody. The reactive group includes all types of groups known in the art which react with an amine group. The reactive group may, for example, be any one of isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester, but is not limited thereto. In the present invention, the drug is a drug capable of treating cancer, which is a disease targeted by the Lrig-1 antibody, and may be an anticancer agent.

In the present invention, the anticancer agent may be selected from, but is not limited thereto, the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, capecitabine, decitabine, mercaptopurine, thioguanine, cladribine, carmofur, raltitrexed, docetaxel, paclitaxel, irinotecan, belotecan, topotecan, vinorelbine, etoposide, vinblastine, idarubicin, mitomycin, bleomycin, dactinomycin, pirarubicin, aclarubicin, peplomycin, temsirolimus, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, olaparib, navelbine, fadrozole, tamoxifen, toremifene, testolactone, anastrozole, letrozole, vorozole, bicalutamide, lomustine, 5FU, vorinostat, entinostat, and carmustine.

According to still yet another embodiment of the present invention, there is provided a pharmaceutical composition for preventing or treating cancer, comprising, as an active ingredient, the binding molecule or antibody-drug conjugate (ADC) provided in the present invention.

In the present invention, the term "cancer" refers to or indicates a physiological condition characterized by cell growth in mammals which is not regulated in a typical manner. The cancer to be prevented, ameliorated, or treated in the present invention may be solid tumor formed of agglomerates caused by abnormal growth of cells in a solid organ, and may be, but is not limited to, gastric cancer, liver cancer, gliocytoma, ovarian cancer, colorectal cancer, head and neck cancer, bladder cancer, renal cell cancer, breast cancer, metastatic cancer, prostate cancer, pancreatic cancer, melanoma, lung cancer, or the like, depending on location of the solid organ, with melanoma being preferred. On the other hand, in the present invention, the "prevention" may include, without limitation, any act of blocking symptoms of a disease, or suppressing or delaying the symptoms, using the pharmaceutical composition of the present invention.

In addition, in the present invention, the "treatment" may include, without limitation, any act of ameliorating or beneficially altering symptoms of a disease, using the pharmaceutical composition of the present invention.

In the present invention, the pharmaceutical composition may be characterized by being in the form of capsules, tablets, granules, injections, ointments, powders, or beverages, and the pharmaceutical composition may be characterized by being targeted to humans.

In the present invention, the pharmaceutical composition may be formulated in the form of oral preparations such as powders, granules, capsules, tablets, and aqueous suspensions, preparations for external use, suppositories, and sterile injectable solutions, respectively, according to conventional methods, and used. However, the pharmaceutical composition is not limited thereto. The pharmaceutical composition of the present invention may further comprise a pharmaceutically acceptable carrier. As the pharmaceutically acceptable carrier, a binder, a glidant, a disintegrant, an excipient, a solubilizer, a dispersant, a stabilizer, a suspending agent, a pigment, a flavor, and the like may be used for oral administration; a buffer, a preserving agent, a pain-relieving agent, a solubilizer, an isotonic agent, a stabilizer, and the like may be used in admixture for injections; and a base, an excipient, a lubricant, a preserving agent, and the like may be used for topical administration. The preparations of the pharmaceutical composition of the present invention may be prepared in various ways by being mixed with the pharmaceutically acceptable carrier as described above. For example, for oral administration, the pharmaceutical composition may be formulated in the form of tablets, troches, capsules, elixirs, suspensions, syrups, wafers, or the like. For injections, the pharmaceutical composition may be formulated in the form of unit dosage ampoules or multiple dosage forms. Alternatively, the pharmaceutical composition may be formulated into solutions, suspensions, tablets, capsules, sustained-release preparations, or the like.

Meanwhile, as examples of carriers, diluents, or excipients suitable for making preparations, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, or the like may be used. In addition, a filler, an anti-coagulant, a lubricant, a wetting agent, a fragrance, an emulsifier, a preservative, and the like may further be included.

The route of administration of the pharmaceutical composition of the present invention includes, but is not limited to, oral, intravenous, intramuscular, intraarterial, intramedullary, intradural, intracardiac, transdermal, subcutaneous, intraperitoneal, intranasal, intestinal, topical, sublingual, or rectal route. Oral or parenteral administration is preferred.

In the present invention, the "parenteral" includes subcutaneous, intradermal, intravenous, intramuscular, intraarticular, intrabursal, intrasternal, intradural, intralesional, and intracranial injection or infusion techniques. The pharmaceutical composition of the present invention may also be administered in the form of suppositories for rectal administration.

The pharmaceutical composition of the present invention may vary depending on a variety of factors, including activity of a certain compound used, the patient's age, body weight, general health status, sex, diet, time of administration, route of administration, rate of excretion, drug combination, and severity of a certain disease to be prevented or treated. A dose of the pharmaceutical composition may vary depending on the patient's condition, body weight, severity of disease, drug form, route of administration, and duration, and may be appropriately selected by those skilled in the art. The pharmaceutical composition may be administered in an amount of 0.0001 to 50 mg/kg or 0.001 to 50 mg/kg, per day. Administration may be made once a day or several times a day. The dose is not intended to limit the scope of the invention in any way. The pharmaceutical composition according to the present invention may be formulated in the form of pills, sugar-coated tablets, capsules, liquids, gels, syrups, slurries, or suspensions.

Advantageous Effects of Invention

The binding molecule, preferably the antibody, specific for the Lrig-1 protein according to the present invention can suppress the function of regulatory T cells to effectively prevent, ameliorate, or treat cancer, particularly solid tumor.

In addition, the binding molecule, preferably the antibody, specific for the Lrig-1 protein according to the present invention has advantages of more effectively targeting the Lrig-1 protein as compared with antibodies against Lrig-1 which are previously commercially available, and also possessing very good binding capacity thereto.

BRIEF DESCRIPTION OF DRAWINGS

FIG. 1 illustrates a structure of the Lrig-1 protein according to an embodiment of the present invention.

FIG. 2 illustrates a structure of the Lrig-1 protein according to an embodiment of the present invention.

FIG. 3 illustrates prediction results for epitopes of the Lrig-1 protein according to an embodiment of the present invention.

FIG. 4 illustrates prediction results for epitopes of the Lrig-1 protein according to an embodiment of the present invention.

FIG. 5 illustrates an expression level of Lrig-1 mRNA according to an embodiment of the present invention.

FIG. 6 illustrates an expression level of Lrig-1 mRNA according to an embodiment of the present invention.

FIG. 7 illustrates an expression level of Lrig-1 mRNA according to an embodiment of the present invention.

FIG. 8 illustrates expression levels of Lrig-1, Lrig-2, and Lrig-3 mRNAs according to an embodiment of the present invention.

FIG. 9 illustrates results obtained by comparing expression levels of Lrig-1 protein in regulatory T cells and non-regulated T cells according to an embodiment of the present invention.

FIG. 10 illustrates expression of the Lrig-1 protein on the surface of regulatory T cells according to an embodiment of the present invention.

FIG. 11 illustrates results obtained by analyzing binding capacity of Lrig-1 protein-specific monoclonal antibodies (A8, B8, D9, and H6) to the Lrig-1 protein according to an embodiment of the present invention.

FIG. 12 illustrates results obtained by analyzing the mechanism of regulating Lrig-1 protein-induced Stat3 phosphorylation, in regulatory T cells, of Lrig-1 protein-specific monoclonal antibodies (A8, B8, D9, and H6) according to an embodiment of the present invention.

FIG. 13 illustrates an experimental design for therapeutic effects, on cancer, of Lrig-1 protein-specific monoclonal antibodies (A8, B8, D9, and H6) according to an embodiment of the present invention.

FIG. 14 illustrates results obtained by analyzing therapeutic effects, on cancer, of Lrig-1 protein-specific monoclonal antibodies (A8, B8, D9, and H6) according to an embodiment of the present invention.

DETAILED DESCRIPTION OF INVENTION

According to an embodiment of the present invention, there is provided a binding molecule which specifically binds to leucine-rich and immunoglobulin-like domains 1 (Lrig-1) protein, the binding molecule comprising:

a heavy chain variable region that contains a heavy chain CDR1 consisting of an amino acid sequence selected from the group consisting of SEQ ID NOs: 5, 13, 21, and 29; a heavy chain CDR2 consisting of an amino acid sequence selected from the group consisting of SEQ ID NOs: 6, 14, 22, and 30; a heavy chain CDR3 consisting of an amino acid sequence selected from the group consisting of SEQ ID NOs: 7, 15, 23, and 31; and a light chain variable region that contains a light chain CDR1 consisting of an amino acid sequence selected from the group consisting of SEQ ID NOs: 8, 16, 24, and 32; a light chain CDR2 represented by an amino acid sequence selected from the group consisting of SEQ ID NOs: 9, 17, 25, and 33; a light chain CDR3 consisting of an amino acid sequence selected from the group consisting of SEQ ID NO: 10, 18, 26, and 34.

Hereinafter, the present invention will be described in more detail by way of examples. These examples are only for describing the present invention in more detail, and it will be apparent to those skilled in the art that according to the gist of the present invention, the scope of the present invention is not limited by these examples.

EXAMPLES

[Preparation Example 1] T Cell Subset Cell Culture

In order to identify whether the Lrig-1 protein is expressed only in regulatory T cells (Treg), the subsets of T cells, Th0, Th1, Th2, Th17, and iTreg, were prepared. The iTreg refers to cells whose differentiation has been artificially induced in a medium containing the following composition, unlike nTreg which has been naturally isolated.

The subsets of the T cells were induced to differentiate into respective cells by first isolating naive T cells obtained from the spleen of mice, causing RPMI1640 (Invitrogen Gibco, Grand Island, N.Y.) nutrient medium that contains 10% fetal bovine serum (FBS; HyClone, Logan, Utah) to further contain the respective ingredients of Table 1 below, and performing 72-hour incubation in an incubator at 37° C., 5% $CO_2$.

TABLE 1

| Differentiated cell | Composition |
| --- | --- |
| Th0 | anti-CD3, anti-CD28 |
| Th1 | IL-12, anti-IL-4 antibody |
| Th2 | IL-4, anti-IFNβ |
| Th17 | IL-6, TGFβ, anti-IFNββ, anti-IL-4 |
| iTreg | IL-2, TGFβ |

[Example 1] Structural Analysis of Lrig-1

A three-dimensional steric structure of the extracellular domain of the Lrig-1 protein was predicted to produce antibodies specific for the Lrig-1 protein, a surface protein of regulatory T cells.

First, in order to predict base sequences of epitopes (epitopes), tools of Uniprot (www.uniprot.org) and RCSB Protein Data Bank (www.rcsb.org/pdb) were used to predict a three-dimensional steric structure of the extracellular domain (ECD) of the Lrig-1 protein so that the structure of ECD is identified. Then, the results are illustrated in FIGS. 1 and 2.

As illustrated in FIG. 1, a total of 15 leucine-rich regions of LRR1 to LRR15 existed in the Lrig-LRR domain (amino acid sequence at positions 41 to 494) in the extracellular domain of the Lrig-1 protein. Each of the LRR domains is composed of 23 to 27 amino acids, with 3 to 5 leucine being present.

In addition, as illustrated in FIG. 2, three immunoglobulin-like domains exist in amino acid sequences at positions 494 to 781 of the Lrig-1 protein in the extracellular domain of the Lrig-1 protein.

[Example 2] Prediction of Lrig-1 Epitope Amino Acid Sequence

Prediction of the above base sequence was performed using Ellipro server (tools.iedb.org/ellipro/) which is an epitope prediction software based on a structure of the Lrig-1 protein. The Ellipro search engine was used because it corresponds to a search engine known to be the most reliable among the existing algorithms for predicting an epitope.

The extracellular domain analyzed in Example 1 was entered into the epitope prediction software, and then predicted contiguous or discontiguous amino acid sequences of the predicted epitopes are illustrated in FIGS. 3 and 4.

As illustrated in FIGS. 3 and 4, a total of 22 contiguous epitope amino acid sequences were predicted, and a total of 8 discontiguous epitope amino acid sequences were predicted.

[Production Examples 1 to 8] Production of Monoclonal Antibodies Specific to Lrig-1 Protein Antibodies specific for the Lrig-1 protein according to the present invention were produced. The present antibodies were not produced by specifying a certain epitope, but were produced as antibodies capable of binding to any site on the Lrig-1 protein.

In order to produce the antibodies, cells expressing the Lrig-1 protein were produced. More specifically, a DNA fragment corresponding to SEQ ID NO: 2 and pcDNA (hygro) were cleaved with a cleavage enzyme, incubated at 37° C., and ligated to produce pcDNA into which a DNA sequence of the Lrig-1 protein is inserted. The thus produced pcDNA into which SEQ ID NO: 2 is inserted was introduced, through transfection, into L cells, so that the Lrig-1 protein is allowed to be expressed on the surface of the L cells.

Light and heavy chain amino acid sequences capable of binding to Lrig-1 expressed on the cell surface were selected from the Human scFv library so that a total of eight heavy and light chains were selected.

The selected heavy and light chain amino acid sequences were fused with the mIgG2a Fc region, to produce monoclonal antibodies. The sequences of the monoclonal antibodies are shown in Table 2 below.

TABLE 2

| Classification | Clone | Location | Amino acid sequence | Sequence information |
|---|---|---|---|---|
| Production Example 1 | A7 clone | Heavy chain | METDTLLLWVLLLWVPGSTWEVQLLESGG GLVQPGGSLRLSCAASGFTFSGYDMSWVRQ APGKGLEWVSLIYPDSGNKYYADSVKGRFTI SRDNSKNTLYLQMNSLRAEDTAVYYCARDA GLSWAGAFDYWGQGTLVTVSSTTAPSVYPL APVCGDTTGSSVTLGCLVKGYFPEPVTLTW NSGSLSSGVHTFPAVLQSDLYTLSSSVTVTSS TWPSQSITCNVAHPASSTKVDKKIEPRGPTIK PCPPCKCPAPNLLGGPSVFIFPPKIKDVLMISL SPIVTCVVVDVSEDDPDVQISWFVNNVEVH TAQTQTHREDYNSTLRVVSALPIQHQDWMS GKEFKCKVNNKDLPAPIERTISKPKGSVRAP QVYVLPPPEEEMTKKQVTLTCMVTDFMPED IYVEWTNNGKTELNYKNTEPVLDSDGSYFM YSKLRVEKKNWVERNSYSCSVVHEGLHNH HTTKSFSRTPGK | SEQ ID NO: 53 |
| | | Light chain | METDTLLLWVLLLWVPGSTWQSVLTQPPSA SGTPGQRVTISCSGSSSNIGSNYVTWYQQLP GTAPKLLIYSDSHRPSGVPDRFSGSKSGTSAS LAISGLQSEDEADYYCGSWDYSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 54 |
| Production Example 2 | C8 clone | Heavy chain | METDTLLLWVLLLWVPGSTWEVQLLESGG GLVQPGGSLRLSCAASGFTFSNYYMSWVRQ APGKGLEWVSGISPGDSSTYYADSVKGRFTI SRDNSKNTLYLQMNSLRAEDTAVYYCAKGL YSNPNEPFDYWGQGTLVTVSSTTAPSVYPLA PVCGDTTGSSVTLGCLVKGYFPEPVTLTWNS GSLSSGVHTFPAVLQSDLYTLSSSVTVTSSTW PSQSITCNVAHPASSTKVDKKIEPRGPTIKPCP PCKCPAPNLLGGPSVFIFPPKIKDVLMISLSPI VTCVVVDVSEDDPDVQISWFVNNVEVHTAQ TQTHREDYNSTLRVVSALPIQHQDWMSGKE FKCKVNNKDLPAPIERTISKPKGSVRAPQVY VLPPPEEEMTKKQVTLTCMVTDFMPEDIYV EWTNNGKTELNYKNTEPVLDSDGSYFMYS KLRVEKKNWVERNSYSCSVVHEGLHNHHT TKSFSRTPGK | SEQ ID NO: 55 |
| | | Light chain | METDTLLLWVLLLWVPGSTWQSVLTQPPSA SGTPGQRVTISCTGSSSNIGSNYVSWYQQLP GTAPKLLIYDDSQRPSGVPDRFSGSKSGTSA SLAISGLRSEDEADYYCGTWDYSLNGYVFG GGTKLTVLRTVAAPTVSIFPPSSEQLTSGGAS VVCFLNNFYPKDINVKWKIDGSERQNGVLN SWTDQDSKDSTYSMSSTLTLTKDEYERHNS YTCEATHKTSTSPIVKSFNRNEC | SEQ ID NO: 56 |
| Production Example 3 | E7 clone | Heavy chain | METDTLLLWVLLLWVPGSTWEVQLLESGG GLVQPGGSLRLSCAASGFTFSSYDMSWVRQ APGKGLEWVSGISPDGSNIYYADSVKGRFTI SRDNSKNTLYLQMNSLRAEDTAVYYCAKVG LRCRYEACSYAYGMDVWGQGTLVTVSSTTA PSVYPLAPVCGDTTGSSVTLGCLVKGYFPEP | SEQ ID NO: 57 |

TABLE 2-continued

| Classification | Clone | Location | Amino acid sequence | Sequence information |
|---|---|---|---|---|
| | | | VTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | |
| | | Light chain | METDTLLLWVLLLWVPGSTWQSVLTQPPSA SGTPGQRVTISCSGSSSNIGSNYVSWYQQLP GTAPKLLIYSDSHRPSGVPDRFSGSKSGTSAS LAISGLRSEDEADYYCATWDSSLNGYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 58 |
| Production Example 4 | G3 clone | Heavy chain | METDTLLLWVLLLWVPGSTWEVQLLESGG GLVQPGGSLRLSCAASGFTFSNYDMSWVRQ APGKGLEWVSSISPSSGSIYYADSVKGRFTIS RDNSKNTLYLQMNSLRAEDTAVYYCAKDLD AFWRPSFDYWGQGTLVTVSSTTAPSVYPLA PVCGDTTGSSVTLGCLVKGYFPEPVTLTWNS GSLSSGVHTFPAVLQSDLYTLSSSVTVTSSTW PSQSITCNVAHPASSTKVDKKIEPRGPTIKPCP PCKCPAPNLLGGPSVFIFPPKIKDVLMISLSPI VTCVVVDVSEDDPDVQISWFVNNVEVHTAQ TQTHREDYNSTLRVVSALPIQHQDWMSGKE FKCKVNNKDLPAPIERTISKPKGSVRAPQVY VLPPPEEEMTKKQVTLTCMVTDFMPEDIYV EWTNNGKTELNYKNTEPVLDSDGSYFMYS KLRVEKKNWVERNSYSCSVVHEGLHNHHT TKSFSRTPGK | SEQ ID NO: 59 |
| | | Light chain | METDTLLLWVLLLWVPGSTWQSVLTQPPSA SGTPGQRVTISCTGSSSNIGNNNVNWYQQLP GTAPKLLIYSDSHRPSGVPDRFSGSKSGTSAS LAISGLRSEDEADYYCGSWDDSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 60 |
| Production Example 5 | A8 clone | Heavy chain | METDTLLLWVLLLWVPGSTWEVQLLESGG GLVQPGGSLRLSCAASGFTFSDYDMSWVRQ VPGKGLEWVSWISHGGGSIYYADSVKGRFTI SRDNSKNTLYLQMNSLRAEDTAVYYCARGL GLCKTGLCYYYDAMDVWGQGTLVTVSSTT VAPSVYPLAPVCGDTTGSSVTLGCLVKGYFPE PVTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | SEQ ID NO: 45 |
| | | Light chain | METDTLLLWVLLLWVPGSTWQSVLTQPPSA SGTPGQRVTISCTGSSSNIGNNSVTWYQQLP GTAPKLLIYADNNRPSGVPDRFSGSKSGTSA SLAISGLRSEDEADYYCAAWDSSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 46 |
| Production Example 6 | B8 clone | Heavy chain | METDTLLLWVLLLWVPGSTWEVQLLESGG GLVQPGGSLRLSCAASGFTFSDYYMSWVRQ APGKGLEWVSGISHDSGSKYYADSVKGRFTI SRDNSKNTLYLQMNSLRAEDTAVYYCARH WTTFDYWGQGTLVTVSSTTAPSVYPLAPVC GDTTGSSVTLGCLVKGYFPEPVTLTWNSGSL SSGVHTFPAVLQSDLYTLSSSVTVTSSTWPSQ SITCNVAHPASSTKVDKKIEPRGPTIKPCPPC | SEQ ID NO: 47 |

TABLE 2-continued

| Classification | Clone | Location | Amino acid sequence | Sequence information |
|---|---|---|---|---|
| | | | KCPAPNLLGGPSVFIFPPKIKDVLMISLSPIVT CVVVDVSEDDPDVQISWFVNNVEVHTAQTQ THREDYNSTLRVVSALPIQHQDWMSGKEFK CKVNNKDLPAPIERTISKPKGSVRAPQVYVL PPPEEEMTKKQVTLTCMVTDFMPEDIYVEW TNNGKTELNYKNTEPVLDSDGSYFMYSKLR VEKKNWVERNSYSCSVVHEGLHNHHTTKS FSRTPGK | |
| | | Light chain | METDTLLLWVLLLWVPGSTWQSVLTQPPSA SGTPGQRVTISCSGSSSNIGSNNVTWYQQLP GTAPKLLIYANSNRPSGVPDRFSGSKSGTSAS LAISGLRSEDEADYYCGAWDYSLSAYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 48 |
| Production Example 7 | D9 clone | Heavy chain | METDTLLLWVLLLWVPGSTWEVQLLESGG GLVQPGGSLRLSCAASGFTFSNYAMSWVRQ APGKGLEWVSAIYPGGGSIYYADSVKGRFTI SRDNSKNTLYLQMNSLRAEDTAVYYCARDI LPCPWGRCYYDYAMDVWGQGTLVTVSSTT APSVYPLAPVCGDTTGSSVTLGCLVKGYFPE PVTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | SEQ ID NO: 49 |
| | | Light chain | METDTLLLWVLLLWVPGSTWQSVLTQPPSA SGTPGQRVTISCSDSSSNIGSNTVSWYQQLP GTAPKLLIYADNNRPSGVPDRFSGSKSGTSA SLAISGLRSEDEADYYCGTWDYSLSGYVFG GGTKLTVLRTVAAPTVSIFPPSSEQLTSGGAS VVCFLNNFYPKDINVKWKIDGSERQNGVLN SWTDQDSKDSTYSMSSTLTLTKDEYERHNS YTCEATHKTSTSPIVKSFNRNEC | SEQ ID NO: 50 |
| Production Example 8 | H6 clone | Heavy chain | METDTLLLWVLLLWVPGSTWEVQLLESGG GLVQPGGSLRLSCAASGFTFSNYAMSWVRQ APGKGLEWVSVISHGGGSTYYADSVKGRFTI SRDNSKNTLYLQMNSLRAEDTAVYYCARVIS NCHLGVCYYSNGMDVWGQGTLVTVSSTTA PSVYPLAPVCGDTTGSSVTLGCLVKGYFPEP VTLTWNSGSLSSGVHTFPAVLQSDLYTLSSS VTVTSSTWPSQSITCNVAHPASSTKVDKKIEP RGPTIKPCPPCKCPAPNLLGGPSVFIFPPKIKD VLMISLSPIVTCVVVDVSEDDPDVQISWFVN NVEVHTAQTQTHREDYNSTLRVVSALPIQH QDWMSGKEFKCKVNNKDLPAPIERTISKPK GSVRAPQVYVLPPPEEEMTKKQVTLTCMVT DFMPEDIYVEWTNNGKTELNYKNTEPVLDS DGSYFMYSKLRVEKKNWVERNSYSCSVVH EGLHNHHTTKSFSRTPGK | SEQ ID NO: 51 |
| | | Light chain | METDTLLLWVLLLWVPGSTWQSVLTQPPSA SGTPGQRVTISCSGSSSNIGNNDVYWYQQLP GTAPKLLIYSDSQRPSGVPDRFSGSKSGTSAS LAISGLRSEDEADYYCGTWDYSLSGYVFGG GTKLTVLRTVAAPTVSIFPPSSEQLTSGGASV VCFLNNFYPKDINVKWKIDGSERQNGVLNS WTDQDSKDSTYSMSSTLTLTKDEYERHNSY TCEATHKTSTSPIVKSFNRNEC | SEQ ID NO: 52 |

[Example 3] Identification of Specific Expression of Lrig-1 mRNA in Regulatory T Cells Verification was made of whether the Lrig-1 protein can act as a biomarker specific for regulatory T cells.

For the verification, CD4$^+$ T cells were isolated using magnet-activated cell sorting (MACS), through CD4 beads, from the spleen of rats. Subsequently, regulatory T (CD4$^+$CD25$^+$ T) cells and non-regulatory T (CD4$^+$CD25$^-$ T) cells were isolated with a fluorescence-activated cell sorter (FACS) using a CD25 antibody. For the respective cells and the cells differentiated in Preparation Example 1, mRNA was extracted using Trizol, and gDNA was removed from genomic RNA using gDNA extraction kit (Qiagen) according to the protocol provided by the manufacturer. The gDNA-removed mRNA was synthesized into cDNA through the BDsprint cDNA Synthesis Kit (Clonetech).

Real-time polymerase chain reaction (RT PCR) was performed to quantitatively identify an expression level of Lrig-1 mRNA in the cDNA.

The real-time polymerase chain reaction was performed with primers shown in Table 3 below using SYBR Green (Molecular Probes) by the protocol provided by the manufacturer under conditions of 40 cycles consisting of 95° C. for 3 minutes, 61° C. for 15 seconds, 72° C. for 30 seconds, a relative gene expression level was calculated using the ΔΔCT method, and normalized using HPRT. The results are illustrated in FIGS. 5 to 8.

TABLE 3

| Primer | | Sequence | Sequence information |
|---|---|---|---|
| Mouse Lrig-1 | Forward | 5'-GAC GGA ATT CAG TGA GGA GAA CCT-3' | SEQ ID NO: 61 |
| | Reverse | 5'-CAA CTG GTA GTG GCA GCT TGT AGG-3' | SEQ ID NO: 62 |
| Mouse Lrig-2 | forward | 5'-TCA CAA GGA ACA TTG TCT GAA CCA-3' | SEQ ID NO: 63 |
| | reverse | 5'-GCC TGA TCT AAC ACA TCC TCC TCA-3' | SEQ ID NO: 64 |
| Mouse Lrig-3 | forward | 5'-CAG CAC CTT GAG CTG AAC AGA AAC-3' | SEQ ID NO: 65 |
| | reverse | 5'-CCA GCC TTT GGT AAT CTC GGT TAG-3' | SEQ ID NO: 66 |
| Mouse FOXP3 | forward | 5'-CTT TCA CCT ATC CCA CCC TTA TCC-3' | SEQ ID NO: 67 |
| | reverse | 5'-ATT CAT CTA CGG TCC ACA CTG CTC-3' | SEQ ID NO: 68 |
| ACTG1 | forward | 5'-GGC GTC ATG GTG GGC ATG GG-3' | SEQ ID NO: 69 |
| | reverse | 5'-ATG GCG TGG GGA AGG GCG TA-3' | SEQ ID NO: 70 |

As illustrated in FIG. 5, it can be seen that the expression of Lrig-1 in regulatory T (CD4$^+$CD25$^+$ T) cells is 18.1 times higher than non-regulatory T (CD4$^+$CD25$^-$ T) cells. This was about 10 times higher expression level than Lag3 and Ikzf4, which are previously known markers for regulatory T cells. In addition, as illustrated in FIGS. 6 and 7, the expression of Lrig-1 mRNA was remarkably high in regulatory T cells as compared with other types of immune cells, and in particular, was remarkably high in naturally isolated regulatory T cells (nTreg) as compared with induced regulatory T cells (iTreg cells).

In addition, as illustrated in FIG. 8, expression of Lrig-1 was the highest among Lrig-1, Lrig-2, and Lrig-3 which correspond to the Lrig family.

From the above results, it can be seen that the Lrig-1 protein according to the present invention is specifically expressed in regulatory T cells, in particular, naturally-occurring regulatory T cells.

[Example 4] Identification of Specific Expression of Lrig-1 Protein in Regulatory T Cells It was identified whether the Lrig-1 protein expressed from Lrig-1 mRNA is specifically expressed only in regulatory T cells.

Using FOXP3-RFP-knocked-in mice, the FOXP3-RFP obtained by coupling red fluorescence protein (RFP) to FOXP3 promoter, a transcription factor specific for regulatory T cells, CD4$^+$ T cells were isolated using magnet-activated cell sorting (MACS), through CD4 beads, from the spleen of the mice. Subsequently, using RFP protein, regulatory T (CD4$^+$RFP$^+$ T) cells and non-regulatory T (CD4$^+$RFP$^-$ T) cells were obtained by performing isolation through a fluorescence-activated cell sorter (FACS). The respective cells were stained with the purchased Lrig-1 antibody and a negative control was stained with an isotype-matched control antibody, to measure an expression level of Lrig-1 with the fluorescence-activated cell sorter. The results are illustrated in FIG. 9.

As illustrated in FIG. 9, the non-regulatory T cells indicated by a dotted line showed almost the same expression level of Lrig-1 as the negative control, whereas there were a large number of cells with high expression level of Lrig-1 in the regulatory T cells.

From the above results, it can be seen that the Lrig-1 protein according to the present invention is specifically expressed in regulatory T cells.

[Example 5] Identification of Specific Expression of Lrig-1 Protein on Surface of Regulatory T Cells From the viewpoint that in order to be a target of cell therapy, the Lrig-1 protein must be expressed on the surface of regulatory T cells, which in turn allows a more effective target therapy, it was identified whether the Lrig-1 protein is expressed on the surface of the regulatory T cells.

The respective differentiated T cell subsets of Preparation Example 1 were stained with anti-CD4-APC and anti-Lrig-1-PE antibodies, and expression levels of Lrig-1 were measured at the respective cell surfaces using a fluorescence-activated cell sorter (FACS). The results are illustrated in FIG. 10.

As illustrated in FIG. 10, Lrig-1 was expressed in an amount of 0.77 to 15.3 in activated T cells, Th1 cells, Th2 cells, Th17 cells, and naive T cells, whereas Lrig-1 was expressed as high as 83.9 in differentiation-induced T cells (iTreg cells).

From the above results, it can be seen that the Lrig-1 protein according to the present invention is not only specifically expressed in regulatory T (Treg) cells, but also is, in particular, expressed at a higher level on the surface of the Treg cells.

[Example 6] Evaluation of Binding Capacity of Antibody According to Present Invention to Lrig-1 Protein In order to identify whether the monoclonal antibodies according to the present invention produced in Production Examples 1 to 8 well recognize Lrig-1, each of the antibodies of Production Examples 1 to 8 was bound to L cells that stably express Lrig-1. Then, a secondary antibody which is conjugated with eFlour 670 and is capable of recognizing the mouse antibodies was added thereto, and then binding capacity of the monoclonal antibodies to the Lrig-1 protein was analyzed using FACS. The results are illustrated in FIG. 11.

As illustrated in FIG. 11, it was found that all Lrig-1 protein-specific monoclonal antibodies (A8, B8, D9, and H6) according to the present invention effectively recognize and bind to the Lrig-1 protein present on the surface of L cells.

[Example 7] Regulation of Signal Transduction Pathway in Treg Cells, by Antibody According to Present Invention In order to analyze how the monoclonal antibodies according to the present invention produced in Production Examples 1 to 8 affect the signal transduction pathway in Treg cells through the Lrig-1 protein, Lrig-1 present on the surface of the Treg cells was stimulated by treating the Treg cells with the antibodies of Production Examples 1 to 4, and then a level of tyrosine phosphorylation of Stat3 protein present in the stimulated Treg cells was analyzed through phosphotyrosine immunoblot. The results are illustrated in FIG. 12.

As illustrated in FIG. 12, it was found that the Lrig-1 protein-specific monoclonal antibodies (A8, B8, D9, and H6) according to the present invention continuously maintain and decrease phosphorylation of Stat3 at the same level as iTreg cells.

[Example 8] Therapeutic Effects of Antibody According to the Present Invention on Cancer In order to identify therapeutic effects of the monoclonal antibodies (A8, B8, D9, and H6) according to the present invention produced in Production Examples 5 to 8 on solid tumor, as illustrated in FIG. 13, B16F10 melanoma cells were subcutaneously injected into the dorsal area of mice in an amount of $3 \times 10^5$ cells, and then the antibodies of Production Examples 5 to 8 were intraperitoneally injected into the mice in an amount of 200 ug on days 4, 8, and 12. After transplantation of the melanoma cells, changes in tumor volume over time were measured and the results are illustrated in FIG. 14.

As illustrated in FIG. 14, it was found that remarkably decreased tumor sizes are observed in a case of being treated with the Lrig-1 protein-specific monoclonal antibodies (A8, B8, D9, and H6) according to the present invention, as compared with a negative control for which no antibody treatment has been made.

From this, it can be seen that the Lrig-1 protein-specific monoclonal antibodies according to the present invention can suppress growth of various solid tumor cells, thereby effectively preventing, ameliorating, or treating solid tumor.

Although the present invention has been described in detail above, the scope of the present invention is not limited thereto. It will be obvious to those skilled in the art that various modifications and changes can be made without departing from the technical spirit of the present invention described in the claims.

INDUSTRIAL APPLICABILITY

The present invention relates to a binding molecule capable of specifically binding to leucine-rich and immunoglobulin-like domains 1 (Lrig-1) protein, which is a protein present on the surface of regulatory T cells (Treg cells), and a use thereof, specifically, a prophylactic or therapeutic use for cancer.

Sequence List Free Text

<110>   Good T Cells, Inc.
<120>   BINDING MOLECULE SPECIFIC TO LRIG-1 PROTEIN AND USE THEREOF
<130>   DPB172433k02
<150>   KR 10-2017-0049854
<151>   2017-04-18

<160>   52
<170>   KoPatentIn 3.0

<210> 1
<211> 759
<212> PRT
<213> Homo sapiens

<400> 1

Gly Pro Arg Ala Pro Cys Ala Ala Ala Cys Thr Cys Ala Gly Asp Ser
1               5                   10                  15

Leu Asp Cys Gly Gly Arg Gly Leu Ala Ala Leu Pro Gly Asp Leu Pro
            20                  25                  30

Ser Trp Thr Arg Ser Leu Asn Leu Ser Tyr Asn Lys Leu Ser Glu Ile
        35                  40                  45

Asp Pro Ala Gly Phe Glu Asp Leu Pro Asn Leu Gln Glu Val Tyr Leu
    50                  55                  60

Asn Asn Asn Glu Leu Thr Ala Val Pro Ser Leu Gly Ala Ala Ser Ser
65                  70                  75                  80

His Val Val Ser Leu Phe Leu Gln His Asn Lys Ile Arg Ser Val Glu
                85                  90                  95

Gly Ser Gln Leu Lys Ala Tyr Leu Ser Leu Glu Val Leu Asp Leu Ser
            100                 105                 110

Leu Asn Asn Ile Thr Glu Val Arg Asn Thr Cys Phe Pro His Gly Pro
        115                 120                 125

Pro Ile Lys Glu Leu Asn Leu Ala Gly Asn Arg Ile Gly Thr Leu Glu
    130                 135                 140

Leu Gly Ala Phe Asp Gly Leu Ser Arg Ser Leu Leu Thr Leu Arg Leu
145                 150                 155                 160

Ser Lys Asn Arg Ile Thr Gln Leu Pro Val Arg Ala Phe Lys Leu Pro
                165                 170                 175

Arg Leu Thr Gln Leu Asp Leu Asn Arg Asn Arg Ile Arg Leu Ile Glu
            180                 185                 190

Gly Leu Thr Phe Gln Gly Leu Asn Ser Leu Glu Val Leu Lys Leu Gln
            195                 200                 205

Arg Asn Asn Ile Ser Lys Leu Thr Asp Gly Ala Phe Trp Gly Leu Ser
210 215 220
Lys Met His Val Leu His Leu Glu Tyr Asn Ser Leu Val Glu Val Asn
225 230 235 240
Ser Gly Ser Leu Tyr Gly Leu Thr Ala Leu His Gln Leu His Leu Ser
245 250 255
Asn Asn Ser Ile Ala Arg Ile His Arg Lys Gly Trp Ser Phe Cys Gln
260 265 270
Lys Leu His Glu Leu Val Leu Ser Phe Asn Asn Leu Thr Arg Leu Asp
275 280 285
Glu Glu Ser Leu Ala Glu Leu Ser Ser Leu Ser Val Leu Arg Leu Ser
290 295 300
His Asn Ser Ile Ser His Ile Ala Glu Gly Ala Phe Lys Gly Leu Arg
305 310 315 320
Ser Leu Arg Val Leu Asp Leu Asp His Asn Glu Ile Ser Gly Thr Ile
325 330 335
Glu Asp Thr Ser Gly Ala Phe Ser Gly Leu Asp Ser Leu Ser Lys Leu
340 345 350
Thr Leu Phe Gly Asn Lys Ile Lys Ser Val Ala Lys Arg Ala Phe Ser
355 360 365
Gly Leu Glu Gly Leu Glu His Leu Asn Leu Gly Gly Asn Ala Ile Arg
370 375 380
Ser Val Gln Phe Asp Ala Phe Val Lys Met Lys Asn Leu Lys Glu Leu
385 390 395 400
His Ile Ser Ser Asp Ser Phe Leu Cys Asp Cys Gln Leu Lys Trp Leu
405 410 415
Pro Pro Trp Leu Ile Gly Arg Met Leu Gln Ala Phe Val Thr Ala Thr
420 425 430
Cys Ala His Pro Glu Ser Leu Lys Gly Gln Ser Ile Phe Ser Val Pro
435 440 445
Pro Glu Ser Phe Val Cys Asp Asp Phe Leu Lys Pro Gln Ile Ile Thr 450                 455                 460
Gln Pro Glu Thr Thr Met Ala Met Val Gly Lys Asp Ile Arg Phe Thr
465                 470                 475                 480
Cys Ser Ala Ala Ser Ser Ser Ser Ser Pro Met Thr Phe Ala Trp Lys
                485                 490                 495
Lys Asp Asn Glu Val Leu Thr Asn Ala Asp Met Glu Asn Phe Val His
                500                 505                 510
Val His Ala Gln Asp Gly Glu Val Met Glu Tyr Thr Thr Ile Leu His
                515                 520                 525
Leu Arg Gln Val Thr Phe Gly His Glu Gly Arg Tyr Gln Cys Val Ile
                530                 535                 540
Thr Asn His Phe Gly Ser Thr Tyr Ser His Lys Ala Arg Leu Thr Val
545                 550                 555                 560
Asn Val Leu Pro Ser Phe Thr Lys Thr Pro His Asp Ile Thr Ile Arg
                565                 570                 575
Thr Thr Thr Val Ala Arg Leu Glu Cys Ala Ala Thr Gly His Pro Asn
                580                 585                 590
Pro Gln Ile Ala Trp Gln Lys Asp Gly Gly Thr Asp Phe Pro Ala Ala
                595                 600                 605
Arg Glu Arg Arg Met His Val Met Pro Asp Asp Val Phe Phe Ile
610                 615                 620
Thr Asp Val Lys Ile Asp Asp Ala Gly Val Tyr Ser Cys Thr Ala Gln
                625                 630                 635                 640
Asn Ser Ala Gly Ser Ile Ser Ala Asn Ala Thr Leu Thr Val Leu Glu
                645                 650                 655
Thr Pro Ser Leu Val Val Pro Leu Glu Asp Arg Val Val Ser Val Gly
                660                 665                 670
Glu Thr Val Ala Leu Gln Cys Lys Ala Thr Gly Asn Pro Pro Pro Arg
                675                 680                 685
Ile Thr Trp Phe Lys Gly Asp Arg Pro Leu Ser Leu Thr Glu Arg His
                690                 695                 700

His Leu Thr Pro Asp Asn Gln Leu Leu Val Val Gln Asn Val Val Ala
705 710 715 720

Glu Asp Ala Gly Arg Tyr Thr Cys Glu Met Ser Asn Thr Leu Gly Thr
            725                 730                 735

Glu Arg Ala His Ser Gln Leu Ser Val Leu Pro Ala Ala Gly Cys Arg
        740                 745                 750

Lys Asp Gly Thr Thr Val Gly
        755

<210> 2
<211> 2397
<212> DNA
<213> Homo sapiens

<400> 2

| | |
|---|---|
| ggcccgcggg cgccctgcgc ggccgcctgc acttgcgctg gggactcgct ggactgcggt | 60 |
| gggcgcgggc tggctgcgtt gcccggggac ctgccctcct ggacgcggag cctaaacctg | 120 |
| agttacaaca aactctctga gattgaccct gctggttttg aggacttgcc gaacctacag | 180 |
| gaagtgtacc tcaataataa tgagttgaca gcggtaccat ccctgggcgc tgcttcatca | 240 |
| catgtcgtct ctctctttct gcagcacaac aagattcgca gcgtggaggg gagccagctg | 300 |
| aaggcctacc tttccttaga agtgttagat ctgagtttga acaacatcac ggaagtgcgg | 360 |
| aacacctgct ttccacacgg accgcctata aaggagctca acctggcagg caatcggatt | 420 |
| ggcaccctgg agttgggagc atttgatggt ctgtcacggt cgctgctaac tcttcgcctg | 480 |
| agcaaaaaca ggatcaccca gcttcctgta agagcattca agctacccag gctgacacaa | 540 |
| ctggacctca tcggaacaga gattcggctg atagagggcc tcaccttcca ggggctcaac | 600 |
| agcttggagg tgctgaagct tcagcgaaac aacatcagca aactgacaga tgggccttc | 660 |
| tggggactgt ccaagatgca tgtgctgcac ctggagtaca cagcctggt agaagtgaac | 720 |
| agcggctcgc tctacggcct cacggccctg catcagctcc acctcagcaa caattccatc | 780 |
| gctcgcattc accgcaaggg ctggagcttc tgccagaagc tgcatgagtt ggtcctgtcc | 840 |
| ttcaacaacc tgacacggct ggacgaggag agcctggccg agctgagcag cctgagtgtc | 900 |
| ctgcgtctca gccacaattc catcagccac attgcggagg gtgccttcaa gggactcagg | 960 |
| agcctgcgag tcttggatct ggaccataac gagatttcgg gcacaataga ggacacgagc | 1020 |

| | |
|---|---:|
| ggcgccttct cagggctcga cagcctcagc aagctgactc tgtttggaaa caagatcaag | 1080 |
| tctgtggcta agagagcatt ctcggggctg gaaggcctgg agcacctgaa ccttggaggg | 1140 |
| aatgcgatca gatctgtcca gtttgatgcc tttgtgaaga tgaagaatct taaagagctc | 1200 |
| catatcagca gcgacagctt cctgtgtgac tgccagctga agtggctgcc cccgtggcta | 1260 |
| attggcagga tgctgcaggc ctttgtgaca gccacctgtg cccacccaga atcactgaag | 1320 |
| ggtcagagca ttttctctgt gccaccagag agtttcgtgt gcgatgactt cctgaagcca | 1380 |
| cagatcatca cccagccaga aaccaccatg gctatggtgg caaggacat ccggtttaca | 1440 |
| tgctcagcag ccagcagcag cagctccccc atgacctttg cctggaagaa agacaatgaa | 1500 |
| gtcctgacca atgcagacat ggagaacttt gtccacgtcc acgcgcagga cggggaagtg | 1560 |
| atggagtaca ccaccatcct gcacctccgt caggtcactt cgggcacga gggccgctac | 1620 |
| caatgtgtca tcaccaacca ctttggctcc acctattcac ataaggccag gctcaccgtg | 1680 |
| aatgtgttgc catcattcac caaaacgccc cacgacataa ccatccggac caccaccgtg | 1740 |
| gcccgcctcg aatgtgctgc cacaggtcac ccaaaccctc agattgcctg gcagaaggat | 1800 |
| ggaggcacgg atttccccgc tgcccgtgag cgacgcatgc atgtcatgcc ggatgacgac | 1860 |
| gtgttttca tcactgatgt gaaaatagat gacgcagggg tttacagctg tactgctcag | 1920 |
| aactcagccg gttctatttc agctaatgcc accctgactg tcctagagac cccatccttg | 1980 |
| gtggtcccct tggaagaccg tgtggtatct gtgggagaaa cagtggccct ccaatgcaaa | 2040 |
| gccacgggga accctccgcc ccgcatcacc tggttcaagg gggaccgccc gctgagcctc | 2100 |
| actgagcggc accctgac ccctgacaac cagctcctgg tggttcagaa cgtggtggca | 2160 |
| gaggatgcgg gccgatatac ctgtgagatg tccaacaccc tgggcacgga gcgagctcac | 2220 |
| agccagctga gcgtcctgcc cgcagcaggc tgcaggaagg atgggaccac ggtaggcatc | 2280 |
| ttcaccattg ctgtcgtgag cagcatcgtc ctgacgtcac tggtctgggt gtgcatcatc | 2340 |
| taccagacca ggaagaagag tgaagagtac agtgtcacca acacagatga aaccgtc | 2397 |

<210> 3
<211> 761
<212> PRT
<213> Mus musculus
<400> 3
Gln Ala Gly Pro Arg Ala Pro Cys Ala Ala Ala Cys Thr Cys Ala Gly
 1               5                  10                  15

Asp Ser Leu Asp Cys Ser Gly Arg Gly Leu Ala Thr Leu Pro Arg Asp
             20                  25                  30
Leu Pro Ser Trp Thr Arg Ser Leu Asn Leu Ser Tyr Asn Arg Leu Ser
             35                  40                  45
Glu Ile Asp Ser Ala Ala Phe Glu Asp Leu Thr Asn Leu Gln Glu Val
             50                  55                  60
Tyr Leu Asn Ser Asn Glu Leu Thr Ala Ile Pro Ser Leu Gly Ala Ala
  65                  70                  75                  80
Ser Ile Gly Val Val Ser Leu Phe Leu Gln His Asn Lys Ile Leu Ser
                     85                  90                  95
Val Asp Gly Ser Gln Leu Lys Ser Tyr Leu Ser Leu Glu Val Leu Asp
             100                 105                 110
Leu Ser Ser Asn Asn Ile Thr Glu Ile Arg Ser Ser Cys Phe Pro Asn
             115                 120                 125
Gly Leu Arg Ile Arg Glu Leu Asn Leu Ala Ser Asn Arg Ile Ser Ile
             130                 135                 140
Leu Glu Ser Gly Ala Phe Asp Gly Leu Ser Arg Ser Leu Leu Thr Leu
145                 150                 155                 160
Arg Leu Ser Lys Asn Arg Ile Thr Gln Leu Pro Val Lys Ala Phe Lys
             165                 170                 175
Leu Pro Arg Leu Thr Gln Leu Asp Leu Asn Arg Asn Arg Ile Arg Leu
             180                 185                 190
Ile Glu Gly Leu Thr Phe Gln Gly Leu Asp Ser Leu Glu Val Leu Arg
             195                 200                 205
Leu Gln Arg Asn Asn Ile Ser Arg Leu Thr Asp Gly Ala Phe Trp Gly
             210                 215                 220
Leu Ser Lys Met His Val Leu His Leu Glu Tyr Asn Ser Leu Val Glu
225                 230                 235                 240
Val Asn Ser Gly Ser Leu Tyr Gly Leu Thr Ala Leu His Gln Leu His
             245                 250                 255
Leu Ser Asn Asn Ser Ile Ser Arg Ile Gln Arg Asp Gly Trp Ser Phe 260                 265                 270
Cys Gln Lys Leu His Glu Leu Ile Leu Ser Phe Asn Asn Leu Thr Arg
            275                 280                 285
Leu Asp Glu Glu Ser Leu Ala Glu Leu Ser Ser Leu Ser Ile Leu Arg
        290                 295                 300
Leu Ser His Asn Ala Ile Ser His Ile Ala Glu Gly Ala Phe Lys Gly
305                 310                 315                 320
Leu Lys Ser Leu Arg Val Leu Asp Leu Asp His Asn Glu Ile Ser Gly
                325                 330                 335
Thr Ile Glu Asp Thr Ser Gly Ala Phe Thr Gly Leu Asp Asn Leu Ser
            340                 345                 350
Lys Leu Thr Leu Phe Gly Asn Lys Ile Lys Ser Val Ala Lys Arg Ala
        355                 360                 365
Phe Ser Gly Leu Glu Ser Leu Glu His Leu Asn Leu Gly Glu Asn Ala
    370                 375                 380
Ile Arg Ser Val Gln Phe Asp Ala Phe Ala Lys Met Lys Asn Leu Lys
385                 390                 395                 400
Glu Leu Tyr Ile Ser Ser Glu Ser Phe Leu Cys Asp Cys Gln Leu Lys
                405                 410                 415
Trp Leu Pro Pro Trp Leu Met Gly Arg Met Leu Gln Ala Phe Val Thr
            420                 425                 430
Ala Thr Cys Ala His Pro Glu Ser Leu Lys Gly Gln Ser Ile Phe Ser
        435                 440                 445
Val Leu Pro Asp Ser Phe Val Cys Asp Asp Phe Pro Lys Pro Gln Ile
    450                 455                 460
Ile Thr Gln Pro Glu Thr Thr Met Ala Val Val Gly Lys Asp Ile Arg
465                 470                 475                 480
Phe Thr Cys Ser Ala Ala Ser Ser Ser Ser Ser Pro Met Thr Phe Ala
                485                 490                 495
Trp Lys Lys Asp Asn Glu Val Leu Ala Asn Ala Asp Met Glu Asn Phe
            500                 505                 510

Ala His Val Arg Ala Gln Asp Gly Glu Val Met Glu Tyr Thr Thr Ile
            515                 520                 525
Leu His Leu Arg His Val Thr Phe Gly His Glu Gly Arg Tyr Gln Cys
            530                 535                 540
Ile Ile Thr Asn His Phe Gly Ser Thr Tyr Ser His Lys Ala Arg Leu
545                 550                 555                 560
Thr Val Asn Val Leu Pro Ser Phe Thr Lys Ile Pro His Asp Ile Ala
            565                 570                 575
Ile Arg Thr Gly Thr Thr Ala Arg Leu Glu Cys Ala Ala Thr Gly His
            580                 585                 590
Pro Asn Pro Gln Ile Ala Trp Gln Lys Asp Gly Gly Thr Asp Phe Pro
            595                 600                 605
Ala Ala Arg Glu Arg Arg Met His Val Met Pro Asp Asp Asp Val Phe
            610                 615                 620
Phe Ile Thr Asp Val Lys Ile Asp Asp Met Gly Val Tyr Ser Cys Thr
625                 630                 635                 640
Ala Gln Asn Ser Ala Gly Ser Val Ser Ala Asn Ala Thr Leu Thr Val
            645                 650                 655
Leu Glu Thr Pro Ser Leu Ala Val Pro Leu Glu Asp Arg Val Val Thr
            660                 665                 670
Val Gly Glu Thr Val Ala Phe Gln Cys Lys Ala Thr Gly Ser Pro Thr
            675                 680                 685
Pro Arg Ile Thr Trp Leu Lys Gly Gly Arg Pro Leu Ser Leu Thr Glu
            690                 695                 700
Arg His His Phe Thr Pro Gly Asn Gln Leu Leu Val Val Gln Asn Val
705                 710                 715                 720
Met Ile Asp Asp Ala Gly Arg Tyr Thr Cys Glu Met Ser Asn Pro Leu
            725                 730                 735
Gly Thr Glu Arg Ala His Ser Gln Leu Ser Ile Leu Pro Thr Pro Gly
            740                 745                 750
Cys Arg Lys Asp Gly Thr Thr Val Gly

<210> 4
<211> 2283
<212> DNA
<213> Mus musculus

<400> 4

```
caggctggcc cgcgggcccc ctgcgcggcc gcctgcactt gcgccgggga ctcgctggac        60
tgcagtgggc gcgggctggc gacgctgccc cgggacctgc cctcctggac gcgcagccta       120
aacctgagtt ataacagact ctccgagatc gactctgctg cttttgagga cttgacgaat       180
ctgcaggaag tgtacctcaa cagcaatgag ctgacagcca taccatcact gggcgctgct       240
tccataggag ttgtctctct cttttttgcag cacaacaaga tccttagtgt ggatgggagc     300
cagctgaagt cgtacctgtc cttggaagtg ctggatctga gttccaacaa catcacggaa       360
attcggagct cctgtttccc gaacggcctg cgtataaggg aactcaactt ggcgagcaac       420
cgcatcagca tcctggagtc tggagcattt gatggtctgt cgcggtcact gctgactctc       480
cgtctgagca aaaacaggat cacccagctt cctgtgaaag cgttcaagct acccaggctg       540
acacaactag acctgaatcg gaatcggatt cggctgattg aaggcctcac gttccagggg       600
ctcgacagct tagaggtgct gaggcttcag aggaacaaca tcagcaggct gacggacggg       660
gccttctggg ggctgtctaa gatgcacgtg ctgcacctgg agtacaacag tctggtggaa       720
gtgaacagtg gctccctcta tggcctcaca gccctgcacc agctgcacct cagcaacaac       780
tccatctctc gaattcagcg tgatggctgg agcttctgcc aaaagctgca tgagttgatt       840
ctgtccttca acaacctcac gcggctggat gaggagagtc tagcggagtt gagcagcctc       900
agtatcctgc gcctcagtca caacgccatc agtcacattg ctgaaggcgc cttcaaggga       960
ctcaagagtc tgcgggtctt ggacctggac cataacgaga tctcgggtac aatcgaggat      1020
accagtggtg cctttacggg gcttgacaac ctcagcaagc tgactctgtt tggaaacaag      1080
atcaaatctg tggctaagag agccttctcg ggcctggaaa gcctggaaca cctgaacctt      1140
ggagagaatg caatcaggtc tgtccagttt gatgcctttg caaagatgaa gaaccttaaa      1200
gagctctaca tcagcagtga gagcttcctg tgtgactgcc agctcaagtg gctgcccccca    1260
tggctaatgg gtaggatgct gcaggccttt gtgacagcca cctgtgccca tccagagtcg      1320
ctgaagggcc agagcatttt ctcagtgctg ccagacagct ttgtgtgtga tgactttcca    1380
aagccacaga tcatcaccca gcctgagacg accatggctg tggtgggcaa ggacatccgt    1440
```
ttcacatgct ccgcagccag cagcagcagc tcaccaatga ccttcgcctg gaagaaggac 1500
aatgaggtcc tggccaatgc agacatggag aactttgccc acgtccgtgc acaggacggc 1560
gaagtgatgg agtataccac tatcctgcac ctccgtcacg tcacctttgg gcacgagggc 1620
cgctaccagt gtatcatcac aaaccacttt ggctccacat actcccacaa agccaggctc 1680
actgtgaatg tgttgccatc attcactaaa atacccatg acattgccat ccggactggc 1740
accacagccc gcctcgagtg tgctgccacg ggccacccta ccctcagat tgcctggcag 1800
aaggatggag gcaccgattt cccggcagct cgtgagcgac gcatgcatgt tatgccagac 1860
gatgatgtgt tcttcatcac tgatgtgaaa atagacgaca tgggggtcta cagctgcact 1920
gcccagaact cggcaggctc ggtttcagcc aacgctaccc tcacagtctt agaaactcca 1980
tccttggcag tgcctctgga agaccgtgtg gtaactgtgg gagaaacagt ggccttccag 2040
tgcaaagcaa ccgggagccc cacaccacgc atcacctggc ttaagggagg tcgcccattg 2100
agcctcacag agcgccacca tttcactcca ggcaaccagc tgctggttgt tcagaatgtg 2160
atgatagacg atgcagggcg gtatacctgt gagatgtcta atccctggg cactgagcga 2220
gcacatagcc agctgagcat tttacctacc cctggctgcc ggaaggatgg gaccaccgta 2280
ggc
2283

<210> 5
<211> 5
<212> PRT
<213> Artificial Sequence
<220>
<223> A8 heavy chain CDR 1
<400> 5

Asp Tyr Asp Met Ser
 1               5

<210> 6
<211> 9
<212> PRT

<213> Artificial Sequence

<220>

<223> A8 heavy chain CDR 2

<400> 6

Trp Ile Ser His Gly Gly Gly Ser Ile
 1               5

<210> 7

<211> 19

<212> PRT

<213> Artificial Sequence

<220>

<223> A8 heavy chain CDR 3

<400> 7

Arg Gly Leu Gly Leu Cys Lys Thr Gly Leu Cys Tyr Tyr Tyr Asp Ala
 1               5                   10                  15

Met Asp Val

<210> 8

<211> 13

<212> PRT

<213> Artificial Sequence

<220>

<223> A8 light chain CDR 1

<400> 8

Thr Gly Ser Ser Ser Asn Ile Gly Asn Asn Ser Val Thr
 1               5                   10

<210> 9

<211> 4

<210> 9
<212> PRT
<213> Artificial Sequence
<220>
<223> A8 light chain CDR 2
<400> 9

Ala Asp Asn Asn
 1

<210> 10
<211> 9
<212> PRT
<213> Artificial Sequence
<220>
<223> A8 light chain CDR 3
<400> 10

Ala Ala Trp Asp Ser Ser Leu Ser Ala
 1               5

<210> 11
<211> 147
<212> PRT
<213> Artificial Sequence
<220>
<223> A8 heavy chain_variable region
<400> 11

Met Glu Thr Asp Thr Leu Leu Leu Trp Val Leu Leu Leu Trp Val Pro
 1               5                   10                  15
Gly Ser Thr Trp Glu Val Gln Leu Leu Glu Ser Gly Gly Gly Leu Val
             20                  25                  30
Gln Pro Gly Gly Ser Leu Arg Leu Ser Cys Ala Ala Ser Gly Phe Thr
         35                  40                  45

Phe Ser Asp Tyr Asp Met Ser Trp Val Arg Gln Val Pro Gly Lys Gly
            50                  55                  60
Leu Glu Trp Val Ser Trp Ile Ser His Gly Gly Gly Ser Ile Tyr Tyr
 65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Asn Ser Leu Arg Ala Glu Asp Thr Ala
            100                 105                 110
Val Tyr Tyr Cys Ala Arg Gly Leu Gly Leu Cys Lys Thr Gly Leu Cys
            115                 120                 125
Tyr Tyr Tyr Asp Ala Met Asp Val Trp Gly Gln Gly Thr Leu Val Thr
        130                 135                 140
Val Ser Ser
145

<210>  12
<211>  130
<212>  PRT
<213>  Artificial Sequence

<220>
<223>  A8 light chain_variable region
<400>  12
Met Glu Thr Asp Thr Leu Leu Leu Trp Val Leu Leu Leu Trp Val Pro
 1                   5                  10                  15
Gly Ser Thr Trp Gln Ser Val Leu Thr Gln Pro Pro Ser Ala Ser Gly
                 20                  25                  30
Thr Pro Gly Gln Arg Val Thr Ile Ser Cys Thr Gly Ser Ser Ser Asn
            35                  40                  45
Ile Gly Asn Asn Ser Val Thr Trp Tyr Gln Gln Leu Pro Gly Thr Ala
         50                  55                  60

Pro Lys Leu Leu Ile Tyr Ala Asp Asn Asn Arg Pro Ser Gly Val Pro
            65                  70                  75                  80
Asp Arg Phe Ser Gly Ser Lys Ser Gly Thr Ser Ala Ser Leu Ala Ile
                        85                  90                  95
Ser Gly Leu Arg Ser Glu Asp Glu Ala Asp Tyr Tyr Cys Ala Ala Trp
                    100                 105                 110
Asp Ser Ser Leu Ser Ala Tyr Val Phe Gly Gly Gly Thr Lys Leu Thr
                115                 120                 125
Val Leu
    130

<210>   13
<211>   5
<212>   PRT
<213>   Artificial Sequence
<220>
<223>   B8 heavy chain CDR 1
<400>   13

Asp Tyr Tyr Met Ser
 1               5

<210>   14
<211>   9
<212>   PRT
<213>   Artificial Sequence
<220>
<223>   B8 heavy chain CDR 2
<400>   14

Gly Ile Ser His Asp Ser Gly Ser Lys
 1               5

<210> 15
<211> 8
<212> PRT
<213> Artificial Sequence
<220>
<223> B8 heavy chain CDR 3
<400> 15

Arg His Trp Thr Thr Phe Asp Tyr
 1               5

<210> 16
<211> 13
<212> PRT
<213> Artificial Sequence
<220>
<223> B8 light chain CDR 1
<400> 16

Ser Gly Ser Ser Ser Asn Ile Gly Ser Asn Asn Val Thr
 1               5                   10

<210> 17
<211> 4
<212> PRT
<213> Artificial Sequence
<220>
<223> B8 light chain CDR 2
<400> 17

Ala Asn Ser Asn
 1

<210> 18

<211> 9
<212> PRT
<213> Artificial Sequence

<220>
<223> B8 light chain CDR 3
<400> 18
Gly Ala Trp Asp Tyr Ser Leu Ser Ala
 1               5

<210> 19
<211> 136
<212> PRT
<213> Artificial Sequence

<220>
<223> B8 heavy chain_variable region
<400> 19
Met Glu Thr Asp Thr Leu Leu Leu Trp Val Leu Leu Leu Trp Val Pro
 1               5                  10                  15
Gly Ser Thr Trp Glu Val Gln Leu Leu Glu Ser Gly Gly Gly Leu Val
                20                  25                  30
Gln Pro Gly Gly Ser Leu Arg Leu Ser Cys Ala Ala Ser Gly Phe Thr
            35                  40                  45
Phe Ser Asp Tyr Tyr Met Ser Trp Val Arg Gln Ala Pro Gly Lys Gly
        50                  55                  60
Leu Glu Trp Val Ser Gly Ile Ser His Asp Ser Gly Ser Lys Tyr Tyr
    65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Asn Ser Leu Arg Ala Glu Asp Thr Ala
               100                 105                 110

Val Tyr Tyr Cys Ala Arg His Trp Thr Thr Phe Asp Tyr Trp Gly Gln
            115                 120                 125
Gly Thr Leu Val Thr Val Ser Ser
        130                 135

<210>   20
<211>   130
<212>   PRT
<213>   Artificial Sequence
<220>
<223>   B8 light chain_variable region
<400>   20
Met Glu Thr Asp Thr Leu Leu Leu Trp Val Leu Leu Leu Trp Val Pro
  1                 5                  10                  15
Gly Ser Thr Trp Gln Ser Val Leu Thr Gln Pro Pro Ser Ala Ser Gly
            20                  25                  30
Thr Pro Gly Gln Arg Val Thr Ile Ser Cys Ser Gly Ser Ser Ser Asn
        35                  40                  45
Ile Gly Ser Asn Asn Val Thr Trp Tyr Gln Gln Leu Pro Gly Thr Ala
    50                  55                  60
Pro Lys Leu Leu Ile Tyr Ala Asn Ser Asn Arg Pro Ser Gly Val Pro
 65                  70                  75                  80
Asp Arg Phe Ser Gly Ser Lys Ser Gly Thr Ser Ala Ser Leu Ala Ile
                85                  90                  95
Ser Gly Leu Arg Ser Glu Asp Glu Ala Asp Tyr Tyr Cys Gly Ala Trp
            100                 105                 110
Asp Tyr Ser Leu Ser Ala Tyr Val Phe Gly Gly Gly Thr Lys Leu Thr
        115                 120                 125
Val Leu
    130

<210> 21
<211> 5
<212> PRT
<213> Artificial Sequence
<220>
<223> D9 heavy chain CDR 1
<400> 21

Asn Tyr Ala Met Ser
 1               5

<210> 22
<211> 9
<212> PRT
<213> Artificial Sequence
<220>
<223> D9 heavy chain CDR 2
<400> 22

Ala Ile Tyr Pro Gly Gly Gly Ser Ile
 1               5

<210> 23
<211> 19
<212> PRT
<213> Artificial Sequence
<220>
<223> D9 heavy chain CDR 3
<400> 23

Arg Asp Ile Leu Pro Cys Pro Trp Gly Arg Cys Tyr Tyr Asp Tyr Ala
 1               5                  10                  15
Met Asp Val

<210> 24
<211> 13
<212> PRT
<213> Artificial Sequence
<220>
<223> D9 light chain CDR 1
<400> 24

Ser Asp Ser Ser Ser Asn Ile Gly Ser Asn Thr Val Ser
1               5                   10

<210> 25
<211> 4
<212> PRT
<213> Artificial Sequence
<220>
<223> D9 light chain CDR 2
<400> 25

Ala Asp Asn Asn
1

<210> 26
<211> 9
<212> PRT
<213> Artificial Sequence
<220>
<223> D9 light chain CDR 3
<400> 26

Gly Thr Trp Asp Tyr Ser Leu Ser Gly
1               5

<210> 27
<211> 147
<212> PRT
<213> Artificial Sequence
<220>
<223> D9 heavy chain_variable region
<400> 27

Met Glu Thr Asp Thr Leu Leu Leu Trp Val Leu Leu Leu Trp Val Pro
1               5                   10                  15
Gly Ser Thr Trp Glu Val Gln Leu Leu Glu Ser Gly Gly Gly Leu Val
            20                  25                  30
Gln Pro Gly Gly Ser Leu Arg Leu Ser Cys Ala Ala Ser Gly Phe Thr
        35                  40                  45
Phe Ser Asn Tyr Ala Met Ser Trp Val Arg Gln Ala Pro Gly Lys Gly
    50                  55                  60
Leu Glu Trp Val Ser Ala Ile Tyr Pro Gly Gly Gly Ser Ile Tyr Tyr
65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Asn Ser Leu Arg Ala Glu Asp Thr Ala
            100                 105                 110
Val Tyr Tyr Cys Ala Arg Asp Ile Leu Pro Cys Pro Trp Gly Arg Cys
        115                 120                 125
Tyr Tyr Asp Tyr Ala Met Asp Val Trp Gly Gln Gly Thr Leu Val Thr
    130                 135                 140
Val Ser Ser
145

<210> 28
<211> 130

<212> PRT
<213> Artificial Sequence
<220>
<223> D9 light chain_variable region
<400> 28

Met Glu Thr Asp Thr Leu Leu Leu Trp Val Leu Leu Leu Trp Val Pro
 1               5                  10                  15
Gly Ser Thr Trp Gln Ser Val Leu Thr Gln Pro Pro Ser Ala Ser Gly
            20                  25                  30
Thr Pro Gly Gln Arg Val Thr Ile Ser Cys Ser Asp Ser Ser Ser Asn
        35                  40                  45
Ile Gly Ser Asn Thr Val Ser Trp Tyr Gln Gln Leu Pro Gly Thr Ala
    50                  55                  60
Pro Lys Leu Leu Ile Tyr Ala Asp Asn Asn Arg Pro Ser Gly Val Pro
 65                  70                  75                  80
Asp Arg Phe Ser Gly Ser Lys Ser Gly Thr Ser Ala Ser Leu Ala Ile
                85                  90                  95
Ser Gly Leu Arg Ser Glu Asp Glu Ala Asp Tyr Tyr Cys Gly Thr Trp
            100                 105                 110
Asp Tyr Ser Leu Ser Gly Tyr Val Phe Gly Gly Gly Thr Lys Leu Thr
        115                 120                 125
Val Leu
    130

<210> 29
<211> 5
<212> PRT
<213> Artificial Sequence
<220>
<223> H6 heavy chain CDR 1
<400> 29

Asn Tyr Ala Met Ser
 1               5

<210> 30
<211> 9
<212> PRT
<213> Artificial Sequence
<220>
<223> H6 heavy chain CDR 2
<400> 30

Val Ile Ser His Gly Gly Gly Ser Thr
 1               5

<210> 31
<211> 19
<212> PRT
<213> Artificial Sequence
<220>
<223> H6 heavy chain CDR 3
<400> 31

Arg Val Ile Ser Asn Cys His Leu Gly Val Cys Tyr Tyr Ser Asn Gly
 1               5                   10                  15
Met Asp Val

<210> 32
<211> 13
<212> PRT
<213> Artificial Sequence
<220>
<223> H6 light chain CDR 1

<400> 32

Ser Gly Ser Ser Ser Asn Ile Gly Asn Asn Asp Val Tyr
1               5                   10

<210> 33
<211> 4
<212> PRT
<213> Artificial Sequence
<220>
<223> H6 light chain CDR 2

<400> 33

Ser Asp Ser Gln
1

<210> 34
<211> 9
<212> PRT
<213> Artificial Sequence
<220>
<223> H6 light chain CDR 3
<400> 34

Gly Thr Trp Asp Tyr Ser Leu Ser Gly
1               5

<210> 35
<211> 147
<212> PRT
<213> Artificial Sequence
<220>
<223> H6 heavy chain_variable region

<400> 35

Met Glu Thr Asp Thr Leu Leu Leu Trp Val Leu Leu Leu Trp Val Pro
 1               5                  10                 15
Gly Ser Thr Trp Glu Val Gln Leu Leu Glu Ser Gly Gly Gly Leu Val
                20                  25                 30
Gln Pro Gly Gly Ser Leu Arg Leu Ser Cys Ala Ala Ser Gly Phe Thr
             35                  40                 45
Phe Ser Asn Tyr Ala Met Ser Trp Val Arg Gln Ala Pro Gly Lys Gly
          50                  55                 60
Leu Glu Trp Val Ser Val Ile Ser His Gly Gly Gly Ser Thr Tyr Tyr
 65                  70                  75                 80
Ala Asp Ser Val Lys Gly Arg Phe Thr Ile Ser Arg Asp Asn Ser Lys
             85                  90                 95
Asn Thr Leu Tyr Leu Gln Met Asn Ser Leu Arg Ala Glu Asp Thr Ala
            100                 105                110
Val Tyr Tyr Cys Ala Arg Val Ile Ser Asn Cys His Leu Gly Val Cys
            115                 120                125
Tyr Tyr Ser Asn Gly Met Asp Val Trp Gly Gln Gly Thr Leu Val Thr
          130                 135                140
Val Ser Ser
145

<210> 36
<211> 130
<212> PRT
<213> Artificial Sequence
<220>
<223> H6 light chain_variable region
<400> 36

Met Glu Thr Asp Thr Leu Leu Leu Trp Val Leu Leu Leu Trp Val Pro

```
            1               5              10              15
Gly Ser Thr Trp Gln Ser Val Leu Thr Gln Pro Pro Ser Ala Ser Gly
                   20              25              30
Thr Pro Gly Gln Arg Val Thr Ile Ser Cys Ser Gly Ser Ser Ser Asn
                   35              40              45
Ile Gly Asn Asn Asp Val Tyr Trp Tyr Gln Gln Leu Pro Gly Thr Ala
           50              55              60
Pro Lys Leu Leu Ile Tyr Ser Asp Ser Gln Arg Pro Ser Gly Val Pro
   65              70              75              80
Asp Arg Phe Ser Gly Ser Lys Ser Gly Thr Ser Ala Ser Leu Ala Ile
                   85              90              95
Ser Gly Leu Arg Ser Glu Asp Glu Ala Asp Tyr Tyr Cys Gly Thr Trp
                  100             105             110
Asp Tyr Ser Leu Ser Gly Tyr Val Phe Gly Gly Gly Thr Lys Leu Thr
              115             120             125
Val Leu
       130

<210>   37
<211>   328
<212>   PRT
<213>   Mus musculus
<400>   37
Thr Thr Ala Pro Ser Val Tyr Pro Leu Ala Pro Val Cys Gly Asp Thr
    1               5              10              15
Thr Gly Ser Ser Val Thr Leu Gly Cys Leu Val Lys Gly Tyr Phe Pro
                   20              25              30
Glu Pro Val Thr Leu Thr Trp Asn Ser Gly Ser Leu Ser Ser Gly Val
                   35              40              45
His Thr Phe Pro Ala Val Leu Gln Ser Asp Leu Tyr Thr Leu Ser Ser
           50              55              60
```

Ser Val Thr Val Thr Ser Ser Thr Trp Pro Ser Gln Ser Ile Thr Cys
 65                  70                  75                  80
Asn Val Ala His Pro Ala Ser Ser Thr Lys Val Asp Lys Lys Ile Glu
                85                  90                  95
Pro Arg Gly Pro Thr Ile Lys Pro Cys Pro Pro Cys Lys Cys Pro Ala
                100                 105                 110
Pro Asn Leu Leu Gly Gly Pro Ser Val Phe Ile Phe Pro Pro Lys Ile
                115                 120                 125
Lys Asp Val Leu Met Ile Ser Leu Ser Pro Ile Val Thr Cys Val Val
                130                 135                 140
Val Asp Val Ser Glu Asp Asp Pro Asp Val Gln Ile Ser Trp Phe Val
145                 150                 155                 160
Asn Asn Val Glu Val His Thr Ala Gln Thr Gln Thr His Arg Glu Asp
                165                 170                 175
Tyr Asn Ser Thr Leu Arg Val Val Ser Ala Leu Pro Ile Gln His Gln
                180                 185                 190
Asp Trp Met Ser Gly Lys Glu Phe Lys Cys Lys Val Asn Asn Lys Asp
                195                 200                 205
Leu Pro Ala Pro Ile Glu Arg Thr Ile Ser Lys Pro Lys Gly Ser Val
                210                 215                 220
Arg Ala Pro Gln Val Tyr Val Leu Pro Pro Pro Glu Glu Glu Met Thr
225                 230                 235                 240
Lys Lys Gln Val Thr Leu Thr Cys Met Val Thr Asp Phe Met Pro Glu
                245                 250                 255
Asp Ile Tyr Val Glu Trp Thr Asn Asn Gly Lys Thr Glu Leu Asn Tyr
                260                 265                 270
Lys Asn Thr Glu Pro Val Leu Asp Ser Asp Gly Ser Tyr Phe Met Tyr
                275                 280                 285
Ser Lys Leu Arg Val Glu Lys Lys Asn Trp Val Glu Arg Asn Ser Tyr
                290                 295                 300
Ser Cys Ser Val Val His Glu Gly Leu His Asn His His Thr Thr Lys

<210> 38
<211> 107
<212> PRT
<213> Mus musculus
<400> 38

Arg Thr Val Ala Ala Pro Thr Val Ser Ile Phe Pro Pro Ser Ser Glu
 1               5                  10                  15
Gln Leu Thr Ser Gly Gly Ala Ser Val Val Cys Phe Leu Asn Asn Phe
            20                  25                  30
Tyr Pro Lys Asp Ile Asn Val Lys Trp Lys Ile Asp Gly Ser Glu Arg
        35                  40                  45
Gln Asn Gly Val Leu Asn Ser Trp Thr Asp Gln Asp Ser Lys Asp Ser
    50                  55                  60
Thr Tyr Ser Met Ser Ser Thr Leu Thr Leu Thr Lys Asp Glu Tyr Glu
 65                  70                  75                  80
Arg His Asn Ser Tyr Thr Cys Glu Ala Thr His Lys Thr Ser Thr Ser
                85                  90                  95
Pro Ile Val Lys Ser Phe Asn Arg Asn Glu Cys
            100                 105

<210> 39
<211> 330
<212> PRT
<213> Homo sapiens
<400> 39

Ala Ser Thr Lys Gly Pro Ser Val Phe Pro Leu Ala Pro Ser Ser Lys
 1               5                  10                  15

Ser Phe Ser Arg Thr Pro Gly Lys
            325

Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
 65                 70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn

Asn Tyr Lys Thr Thr Pro Pro Val Leu Asp Ser Asp Gly Ser Phe Phe
          260                 265                 270
Leu Tyr Ser Lys Leu Thr Val Asp Lys Ser Arg Trp Gln Gln Gly Asn
      275                 280                 285
Val Phe Ser Cys Ser Val Met His Glu Ala Leu His Asn His Tyr Thr
  290                 295                 300
Gln Lys Ser Leu Ser Leu Ser Pro Gly Lys
305                 310                 315                 320
          325                 330

<210> 40
<211> 107
<212> PRT
<213> Homo sapiens
<400> 40

Arg Thr Val Ala Ala Pro Ser Val Phe Ile Phe Pro Pro Ser Asp Glu
  1               5                   10                  15
Gln Leu Lys Ser Gly Thr Ala Ser Val Val Cys Leu Leu Asn Asn Phe
          20                  25                  30
Tyr Pro Arg Glu Ala Lys Val Gln Trp Lys Val Asp Asn Ala Leu Gln
      35                  40                  45
Ser Gly Asn Ser Gln Glu Ser Val Thr Glu Gln Asp Ser Lys Asp Ser
  50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
          85                  90                  95
Pro Val Thr Lys Ser Phe Asn Arg Gly Glu Cys
          100                 105

<210> 41

<211> 326
<212> PRT
<213> Homo sapiens
<400> 41

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Asn Phe Gly Thr Gln Thr
 65                 70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu 210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                    245                 250                 255
Ser Val Glu Trp Glu Ser Asn Gly Gln Pro Glu Asn Asn Tyr Lys Thr
                260                 265                 270
Thr Pro Pro Met Leu Asp Ser Asp Gly Ser Phe Phe Leu Tyr Ser Lys
                275                 280                 285
Leu Thr Val Asp Lys Ser Arg Trp Gln Gln Gly Asn Val Phe Ser Cys
            290                 295                 300
Ser Val Met His Glu Ala Leu His Asn His Tyr Thr Gln Lys Ser Leu
305                 310                 315                 320
Ser Leu Ser Pro Gly Lys
                325

<210>   42
<211>   377
<212>   PRT
<213>   Homo sapiens
<400>   42
Ala Ser Thr Lys Gly Pro Ser Val Phe Pro Leu Ala Pro Cys Ser Arg
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
            85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
            115                 120                 125
Cys Pro Glu Pro Lys Ser Cys Asp Thr Pro Pro Pro Cys Pro Arg Cys
            130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
            165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
            195                 200                 205
Val Asp Gly Val Glu Val His Asn Ala Lys Thr Lys Pro Arg Glu Glu
            210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
            245                 250                 255
Ala Leu Pro Ala Pro Ile Glu Lys Thr Ile Ser Lys Thr Lys Gly Gln
            260                 265                 270
Pro Arg Glu Pro Gln Val Tyr Thr Leu Pro Pro Ser Arg Glu Glu Met
            275                 280                 285
Thr Lys Asn Gln Val Ser Leu Thr Cys Leu Val Lys Gly Phe Tyr Pro
            290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu

Tyr Ser Lys Leu Thr Val Asp Lys Ser Arg Trp Gln Gln Gly Asn Ile
            325                 330                 335

Phe Ser Cys Ser Val Met His Glu Ala Leu His Asn Arg Phe Thr Gln
            340                 345                 350

Lys Ser Leu Ser Leu Ser Pro Gly Lys
            355                 360                 365

<210> 43

<211> 327

<212> PRT

<213> Homo sapiens

<400> 43

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
        325

<210>   44
<211>   245
<212>   PRT
<213>   Artificial Sequence
<220>
<223>   Hybrid Fc_Heavy region

<400> 44

Arg Asn Thr Gly Arg Gly Gly Glu Glu Lys Lys Lys Glu Lys Glu Lys
1               5                   10                  15
Glu Glu Gln Glu Glu Arg Glu Thr Lys Thr Pro Glu Cys Pro Ser His
                20                  25                  30
Thr Gln Pro Leu Gly Val Phe Leu Phe Pro Pro Lys Pro Lys Asp Thr
                35                  40                  45
Leu Met Ile Ser Arg Thr Pro Glu Val Thr Cys Val Val Val Asp Val
                50                  55                  60
Ser Gln Glu Asp Pro Glu Val Gln Phe Asn Trp Tyr Val Asp Gly Val
 65                 70                  75                  80
Glu Val His Asn Ala Lys Thr Lys Pro Arg Glu Glu Gln Phe Asn Ser
                85                  90                  95
Thr Tyr Arg Val Val Ser Val Leu Thr Val Leu His Gln Asp Trp Leu
                100                 105                 110
Asn Gly Lys Glu Tyr Lys Cys Lys Val Ser Asn Lys Gly Leu Pro Ser
                115                 120                 125
Ser Ile Glu Lys Thr Ile Ser Lys Ala Lys Gly Gln Pro Arg Glu Pro
                130                 135                 140
Gln Val Tyr Thr Leu Pro Pro Ser Gln Glu Glu Met Thr Lys Asn Gln
145                 150                 155                 160
Val Ser Leu Thr Cys Leu Val Lys Gly Phe Tyr Pro Ser Asp Ile Ala
                165                 170                 175
Val Glu Trp Glu Ser Asn Gly Gln Pro Glu Asn Asn Tyr Lys Thr Thr
                180                 185                 190
Pro Pro Val Leu Asp Ser Asp Gly Ser Phe Phe Leu Tyr Ser Arg Leu
                195                 200                 205
Thr Val Asp Lys Ser Arg Trp Gln Glu Gly Asn Val Phe Ser Cys Ser
                210                 215                 220
Val Met His Glu Ala Leu His Asn His Tyr Thr Gln Lys Ser Leu Ser
225                 230                 235                 240

Leu Ser Leu Gly Lys
        245

<210> 45
<211> 475
<212> PRT
<213> Artificial Sequence
<220>
<223> A8 heavy chain_mouse IgG2 Fc_full sequence
<400> 45

Met Glu Thr Asp Thr Leu Leu Leu Trp Val Leu Leu Leu Trp Val Pro
 1              5              10             15
Gly Ser Thr Trp Glu Val Gln Leu Leu Glu Ser Gly Gly Gly Leu Val
             20             25             30
Gln Pro Gly Gly Ser Leu Arg Leu Ser Cys Ala Ala Ser Gly Phe Thr
        35              40              45
Phe Ser Asp Tyr Asp Met Ser Trp Val Arg Gln Val Pro Gly Lys Gly
     50             55             60
Leu Glu Trp Val Ser Trp Ile Ser His Gly Gly Gly Ser Ile Tyr Tyr
 65             70             75            80
Ala Asp Ser Val Lys Gly Arg Phe Thr Ile Ser Arg Asp Asn Ser Lys
             85             90            95
Asn Thr Leu Tyr Leu Gln Met Asn Ser Leu Arg Ala Glu Asp Thr Ala
        100            105           110
Val Tyr Tyr Cys Ala Arg Gly Leu Gly Leu Cys Lys Thr Gly Leu Cys
        115            120           125
Tyr Tyr Tyr Asp Ala Met Asp Val Trp Gly Gln Gly Thr Leu Val Thr
    130            135           140
Val Ser Ser Thr Thr Ala Pro Ser Val Tyr Pro Leu Ala Pro Val Cys
145             150            155           160
Gly Asp Thr Thr Gly Ser Ser Val Thr Leu Gly Cys Leu Val Lys Gly

|     |     |     |     |     |
| --- | --- | --- | --- | --- |
|     | 165 |     | 170 |     | 175 |

Tyr Phe Pro Glu Pro Val Thr Leu Thr Trp Asn Ser Gly Ser Leu Ser
                180              185              190
Ser Gly Val His Thr Phe Pro Ala Val Leu Gln Ser Asp Leu Tyr Thr
                195              200              205
Leu Ser Ser Ser Val Thr Val Thr Ser Ser Thr Trp Pro Ser Gln Ser
        210              215              220
Ile Thr Cys Asn Val Ala His Pro Ala Ser Ser Thr Lys Val Asp Lys
225              230              235              240
Lys Ile Glu Pro Arg Gly Pro Thr Ile Lys Pro Cys Pro Pro Cys Lys
                    245              250              255
Cys Pro Ala Pro Asn Leu Leu Gly Gly Pro Ser Val Phe Ile Phe Pro
                260              265              270
Pro Lys Ile Lys Asp Val Leu Met Ile Ser Leu Ser Pro Ile Val Thr
                275              280              285
Cys Val Val Val Asp Val Ser Glu Asp Asp Pro Asp Val Gln Ile Ser
            290              295              300
Trp Phe Val Asn Asn Val Glu Val His Thr Ala Gln Thr Gln Thr His
305              310              315              320
Arg Glu Asp Tyr Asn Ser Thr Leu Arg Val Val Ser Ala Leu Pro Ile
                325              330              335
Gln His Gln Asp Trp Met Ser Gly Lys Glu Phe Lys Cys Lys Val Asn
                340              345              350
Asn Lys Asp Leu Pro Ala Pro Ile Glu Arg Thr Ile Ser Lys Pro Lys
            355              360              365
Gly Ser Val Arg Ala Pro Gln Val Tyr Val Leu Pro Pro Pro Glu Glu
        370              375              380
Glu Met Thr Lys Lys Gln Val Thr Leu Thr Cys Met Val Thr Asp Phe
385              390              395              400
Met Pro Glu Asp Ile Tyr Val Glu Trp Thr Asn Asn Gly Lys Thr Glu
            405              410              415

Leu Asn Tyr Lys Asn Thr Glu Pro Val Leu Asp Ser Asp Gly Ser Tyr
     420     425     430

Phe Met Tyr Ser Lys Leu Arg Val Glu Lys Lys Asn Trp Val Glu Arg
     435     440     445

Asn Ser Tyr Ser Cys Ser Val Val His Glu Gly Leu His Asn His His
   450     455     460

Thr Thr Lys Ser Phe Ser Arg Thr Pro Gly Lys
465     470     475

<210> 46
<211> 237
<212> PRT
<213> Artificial Sequence
<220>
<223> A8 light chain_mouse IgG2 Fc_full sequence
<400> 46

Met Glu Thr Asp Thr Leu Leu Leu Trp Val Leu Leu Leu Trp Val Pro
 1     5     10     15

Gly Ser Thr Trp Gln Ser Val Leu Thr Gln Pro Pro Ser Ala Ser Gly
     20     25     30

Thr Pro Gly Gln Arg Val Thr Ile Ser Cys Thr Gly Ser Ser Ser Asn
   35     40     45

Ile Gly Asn Asn Ser Val Thr Trp Tyr Gln Gln Leu Pro Gly Thr Ala
  50     55     60

Pro Lys Leu Leu Ile Tyr Ala Asp Asn Asn Arg Pro Ser Gly Val Pro
65     70     75     80

Asp Arg Phe Ser Gly Ser Lys Ser Gly Thr Ser Ala Ser Leu Ala Ile
     85     90     95

Ser Gly Leu Arg Ser Glu Asp Glu Ala Asp Tyr Tyr Cys Ala Ala Trp
    100     105     110

Asp Ser Ser Leu Ser Ala Tyr Val Phe Gly Gly Gly Thr Lys Leu Thr
            115                 120                 125
Val Leu Arg Thr Val Ala Ala Pro Thr Val Ser Ile Phe Pro Pro Ser
            130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
            165                 170                 175
Glu Arg Gln Asn Gly Val Leu Asn Ser Trp Thr Asp Gln Asp Ser Lys
            180                 185                 190
Asp Ser Thr Tyr Ser Met Ser Ser Thr Leu Thr Leu Thr Lys Asp Glu
            195                 200                 205
Tyr Glu Arg His Asn Ser Tyr Thr Cys Glu Ala Thr His Lys Thr Ser
            210                 215                 220
Thr Ser Pro Ile Val Lys Ser Phe Asn Arg Asn Glu Cys
225                 230                 235

<210> 47
<211> 464
<212> PRT
<213> Artificial Sequence
<220>
<223> B8 heavy chain_mouse IgG2 Fc_full sequence
<400> 47

Met Glu Thr Asp Thr Leu Leu Leu Trp Val Leu Leu Leu Trp Val Pro
1               5                   10                  15
Gly Ser Thr Trp Glu Val Gln Leu Leu Glu Ser Gly Gly Gly Leu Val
            20                  25                  30
Gln Pro Gly Gly Ser Leu Arg Leu Ser Cys Ala Ala Ser Gly Phe Thr
            35                  40                  45
Phe Ser Asp Tyr Tyr Met Ser Trp Val Arg Gln Ala Pro Gly Lys Gly

```
              50                  55                  60
Leu Glu Trp Val Ser Gly Ile Ser His Asp Ser Gly Ser Lys Tyr Tyr
              65                  70                  75              80
Ala Asp Ser Val Lys Gly Arg Phe Thr Ile Ser Arg Asp Asn Ser Lys
                      85                  90                  95
Asn Thr Leu Tyr Leu Gln Met Asn Ser Leu Arg Ala Glu Asp Thr Ala
                      100                 105                 110
Val Tyr Tyr Cys Ala Arg His Trp Thr Thr Phe Asp Tyr Trp Gly Gln
              115                 120                 125
Gly Thr Leu Val Thr Val Ser Ser Thr Thr Ala Pro Ser Val Tyr Pro
              130                 135                 140
Leu Ala Pro Val Cys Gly Asp Thr Thr Gly Ser Ser Val Thr Leu Gly
145                 150                 155                 160
Cys Leu Val Lys Gly Tyr Phe Pro Glu Pro Val Thr Leu Thr Trp Asn
                      165                 170                 175
Ser Gly Ser Leu Ser Ser Gly Val His Thr Phe Pro Ala Val Leu Gln
                      180                 185                 190
Ser Asp Leu Tyr Thr Leu Ser Ser Ser Val Thr Val Thr Ser Ser Thr
              195                 200                 205
Trp Pro Ser Gln Ser Ile Thr Cys Asn Val Ala His Pro Ala Ser Ser
              210                 215                 220
Thr Lys Val Asp Lys Lys Ile Glu Pro Arg Gly Pro Thr Ile Lys Pro
225                 230                 235                 240
Cys Pro Pro Cys Lys Cys Pro Ala Pro Asn Leu Leu Gly Gly Pro Ser
                      245                 250                 255
Val Phe Ile Phe Pro Pro Lys Ile Lys Asp Val Leu Met Ile Ser Leu
                      260                 265                 270
Ser Pro Ile Val Thr Cys Val Val Val Asp Val Ser Glu Asp Asp Pro
              275                 280                 285
Asp Val Gln Ile Ser Trp Phe Val Asn Asn Val Glu Val His Thr Ala
              290                 295                 300
```

Gln Thr Gln Thr His Arg Glu Asp Tyr Asn Ser Thr Leu Arg Val Val
305 310 315 320
Ser Ala Leu Pro Ile Gln His Gln Asp Trp Met Ser Gly Lys Glu Phe
325 330 335
Lys Cys Lys Val Asn Asn Lys Asp Leu Pro Ala Pro Ile Glu Arg Thr
340 345 350
Ile Ser Lys Pro Lys Gly Ser Val Arg Ala Pro Gln Val Tyr Val Leu
355 360 365
Pro Pro Pro Glu Glu Glu Met Thr Lys Lys Gln Val Thr Leu Thr Cys
370 375 380
Met Val Thr Asp Phe Met Pro Glu Asp Ile Tyr Val Glu Trp Thr Asn
385 390 395 400
Asn Gly Lys Thr Glu Leu Asn Tyr Lys Asn Thr Glu Pro Val Leu Asp
405 410 415
Ser Asp Gly Ser Tyr Phe Met Tyr Ser Lys Leu Arg Val Glu Lys Lys
420 425 430
Asn Trp Val Glu Arg Asn Ser Tyr Ser Cys Ser Val Val His Glu Gly
435 440 445
Leu His Asn His His Thr Thr Lys Ser Phe Ser Arg Thr Pro Gly Lys
450 455 460

<210> 48
<211> 237
<212> PRT
<213> Artificial Sequence
<220>
<223> B8 light chain_mouse IgG2 Fc_full sequence
<400> 48
Met Glu Thr Asp Thr Leu Leu Leu Trp Val Leu Leu Leu Trp Val Pro
1 5 10 15
Gly Ser Thr Trp Gln Ser Val Leu Thr Gln Pro Pro Ser Ala Ser Gly

|                   |                   | 20                |                   |                   |                   | 25                |                   |                   |                   | 30                |
|-------------------|-------------------|-------------------|-------------------|-------------------|-------------------|-------------------|-------------------|-------------------|-------------------|-------------------|

Thr Pro Gly Gln Arg Val Thr Ile Ser Cys Ser Gly Ser Ser Ser Asn 35        40       45

Ile Gly Ser Asn Asn Val Thr Trp Tyr Gln Gln Leu Pro Gly Thr Ala 50        55       60

Pro Lys Leu Leu Ile Tyr Ala Asn Ser Asn Arg Pro Ser Gly Val Pro 65       70       75       80

Asp Arg Phe Ser Gly Ser Lys Ser Gly Thr Ser Ala Ser Leu Ala Ile 85        90       95

Ser Gly Leu Arg Ser Glu Asp Glu Ala Asp Tyr Tyr Cys Gly Ala Trp 100       105      110

Asp Tyr Ser Leu Ser Ala Tyr Val Phe Gly Gly Gly Thr Lys Leu Thr 115       120      125

Val Leu Arg Thr Val Ala Ala Pro Thr Val Ser Ile Phe Pro Pro Ser 130       135       140

Ser Glu Gln Leu Thr Ser Gly Gly Ala Ser Val Val Cys Phe Leu Asn 145       150       155       160

Asn Phe Tyr Pro Lys Asp Ile Asn Val Lys Trp Lys Ile Asp Gly Ser 165       170      175

Glu Arg Gln Asn Gly Val Leu Asn Ser Trp Thr Asp Gln Asp Ser Lys 180       185      190

Asp Ser Thr Tyr Ser Met Ser Ser Thr Leu Thr Leu Thr Lys Asp Glu 195       200      205

Tyr Glu Arg His Asn Ser Tyr Thr Cys Glu Ala Thr His Lys Thr Ser 210       215       220

Thr Ser Pro Ile Val Lys Ser Phe Asn Arg Asn Glu Cys 225       230       235

<210> 49
<211> 475
<212> PRT

<213>   Artificial Sequence
<220>
<223>   D9 heavy chain_mouse IgG2 Fc_full sequence
<400>   49

Met Glu Thr Asp Thr Leu Leu Leu Trp Val Leu Leu Leu Trp Val Pro
 1               5                  10                  15
Gly Ser Thr Trp Glu Val Gln Leu Leu Glu Ser Gly Gly Gly Leu Val
            20                  25                  30
Gln Pro Gly Gly Ser Leu Arg Leu Ser Cys Ala Ala Ser Gly Phe Thr
        35                  40                  45
Phe Ser Asn Tyr Ala Met Ser Trp Val Arg Gln Ala Pro Gly Lys Gly
     50                  55                  60
Leu Glu Trp Val Ser Ala Ile Tyr Pro Gly Gly Gly Ser Ile Tyr Tyr
 65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Asn Ser Leu Arg Ala Glu Asp Thr Ala
            100                 105                 110
Val Tyr Tyr Cys Ala Arg Asp Ile Leu Pro Cys Pro Trp Gly Arg Cys
        115                 120                 125
Tyr Tyr Asp Tyr Ala Met Asp Val Trp Gly Gln Gly Thr Leu Val Thr
    130                 135                 140
Val Ser Ser Thr Thr Ala Pro Ser Val Tyr Pro Leu Ala Pro Val Cys
145                 150                 155                 160
Gly Asp Thr Thr Gly Ser Ser Val Thr Leu Gly Cys Leu Val Lys Gly
                165                 170                 175
Tyr Phe Pro Glu Pro Val Thr Leu Thr Trp Asn Ser Gly Ser Leu Ser
            180                 185                 190
Ser Gly Val His Thr Phe Pro Ala Val Leu Gln Ser Asp Leu Tyr Thr
        195                 200                 205
Leu Ser Ser Ser Val Thr Val Thr Ser Ser Thr Trp Pro Ser Gln Ser

|   |   |   | 210 |   |   |   | 215 |   |   |   | 220 |   |
|---|---|---|---|---|---|---|---|---|---|---|---|---|
Ile Thr Cys Asn Val Ala His Pro Ala Ser Ser Thr Lys Val Asp Lys 225 230 235 240
Lys Ile Glu Pro Arg Gly Pro Thr Ile Lys Pro Cys Pro Pro Cys Lys 245 250 255
Cys Pro Ala Pro Asn Leu Leu Gly Gly Pro Ser Val Phe Ile Phe Pro 260 265 270
Pro Lys Ile Lys Asp Val Leu Met Ile Ser Leu Ser Pro Ile Val Thr 275 280 285
Cys Val Val Val Asp Val Ser Glu Asp Asp Pro Asp Val Gln Ile Ser 290 295 300
Trp Phe Val Asn Asn Val Glu Val His Thr Ala Gln Thr Gln Thr His 305 310 315 320
Arg Glu Asp Tyr Asn Ser Thr Leu Arg Val Val Ser Ala Leu Pro Ile 325 330 335
Gln His Gln Asp Trp Met Ser Gly Lys Glu Phe Lys Cys Lys Val Asn 340 345 350
Asn Lys Asp Leu Pro Ala Pro Ile Glu Arg Thr Ile Ser Lys Pro Lys 355 360 365
Gly Ser Val Arg Ala Pro Gln Val Tyr Val Leu Pro Pro Pro Glu Glu 370 375 380
Glu Met Thr Lys Lys Gln Val Thr Leu Thr Cys Met Val Thr Asp Phe 385 390 395 400
Met Pro Glu Asp Ile Tyr Val Glu Trp Thr Asn Asn Gly Lys Thr Glu 405 410 415
Leu Asn Tyr Lys Asn Thr Glu Pro Val Leu Asp Ser Asp Gly Ser Tyr 420 425 430
Phe Met Tyr Ser Lys Leu Arg Val Glu Lys Lys Asn Trp Val Glu Arg 435 440 445
Asn Ser Tyr Ser Cys Ser Val Val His Glu Gly Leu His Asn His His 450 455 460

Thr Thr Lys Ser Phe Ser Arg Thr Pro Gly Lys
465 470 475

<210> 50
<211> 237
<212> PRT
<213> Artificial Sequence
<220>
<223> D9 light chain_mouse IgG2 Fc_full sequence
<400> 50

Met Glu Thr Asp Thr Leu Leu Leu Trp Val Leu Leu Leu Trp Val Pro
1 5 10 15
Gly Ser Thr Trp Gln Ser Val Leu Thr Gln Pro Pro Ser Ala Ser Gly
20 25 30
Thr Pro Gly Gln Arg Val Thr Ile Ser Cys Ser Asp Ser Ser Ser Asn
35 40 45
Ile Gly Ser Asn Thr Val Ser Trp Tyr Gln Gln Leu Pro Gly Thr Ala
50 55 60
Pro Lys Leu Leu Ile Tyr Ala Asp Asn Asn Arg Pro Ser Gly Val Pro
65 70 75 80
Asp Arg Phe Ser Gly Ser Lys Ser Gly Thr Ser Ala Ser Leu Ala Ile
85 90 95
Ser Gly Leu Arg Ser Glu Asp Glu Ala Asp Tyr Tyr Cys Gly Thr Trp
100 105 110
Asp Tyr Ser Leu Ser Gly Tyr Val Phe Gly Gly Gly Thr Lys Leu Thr
115 120 125
Val Leu Arg Thr Val Ala Ala Pro Thr Val Ser Ile Phe Pro Pro Ser
130 135 140
Ser Glu Gln Leu Thr Ser Gly Gly Ala Ser Val Val Cys Phe Leu Asn
145 150 155 160
Asn Phe Tyr Pro Lys Asp Ile Asn Val Lys Trp Lys Ile Asp Gly Ser 165                 170                 175
Glu Arg Gln Asn Gly Val Leu Asn Ser Trp Thr Asp Gln Asp Ser Lys
              180                 185                 190
Asp Ser Thr Tyr Ser Met Ser Ser Thr Leu Thr Leu Thr Lys Asp Glu
              195                 200                 205
Tyr Glu Arg His Asn Ser Tyr Thr Cys Glu Ala Thr His Lys Thr Ser
          210                 215                 220
Thr Ser Pro Ile Val Lys Ser Phe Asn Arg Asn Glu Cys
225                 230                 235

<210>   51
<211>   475
<212>   PRT
<213>   Artificial Sequence
<220>
<223>   H6 heavy chain_mouse IgG2 Fc_full sequence
<400>   51
Met Glu Thr Asp Thr Leu Leu Leu Trp Val Leu Leu Leu Trp Val Pro
 1               5                  10                 15
Gly Ser Thr Trp Glu Val Gln Leu Leu Glu Ser Gly Gly Gly Leu Val
                20                 25                 30
Gln Pro Gly Gly Ser Leu Arg Leu Ser Cys Ala Ala Ser Gly Phe Thr
             35                 40                 45
Phe Ser Asn Tyr Ala Met Ser Trp Val Arg Gln Ala Pro Gly Lys Gly
         50                 55                 60
Leu Glu Trp Val Ser Val Ile Ser His Gly Gly Gly Ser Thr Tyr Tyr
 65                 70                 75                 80
Ala Asp Ser Val Lys Gly Arg Phe Thr Ile Ser Arg Asp Asn Ser Lys
                85                 90                 95
Asn Thr Leu Tyr Leu Gln Met Asn Ser Leu Arg Ala Glu Asp Thr Ala
               100                105                110

Val Tyr Tyr Cys Ala Arg Val Ile Ser Asn Cys His Leu Gly Val Cys
              115                    120                    125

Tyr Tyr Ser Asn Gly Met Asp Val Trp Gly Gln Gly Thr Leu Val Thr
   130                    135                    140

Val Ser Ser Thr Thr Ala Pro Ser Val Tyr Pro Leu Ala Pro Val Cys
145                    150                    155                    160

Gly Asp Thr Thr Gly Ser Ser Val Thr Leu Gly Cys Leu Val Lys Gly
              165                    170                    175

Tyr Phe Pro Glu Pro Val Thr Leu Thr Trp Asn Ser Gly Ser Leu Ser
              180                    185                    190

Ser Gly Val His Thr Phe Pro Ala Val Leu Gln Ser Asp Leu Tyr Thr
   195                    200                    205

Leu Ser Ser Ser Val Thr Val Thr Ser Ser Thr Trp Pro Ser Gln Ser
      210                  215                    220

Ile Thr Cys Asn Val Ala His Pro Ala Ser Ser Thr Lys Val Asp Lys
225                    230                    235                    240

Lys Ile Glu Pro Arg Gly Pro Thr Ile Lys Pro Cys Pro Pro Cys Lys
              245                    250                    255

Cys Pro Ala Pro Asn Leu Leu Gly Gly Pro Ser Val Phe Ile Phe Pro
              260                    265                    270

Pro Lys Ile Lys Asp Val Leu Met Ile Ser Leu Ser Pro Ile Val Thr
   275                    280                    285

Cys Val Val Val Asp Val Ser Glu Asp Asp Pro Asp Val Gln Ile Ser
   290                    295                    300

Trp Phe Val Asn Asn Val Glu Val His Thr Ala Gln Thr Gln Thr His
305                    310                    315                    320

Arg Glu Asp Tyr Asn Ser Thr Leu Arg Val Val Ser Ala Leu Pro Ile
              325                    330                    335

Gln His Gln Asp Trp Met Ser Gly Lys Glu Phe Lys Cys Lys Val Asn
              340                    345                    350

Asn Lys Asp Leu Pro Ala Pro Ile Glu Arg Thr Ile Ser Lys Pro Lys

Gly Ser Val Arg Ala Pro Gln Val Tyr Val Leu Pro Pro Glu Glu
                355                 360                 365
Glu Met Thr Lys Lys Gln Val Thr Leu Thr Cys Met Val Thr Asp Phe
        370                 375                 380
Met Pro Glu Asp Ile Tyr Val Glu Trp Thr Asn Asn Gly Lys Thr Glu
385                 390                 395                 400
Leu Asn Tyr Lys Asn Thr Glu Pro Val Leu Asp Ser Asp Gly Ser Tyr
                405                 410                 415
Phe Met Tyr Ser Lys Leu Arg Val Glu Lys Lys Asn Trp Val Glu Arg
            420                 425                 430
Asn Ser Tyr Ser Cys Ser Val Val His Glu Gly Leu His Asn His His
        435                 440                 445
Thr Thr Lys Ser Phe Ser Arg Thr Pro Gly Lys
    450                 455                 460
465                 470                 475

<210> 52
<211> 237
<212> PRT
<213> Artificial Sequence
<220>
<223>   H6 light chain_mouse IgG2 Fc_full sequence
<400> 52
Met Glu Thr Asp Thr Leu Leu Leu Trp Val Leu Leu Leu Trp Val Pro
 1               5                   10                  15
Gly Ser Thr Trp Gln Ser Val Leu Thr Gln Pro Pro Ser Ala Ser Gly
            20                  25                  30
Thr Pro Gly Gln Arg Val Thr Ile Ser Cys Ser Gly Ser Ser Ser Asn
        35                  40                  45
Ile Gly Asn Asn Asp Val Tyr Trp Tyr Gln Gln Leu Pro Gly Thr Ala
    50                  55                  60

Pro Lys Leu Leu Ile Tyr Ser Asp Ser Gln Arg Pro Ser Gly Val Pro
        65                  70                  75                  80
Asp Arg Phe Ser Gly Ser Lys Ser Gly Thr Ser Ala Ser Leu Ala Ile
                    85                  90                  95
Ser Gly Leu Arg Ser Glu Asp Glu Ala Asp Tyr Tyr Cys Gly Thr Trp
                   100                 105                 110
Asp Tyr Ser Leu Ser Gly Tyr Val Phe Gly Gly Gly Thr Lys Leu Thr
                   115                 120                 125
Val Leu Arg Thr Val Ala Ala Pro Thr Val Ser Ile Phe Pro Pro Ser
        130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
                   165                 170                 175
Glu Arg Gln Asn Gly Val Leu Asn Ser Trp Thr Asp Gln Asp Ser Lys
                   180                 185                 190
Asp Ser Thr Tyr Ser Met Ser Ser Thr Leu Thr Leu Thr Lys Asp Glu
                   195                 200                 205
Tyr Glu Arg His Asn Ser Tyr Thr Cys Glu Ala Thr His Lys Thr Ser
        210                 215                 220
Thr Ser Pro Ile Val Lys Ser Phe Asn Arg Asn Glu Cys
225                 230                 235

SEQUENCE LISTING

<160> NUMBER OF SEQ ID NOS: 70

<210> SEQ ID NO 1
<211> LENGTH: 759
<212> TYPE: PRT
<213> ORGANISM: Homo sapiens

<400> SEQUENCE: 1

Gly Pro Arg Ala Pro Cys Ala Ala Cys Thr Cys Ala Gly Asp Ser
1               5                   10                  15

Leu Asp Cys Gly Gly Arg Gly Leu Ala Ala Leu Pro Gly Asp Leu Pro
                20                  25                  30

Ser Trp Thr Arg Ser Leu Asn Leu Ser Tyr Asn Lys Leu Ser Glu Ile
            35                  40                  45

Asp Pro Ala Gly Phe Glu Asp Leu Pro Asn Leu Gln Glu Val Tyr Leu
        50                  55                  60

Asn Asn Asn Glu Leu Thr Ala Val Pro Ser Leu Gly Ala Ala Ser Ser
65                  70                  75                  80

His Val Val Ser Leu Phe Leu Gln His Asn Lys Ile Arg Ser Val Glu
                85                  90                  95

Gly Ser Gln Leu Lys Ala Tyr Leu Ser Leu Glu Val Leu Asp Leu Ser
                100                 105                 110

Leu Asn Asn Ile Thr Glu Val Arg Asn Thr Cys Phe Pro His Gly Pro
            115                 120                 125

Pro Ile Lys Glu Leu Asn Leu Ala Gly Asn Arg Ile Gly Thr Leu Glu
        130                 135                 140

Leu Gly Ala Phe Asp Gly Leu Ser Arg Ser Leu Leu Thr Leu Arg Leu
145                 150                 155                 160

Ser Lys Asn Arg Ile Thr Gln Leu Pro Val Arg Ala Phe Lys Leu Pro
                165                 170                 175

Arg Leu Thr Gln Leu Asp Leu Asn Arg Asn Arg Ile Arg Leu Ile Glu
                180                 185                 190

Gly Leu Thr Phe Gln Gly Leu Asn Ser Leu Glu Val Leu Lys Leu Gln
            195                 200                 205

Arg Asn Asn Ile Ser Lys Leu Thr Asp Gly Ala Phe Trp Gly Leu Ser
        210                 215                 220

Lys Met His Val Leu His Leu Glu Tyr Asn Ser Leu Val Glu Val Asn
225                 230                 235                 240

Ser Gly Ser Leu Tyr Gly Leu Thr Ala Leu His Gln Leu His Leu Ser
                245                 250                 255

Asn Asn Ser Ile Ala Arg Ile His Arg Lys Gly Trp Ser Phe Cys Gln
                260                 265                 270

Lys Leu His Glu Leu Val Leu Ser Phe Asn Asn Leu Thr Arg Leu Asp
            275                 280                 285

Glu Glu Ser Leu Ala Glu Leu Ser Ser Leu Ser Val Leu Arg Leu Ser
        290                 295                 300

His Asn Ser Ile Ser His Ile Ala Glu Gly Ala Phe Lys Gly Leu Arg
305                 310                 315                 320

Ser Leu Arg Val Leu Asp Leu Asp His Asn Glu Ile Ser Gly Thr Ile
                325                 330                 335

Glu Asp Thr Ser Gly Ala Phe Ser Gly Leu Asp Ser Leu Ser Lys Leu
                340                 345                 350

Thr Leu Phe Gly Asn Lys Ile Lys Ser Val Ala Lys Arg Ala Phe Ser
            355                 360                 365

Gly Leu Glu Gly Leu Glu His Leu Asn Leu Gly Gly Asn Ala Ile Arg
370                 375                 380

Ser Val Gln Phe Asp Ala Phe Val Lys Met Lys Asn Leu Lys Glu Leu
385                 390                 395                 400

His Ile Ser Ser Asp Ser Phe Leu Cys Asp Cys Gln Leu Lys Trp Leu
            405                 410                 415

Pro Pro Trp Leu Ile Gly Arg Met Leu Gln Ala Phe Val Thr Ala Thr
            420                 425                 430

Cys Ala His Pro Glu Ser Leu Lys Gly Gln Ser Ile Phe Ser Val Pro
            435                 440                 445

Pro Glu Ser Phe Val Cys Asp Asp Phe Leu Lys Pro Gln Ile Ile Thr
450                 455                 460

Gln Pro Glu Thr Thr Met Ala Met Val Gly Lys Asp Ile Arg Phe Thr
465                 470                 475                 480

Cys Ser Ala Ala Ser Ser Ser Ser Pro Met Thr Phe Ala Trp Lys
                485                 490                 495

Lys Asp Asn Glu Val Leu Thr Asn Ala Asp Met Glu Asn Phe Val His
            500                 505                 510

Val His Ala Gln Asp Gly Glu Val Met Glu Tyr Thr Thr Ile Leu His
515                 520                 525

Leu Arg Gln Val Thr Phe Gly His Glu Gly Arg Tyr Gln Cys Val Ile
530                 535                 540

Thr Asn His Phe Gly Ser Thr Tyr Ser His Lys Ala Arg Leu Thr Val
545                 550                 555                 560

Asn Val Leu Pro Ser Phe Thr Lys Thr Pro His Asp Ile Thr Ile Arg
            565                 570                 575

Thr Thr Thr Val Ala Arg Leu Glu Cys Ala Ala Thr Gly His Pro Asn
            580                 585                 590

Pro Gln Ile Ala Trp Gln Lys Asp Gly Gly Thr Asp Phe Pro Ala Ala
            595                 600                 605

Arg Glu Arg Arg Met His Val Met Pro Asp Asp Val Phe Phe Ile
            610                 615                 620

Thr Asp Val Lys Ile Asp Asp Ala Gly Val Tyr Ser Cys Thr Ala Gln
625                 630                 635                 640

Asn Ser Ala Gly Ser Ile Ser Ala Asn Ala Thr Leu Thr Val Leu Glu
                645                 650                 655

Thr Pro Ser Leu Val Val Pro Leu Glu Asp Arg Val Val Ser Val Gly
            660                 665                 670

Glu Thr Val Ala Leu Gln Cys Lys Ala Thr Gly Asn Pro Pro Pro Arg
            675                 680                 685

Ile Thr Trp Phe Lys Gly Asp Arg Pro Leu Ser Leu Thr Glu Arg His
            690                 695                 700

His Leu Thr Pro Asp Asn Gln Leu Leu Val Val Gln Asn Val Val Ala
705                 710                 715                 720

Glu Asp Ala Gly Arg Tyr Thr Cys Glu Met Ser Asn Thr Leu Gly Thr
            725                 730                 735

Glu Arg Ala His Ser Gln Leu Ser Val Leu Pro Ala Ala Gly Cys Arg
            740                 745                 750

Lys Asp Gly Thr Thr Val Gly
            755

<210> SEQ ID NO 2
<211> LENGTH: 2397
<212> TYPE: DNA

<213> ORGANISM: Homo sapiens

<400> SEQUENCE: 2

```
ggcccgcggg cgccctgcgc ggccgcctgc acttgcgctg gggactcgct ggactgcggt      60
gggcgcgggc tggctgcgtt gcccggggac ctgccctcct ggacgcggag cctaaacctg     120
agttacaaca aactctctga gattgaccct gctggttttg aggacttgcc gaacctacag     180
gaagtgtacc tcaataataa tgagttgaca gcggtaccat ccctgggcgc tgcttcatca     240
catgtcgtct ctctctttct gcagcacaac aagattcgca gcgtggaggg gagccagctg     300
aaggcctacc tttccttaga agtgttagat ctgagtttga acaacatcac ggaagtgcgg     360
aacacctgct ttccacacgg accgcctata aaggagctca acctggcagg caatcggatt     420
ggcaccctgg agtgggagc atttgatggt ctgtcacggt cgctgctaac tcttcgcctg     480
agcaaaaaca ggatcaccca gcttcctgta agagcattca agctacccag gctgacacaa     540
ctggacctca atcggaacag gattcggctg atagagggcc tcaccttcca ggggctcaac     600
agcttggagg tgctgaagct tcagcgaaac aacatcagca aactgacaga tgggccttc     660
tggggactgt ccaagatgca tgtgctgcac ctggagtaca acagcctggt agaagtgaac     720
agcggctcgc tctacggcct cacggccctg catcagctcc acctcagcaa caattccatc     780
gctcgcattc accgcaaggg ctggagcttc tgccagaagc tgcatgagtt ggtcctgtcc     840
ttcaacaacc tgacacggct ggacgaggag agcctggccg agctgagcag cctgagtgtc     900
ctgcgtctca gccacaattc catcagccac attgcggagg gtgccttcaa gggactcagg     960
agcctgcgag tcttggatct ggaccataac gagatttcgg gcacaataga ggacacgagc    1020
ggcgccttct cagggctcga cagcctcagc aagctgactc tgtttggaaa caagatcaag    1080
tctgtggcta agagagcatt ctcggggctg aaggcctgg agcacctgaa ccttggaggg    1140
aatgcgatca gatctgtcca gtttgatgcc tttgtgaaga tgaagaatct taagagctc    1200
catatcagca gcgacagctt cctgtgtgac tgccagctga gtggctgcc cccgtggcta    1260
attggcagga tgctgcaggc ctttgtgaca gccacctgtg cccacccaga atcactgaag    1320
ggtcagagca tttttctctgt gccaccagag agtttcgtgt gcgatgactt cctgaagcca    1380
cagatcatca cccagccaga aaccaccatg gctatggtgg gcaaggacat ccggtttaca    1440
tgctcagcag ccagcagcag cagctccccc atgacctttg cctggaagaa agacaatgaa    1500
gtcctgacca atgcagacat ggagaacttt gtccacgtcc acgcgcagga cggggaagtg    1560
atggagtaca ccaccatcct gcacctccgt caggtcactt cgggcacga gggccgctac    1620
caatgtgtca tcaccaacca ctttggctcc acctattcac ataaggccag gctcaccgtg    1680
aatgtgttgc catcattcac caaaacgccc cacgacataa ccatccggac caccaccgtg    1740
gcccgcctcg aatgtgctgc cacaggtcac ccaaaccctc agattgcctg gcagaaggat    1800
ggaggcacgg atttccccgc tgcccgtgag cgacgcatgc atgtcatgcc ggatgacgac    1860
gtgtttttca tcactgatgt gaaaatagat gacgcagggg tttacagctg tactgctcag    1920
aactcagccg gttctatttc agctaatgcc accctgactg tcctagagac cccatccttg    1980
gtggtcccct ggaagaccg tgtggtatct gtgggagaaa cagtgccct ccaatgcaaa    2040
gccacgggga accctccgcc ccgcatcacc tggttcaagg gggaccgccc gctgagcctc    2100
actgagcggc accacctgac ccctgacaac cagctcctgg tggttcagaa cgtggtggca    2160
gaggatgcgg gccgatatac ctgtgagatg tccaacaccc tgggcacgga gcgagctcac    2220
agccagctga gcgtcctgcc cgcagcaggc tgcaggaagg atgggaccac ggtaggcatc    2280
```

```
ttcaccattg ctgtcgtgag cagcatcgtc ctgacgtcac tggtctgggt gtgcatcatc    2340
taccagacca ggaagaagag tgaagagtac agtgtcacca acacagatga aaccgtc       2397
```

<210> SEQ ID NO 3
<211> LENGTH: 761
<212> TYPE: PRT
<213> ORGANISM: Mus musculus

<400> SEQUENCE: 3

```
Gln Ala Gly Pro Arg Ala Pro Cys Ala Ala Cys Thr Cys Ala Gly
1               5                   10                  15

Asp Ser Leu Asp Cys Ser Gly Arg Gly Leu Ala Thr Leu Pro Arg Asp
            20                  25                  30

Leu Pro Ser Trp Thr Arg Ser Leu Asn Leu Ser Tyr Asn Arg Leu Ser
        35                  40                  45

Glu Ile Asp Ser Ala Ala Phe Glu Asp Leu Thr Asn Leu Gln Glu Val
50                  55                  60

Tyr Leu Asn Ser Asn Glu Leu Thr Ala Ile Pro Ser Leu Gly Ala Ala
65                  70                  75                  80

Ser Ile Gly Val Val Ser Leu Phe Leu Gln His Asn Lys Ile Leu Ser
                85                  90                  95

Val Asp Gly Ser Gln Leu Lys Ser Tyr Leu Ser Leu Glu Val Leu Asp
            100                 105                 110

Leu Ser Ser Asn Asn Ile Thr Glu Ile Arg Ser Ser Cys Phe Pro Asn
        115                 120                 125

Gly Leu Arg Ile Arg Glu Leu Asn Leu Ala Ser Asn Arg Ile Ser Ile
130                 135                 140

Leu Glu Ser Gly Ala Phe Asp Gly Leu Ser Arg Ser Leu Leu Thr Leu
145                 150                 155                 160

Arg Leu Ser Lys Asn Arg Ile Thr Gln Leu Pro Val Lys Ala Phe Lys
                165                 170                 175

Leu Pro Arg Leu Thr Gln Leu Asp Leu Asn Arg Asn Arg Ile Arg Leu
            180                 185                 190

Ile Glu Gly Leu Thr Phe Gln Gly Leu Asp Ser Leu Glu Val Leu Arg
        195                 200                 205

Leu Gln Arg Asn Asn Ile Ser Arg Leu Thr Asp Gly Ala Phe Trp Gly
210                 215                 220

Leu Ser Lys Met His Val Leu His Leu Glu Tyr Asn Ser Leu Val Glu
225                 230                 235                 240

Val Asn Ser Gly Ser Leu Tyr Gly Leu Thr Ala Leu His Gln Leu His
                245                 250                 255

Leu Ser Asn Asn Ser Ile Ser Arg Ile Gln Arg Asp Gly Trp Ser Phe
            260                 265                 270

Cys Gln Lys Leu His Glu Leu Ile Leu Ser Phe Asn Asn Leu Thr Arg
        275                 280                 285

Leu Asp Glu Glu Ser Leu Ala Glu Leu Ser Ser Leu Ser Ile Leu Arg
        290                 295                 300

Leu Ser His Asn Ala Ile Ser His Ile Ala Glu Gly Ala Phe Lys Gly
305                 310                 315                 320

Leu Lys Ser Leu Arg Val Leu Asp Leu Asp His Asn Glu Ile Ser Gly
                325                 330                 335

Thr Ile Glu Asp Thr Ser Gly Ala Phe Thr Gly Leu Asp Asn Leu Ser
            340                 345                 350
```

```
Lys Leu Thr Leu Phe Gly Asn Lys Ile Lys Ser Val Ala Lys Arg Ala
            355                 360                 365

Phe Ser Gly Leu Glu Ser Leu Glu His Leu Asn Leu Gly Glu Asn Ala
    370                 375                 380

Ile Arg Ser Val Gln Phe Asp Ala Phe Ala Lys Met Lys Asn Leu Lys
385                 390                 395                 400

Glu Leu Tyr Ile Ser Ser Glu Ser Phe Leu Cys Asp Cys Gln Leu Lys
                405                 410                 415

Trp Leu Pro Pro Trp Leu Met Gly Arg Met Leu Gln Ala Phe Val Thr
            420                 425                 430

Ala Thr Cys Ala His Pro Glu Ser Leu Lys Gly Gln Ser Ile Phe Ser
            435                 440                 445

Val Leu Pro Asp Ser Phe Val Cys Asp Asp Phe Pro Lys Pro Gln Ile
    450                 455                 460

Ile Thr Gln Pro Glu Thr Thr Met Ala Val Val Gly Lys Asp Ile Arg
465                 470                 475                 480

Phe Thr Cys Ser Ala Ala Ser Ser Ser Ser Pro Met Thr Phe Ala
                485                 490                 495

Trp Lys Lys Asp Asn Glu Val Leu Ala Asn Ala Asp Met Glu Asn Phe
            500                 505                 510

Ala His Val Arg Ala Gln Asp Gly Glu Val Met Glu Tyr Thr Thr Ile
    515                 520                 525

Leu His Leu Arg His Val Thr Phe Gly His Glu Gly Arg Tyr Gln Cys
    530                 535                 540

Ile Ile Thr Asn His Phe Gly Ser Thr Tyr Ser His Lys Ala Arg Leu
545                 550                 555                 560

Thr Val Asn Val Leu Pro Ser Phe Thr Lys Ile Pro His Asp Ile Ala
                565                 570                 575

Ile Arg Thr Gly Thr Thr Ala Arg Leu Glu Cys Ala Ala Thr Gly His
            580                 585                 590

Pro Asn Pro Gln Ile Ala Trp Gln Lys Asp Gly Gly Thr Asp Phe Pro
    595                 600                 605

Ala Ala Arg Glu Arg Arg Met His Val Met Pro Asp Asp Asp Val Phe
610                 615                 620

Phe Ile Thr Asp Val Lys Ile Asp Asp Met Gly Val Tyr Ser Cys Thr
625                 630                 635                 640

Ala Gln Asn Ser Ala Gly Ser Val Ser Ala Asn Ala Thr Leu Thr Val
                645                 650                 655

Leu Glu Thr Pro Ser Leu Ala Val Pro Leu Glu Asp Arg Val Val Thr
            660                 665                 670

Val Gly Glu Thr Val Ala Phe Gln Cys Lys Ala Thr Gly Ser Pro Thr
    675                 680                 685

Pro Arg Ile Thr Trp Leu Lys Gly Gly Arg Pro Leu Ser Leu Thr Glu
    690                 695                 700

Arg His His Phe Thr Pro Gly Asn Gln Leu Leu Val Val Gln Asn Val
705                 710                 715                 720

Met Ile Asp Asp Ala Gly Arg Tyr Thr Cys Glu Met Ser Asn Pro Leu
                725                 730                 735

Gly Thr Glu Arg Ala His Ser Gln Leu Ser Ile Leu Pro Thr Pro Gly
            740                 745                 750

Cys Arg Lys Asp Gly Thr Thr Val Gly
            755                 760
```

```
<210> SEQ ID NO 4
<211> LENGTH: 2283
<212> TYPE: DNA
<213> ORGANISM: Mus musculus

<400> SEQUENCE: 4
caggctggcc cgcgggcccc ctgcgcggcc gcctgcactt gcgccgggga ctcgctggac      60
tgcagtgggc gcgggctggc gacgctgccc cgggacctgc cctcctggac gcgcagccta     120
aacctgagtt ataacagact ctccgagatc gactctgctg cttttgagga cttgacgaat     180
ctgcaggaag tgtacctcaa cagcaatgag ctgacagcca taccatcact gggcgctgct     240
tccataggag ttgtctctct cttttttgcag cacaacaaga tccttagtgt ggatgggagc     300
cagctgaagt cgtacctgtc cttggaagtg ctggatctga gttccaacaa catcacggaa     360
attcggagct cctgtttccc gaacggcctg cgtataaggg aactcaactt ggcgagcaac     420
cgcatcagca tcctggagtc tggagcattt gatggtctgt cgcggtcact gctgactctc     480
cgtctgagca aaaacaggat cacccagctt cctgtgaaag cgttcaagct acccaggctg     540
acacaactag acctgaatcg gaatcggatt cggctgattg aaggcctcac gttccagggg     600
ctcgacagct tagaggtgct gaggcttcag aggaacaaca tcagcaggct gacggacggg     660
gccttctggg ggctgtctaa gatgcacgtg ctgcacctgg agtacaacag tctggtggaa     720
gtgaacagtg gctccctcta tggcctcaca gccctgcacc agctgcacct cagcaacaac     780
tccatctctc gaattcagcg tgatggctgg agcttctgcc aaaagctgca tgagttgatt     840
ctgtccttca caacctcac gcggctggat gaggagagtc tagcggagtt gagcagcctc     900
agtatcctgc gcctcagtca aacgccatc agtcacattg ctgaaggcgc cttcaaggga     960
ctcaagagtc tgcgggtctt ggacctggac cataacgaga tctcgggtac aatcgaggat    1020
accagtggtg cctttacggg gcttgacaac ctcagcaagc tgactctgtt tggaaacaag    1080
atcaaatctg tggctaagag agccttctcg ggcctggaaa gcctggaaca cctgaacctt    1140
ggagagaatg caatcaggtc tgtccagttt gatgcctttg caaagatgaa gaaccttaaa    1200
gagctctaca tcagcagtga gagcttcctg tgtgactgcc agctcaagtg gctgccccca    1260
tggctaatgg gtaggatgct gcaggccttt gtgacagcca cctgtgccca tccagagtcg    1320
ctgaagggcc agagcatttt ctcagtgctg ccagacagct ttgtgtgtga tgactttcca    1380
aagccacaga tcatcaccca gcctgagacg accatggctg tggtgggcaa ggacatccgt    1440
ttcacatgct ccgcagccag cagcagcagc tcaccaatga ccttcgcctg gaagaaggac    1500
aatgaggtcc tggccaatgc agacatggag aactttgccc acgtccgtgc acaggacggc    1560
gaagtgatgg agtataccac tatcctgcac ctccgtcacg tcacctttgg gcacgagggc    1620
cgctaccagt gtatcatcac aaaccacttt ggctccacat actcccacaa agccaggctc    1680
actgtgaatg tgttgccatc attcactaaa ataccccatg acattgccat ccggactggc    1740
accacagccc gcctcgagtg tgctgccacg ggccacccta accctcagat tgcctggcag    1800
aaggatggag gcaccgattt cccggcagct cgtgagcgac gcatgcatgt tatgccagac    1860
gatgatgtgt tcttcatcac tgatgtgaaa atagacgaca tggggtctca cagctgcact    1920
gcccagaact cggcaggctc ggtttcagcc aacgctaccc tcacagtctt agaaactcca    1980
tccttggcag tgcctctgga agaccgtgtg gtaactgtgg agaaacagt ggccttccag    2040 tgcaaagcaa ccgggagccc cacaccacgc atccctggc ttaagggagg tcgcccattg    2100
agcctcacag agcgccacca tttcactcca ggcaaccagc tgctggttgt tcagaatgtg    2160
```

```
atgatagacg atgcagggcg gtatacctgt gagatgtcta atcccctggg cactgagcga   2220
gcacatagcc agctgagcat tttacctacc cctggctgcc ggaaggatgg gaccaccgta   2280
ggc                                                                 2283
```

<210> SEQ ID NO 5
<211> LENGTH: 5
<212> TYPE: PRT
<213> ORGANISM: Artificial Sequence
<220> FEATURE:
<223> OTHER INFORMATION: A8 heavy chain CDR 1

<400> SEQUENCE: 5

Asp Tyr Asp Met Ser
1               5

<210> SEQ ID NO 6
<211> LENGTH: 9
<212> TYPE: PRT
<213> ORGANISM: Artificial Sequence
<220> FEATURE:
<223> OTHER INFORMATION: A8 heavy chain CDR 2

<400> SEQUENCE: 6

Trp Ile Ser His Gly Gly Gly Ser Ile
1               5

<210> SEQ ID NO 7
<211> LENGTH: 19
<212> TYPE: PRT
<213> ORGANISM: Artificial Sequence
<220> FEATURE:
<223> OTHER INFORMATION: A8 heavy chain CDR 3

<400> SEQUENCE: 7

Arg Gly Leu Gly Leu Cys Lys Thr Gly Leu Cys Tyr Tyr Tyr Asp Ala
1               5                   10                  15

Met Asp Val

<210> SEQ ID NO 8
<211> LENGTH: 13
<212> TYPE: PRT
<213> ORGANISM: Artificial Sequence
<220> FEATURE:
<223> OTHER INFORMATION: A8 light chain CDR 1

<400> SEQUENCE: 8

Thr Gly Ser Ser Ser Asn Ile Gly Asn Asn Ser Val Thr
1               5                   10

<210> SEQ ID NO 9
<211> LENGTH: 4
<212> TYPE: PRT
<213> ORGANISM: Artificial Sequence
<220> FEATURE:
<223> OTHER INFORMATION: A8 light chain CDR 2

<400> SEQUENCE: 9

Ala Asp Asn Asn
1

<210> SEQ ID NO 10
<211> LENGTH: 9
<212> TYPE: PRT
<213> ORGANISM: Artificial Sequence
<220> FEATURE:

<223> OTHER INFORMATION: A8 light chain CDR 3

<400> SEQUENCE: 10

Ala Ala Trp Asp Ser Ser Leu Ser Ala
1               5

<210> SEQ ID NO 11
<211> LENGTH: 147
<212> TYPE: PRT
<213> ORGANISM: Artificial Sequence
<220> FEATURE:
<223> OTHER INFORMATION: A8 heavy chain_variable region

<400> SEQUENCE: 11

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asp Tyr Asp Met Ser Trp Val Arg Gln Val Pro Gly Lys Gly
        50                  55                  60

Leu Glu Trp Val Ser Trp Ile Ser His Gly Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Gly Leu Gly Leu Cys Lys Thr Gly Leu Cys
        115                 120                 125

Tyr Tyr Tyr Asp Ala Met Asp Val Trp Gly Gln Gly Thr Leu Val Thr
    130                 135                 140

Val Ser Ser
145

<210> SEQ ID NO 12
<211> LENGTH: 130
<212> TYPE: PRT
<213> ORGANISM: Artificial Sequence
<220> FEATURE:
<223> OTHER INFORMATION: A8 light chain_variable region

<400> SEQUENCE: 12

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Thr Gly Ser Ser Ser Asn
            35                  40                  45

Ile Gly Asn Asn Ser Val Thr Trp Tyr Gln Gln Leu Pro Gly Thr Ala
        50                  55                  60

Pro Lys Leu Leu Ile Tyr Ala Asp Asn Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Ser Ser Leu Ser Ala Tyr Val Phe Gly Gly Gly Thr Lys Leu Thr

-continued

```
             115                 120                 125
Val Leu
    130

<210> SEQ ID NO 13
<211> LENGTH: 5
<212> TYPE: PRT
<213> ORGANISM: Artificial Sequence
<220> FEATURE:
<223> OTHER INFORMATION: B8 heavy chain CDR 1

<400> SEQUENCE: 13

Asp Tyr Tyr Met Ser
1               5

<210> SEQ ID NO 14
<211> LENGTH: 9
<212> TYPE: PRT
<213> ORGANISM: Artificial Sequence
<220> FEATURE:
<223> OTHER INFORMATION: B8 heavy chain CDR 2

<400> SEQUENCE: 14

Gly Ile Ser His Asp Ser Gly Ser Lys
1               5

<210> SEQ ID NO 15
<211> LENGTH: 8
<212> TYPE: PRT
<213> ORGANISM: Artificial Sequence
<220> FEATURE:
<223> OTHER INFORMATION: B8 heavy chain CDR 3

<400> SEQUENCE: 15

Arg His Trp Thr Thr Phe Asp Tyr
1               5

<210> SEQ ID NO 16
<211> LENGTH: 13
<212> TYPE: PRT
<213> ORGANISM: Artificial Sequence
<220> FEATURE:
<223> OTHER INFORMATION: B8 light chain CDR 1

<400> SEQUENCE: 16

Ser Gly Ser Ser Ser Asn Ile Gly Ser Asn Asn Val Thr
1               5                   10

<210> SEQ ID NO 17
<211> LENGTH: 4
<212> TYPE: PRT
<213> ORGANISM: Artificial Sequence
<220> FEATURE:
<223> OTHER INFORMATION: B8 light chain CDR 2

<400> SEQUENCE: 17

Ala Asn Ser Asn
1

<210> SEQ ID NO 18
<211> LENGTH: 9
<212> TYPE: PRT
<213> ORGANISM: Artificial Sequence
<220> FEATURE:
<223> OTHER INFORMATION: B8 light chain CDR 3

<400> SEQUENCE: 18
```

```
Gly Ala Trp Asp Tyr Ser Leu Ser Ala
1               5
```

<210> SEQ ID NO 19
<211> LENGTH: 136
<212> TYPE: PRT
<213> ORGANISM: Artificial Sequence
<220> FEATURE:
<223> OTHER INFORMATION: B8 heavy chain_variable region

<400> SEQUENCE: 19

```
Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asp Tyr Tyr Met Ser Trp Val Arg Gln Ala Pro Gly Lys Gly
        50                  55                  60

Leu Glu Trp Val Ser Gly Ile Ser His Asp Ser Gly Ser Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg His Trp Thr Thr Phe Asp Tyr Trp Gly Gln
        115                 120                 125

Gly Thr Leu Val Thr Val Ser Ser
    130                 135
```

<210> SEQ ID NO 20
<211> LENGTH: 130
<212> TYPE: PRT
<213> ORGANISM: Artificial Sequence
<220> FEATURE:
<223> OTHER INFORMATION: B8 light chain_variable region

<400> SEQUENCE: 20

```
Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Ser Gly Ser Ser Ser Asn
            35                  40                  45

Ile Gly Ser Asn Asn Val Thr Trp Tyr Gln Gln Leu Pro Gly Thr Ala
        50                  55                  60

Pro Lys Leu Leu Ile Tyr Ala Asn Ser Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ala Trp
            100                 105                 110

Asp Tyr Ser Leu Ser Ala Tyr Val Phe Gly Gly Gly Thr Lys Leu Thr
        115                 120                 125

Val Leu
    130
```

```
<210> SEQ ID NO 21
<211> LENGTH: 5
<212> TYPE: PRT
<213> ORGANISM: Artificial Sequence
<220> FEATURE:
<223> OTHER INFORMATION: D9 heavy chain CDR 1

<400> SEQUENCE: 21

Asn Tyr Ala Met Ser
1               5

<210> SEQ ID NO 22
<211> LENGTH: 9
<212> TYPE: PRT
<213> ORGANISM: Artificial Sequence
<220> FEATURE:
<223> OTHER INFORMATION: D9 heavy chain CDR 2

<400> SEQUENCE: 22

Ala Ile Tyr Pro Gly Gly Gly Ser Ile
1               5

<210> SEQ ID NO 23
<211> LENGTH: 19
<212> TYPE: PRT
<213> ORGANISM: Artificial Sequence
<220> FEATURE:
<223> OTHER INFORMATION: D9 heavy chain CDR 3

<400> SEQUENCE: 23

Arg Asp Ile Leu Pro Cys Pro Trp Gly Arg Cys Tyr Tyr Asp Tyr Ala
1               5                   10                  15

Met Asp Val

<210> SEQ ID NO 24
<211> LENGTH: 13
<212> TYPE: PRT
<213> ORGANISM: Artificial Sequence
<220> FEATURE:
<223> OTHER INFORMATION: D9 light chain CDR 1

<400> SEQUENCE: 24

Ser Asp Ser Ser Ser Asn Ile Gly Ser Asn Thr Val Ser
1               5                   10

<210> SEQ ID NO 25
<211> LENGTH: 4
<212> TYPE: PRT
<213> ORGANISM: Artificial Sequence
<220> FEATURE:
<223> OTHER INFORMATION: D9 light chain CDR 2

<400> SEQUENCE: 25

Ala Asp Asn Asn
1

<210> SEQ ID NO 26
<211> LENGTH: 9
<212> TYPE: PRT
<213> ORGANISM: Artificial Sequence
<220> FEATURE:
<223> OTHER INFORMATION: D9 light chain CDR 3

<400> SEQUENCE: 26

Gly Thr Trp Asp Tyr Ser Leu Ser Gly
1               5
```

```
<210> SEQ ID NO 27
<211> LENGTH: 147
<212> TYPE: PRT
<213> ORGANISM: Artificial Sequence
<220> FEATURE:
<223> OTHER INFORMATION: D9 heavy chain_variable region

<400> SEQUENCE: 27

Met Glu Thr Asp Thr Leu Leu Leu Trp Val Leu Leu Trp Val Pro
1               5                   10                  15

Gly Ser Thr Trp Glu Val Gln Leu Leu Glu Ser Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Ala Met Ser Trp Val Arg Gln Ala Pro Gly Lys Gly
    50                  55                  60

Leu Glu Trp Val Ser Ala Ile Tyr Pro Gly Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Ile Leu Pro Cys Pro Trp Gly Arg Cys
        115                 120                 125

Tyr Tyr Asp Tyr Ala Met Asp Val Trp Gly Gln Gly Thr Leu Val Thr
    130                 135                 140

Val Ser Ser
145

<210> SEQ ID NO 28
<211> LENGTH: 130
<212> TYPE: PRT
<213> ORGANISM: Artificial Sequence
<220> FEATURE:
<223> OTHER INFORMATION: D9 light chain_variable region

<400> SEQUENCE: 28

Met Glu Thr Asp Thr Leu Leu Leu Trp Val Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Asp Ser Ser Asn
        35                  40                  45

Ile Gly Ser Asn Thr Val Ser Trp Tyr Gln Gln Leu Pro Gly Thr Ala
    50                  55                  60

Pro Lys Leu Leu Ile Tyr Ala Asp Asn Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
            100                 105                 110

Asp Tyr Ser Leu Ser Gly Tyr Val Phe Gly Gly Gly Thr Lys Leu Thr
        115                 120                 125

Val Leu
    130

<210> SEQ ID NO 29
```

```
<211> LENGTH: 5
<212> TYPE: PRT
<213> ORGANISM: Artificial Sequence
<220> FEATURE:
<223> OTHER INFORMATION: H6 heavy chain CDR 1

<400> SEQUENCE: 29

Asn Tyr Ala Met Ser
1               5

<210> SEQ ID NO 30
<211> LENGTH: 9
<212> TYPE: PRT
<213> ORGANISM: Artificial Sequence
<220> FEATURE:
<223> OTHER INFORMATION: H6 heavy chain CDR 2

<400> SEQUENCE: 30

Val Ile Ser His Gly Gly Gly Ser Thr
1               5

<210> SEQ ID NO 31
<211> LENGTH: 19
<212> TYPE: PRT
<213> ORGANISM: Artificial Sequence
<220> FEATURE:
<223> OTHER INFORMATION: H6 heavy chain CDR 3

<400> SEQUENCE: 31

Arg Val Ile Ser Asn Cys His Leu Gly Val Cys Tyr Tyr Ser Asn Gly
1               5                   10                  15

Met Asp Val

<210> SEQ ID NO 32
<211> LENGTH: 13
<212> TYPE: PRT
<213> ORGANISM: Artificial Sequence
<220> FEATURE:
<223> OTHER INFORMATION: H6 light chain CDR 1

<400> SEQUENCE: 32

Ser Gly Ser Ser Ser Asn Ile Gly Asn Asn Asp Val Tyr
1               5                   10

<210> SEQ ID NO 33
<211> LENGTH: 4
<212> TYPE: PRT
<213> ORGANISM: Artificial Sequence
<220> FEATURE:
<223> OTHER INFORMATION: H6 light chain CDR 2

<400> SEQUENCE: 33

Ser Asp Ser Gln
1

<210> SEQ ID NO 34
<211> LENGTH: 9
<212> TYPE: PRT
<213> ORGANISM: Artificial Sequence
<220> FEATURE:
<223> OTHER INFORMATION: H6 light chain CDR 3

<400> SEQUENCE: 34

Gly Thr Trp Asp Tyr Ser Leu Ser Gly
1               5
```

```
<210> SEQ ID NO 35
<211> LENGTH: 147
<212> TYPE: PRT
<213> ORGANISM: Artificial Sequence
<220> FEATURE:
<223> OTHER INFORMATION: H6 heavy chain_variable region

<400> SEQUENCE: 35

Met Glu Thr Asp Thr Leu Leu Trp Val Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Ala Met Ser Trp Val Arg Gln Ala Pro Gly Lys Gly
    50                  55                  60

Leu Glu Trp Val Ser Val Ile Ser His Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Val Ile Ser Asn Cys His Leu Gly Val Cys
        115                 120                 125

Tyr Tyr Ser Asn Gly Met Asp Val Trp Gly Gln Gly Thr Leu Val Thr
    130                 135                 140

Val Ser Ser
145

<210> SEQ ID NO 36
<211> LENGTH: 130
<212> TYPE: PRT
<213> ORGANISM: Artificial Sequence
<220> FEATURE:
<223> OTHER INFORMATION: H6 light chain_variable region

<400> SEQUENCE: 36

Met Glu Thr Asp Thr Leu Leu Trp Val Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Asn Asn Asp Val Tyr Trp Tyr Gln Gln Leu Pro Gly Thr Ala
    50                  55                  60

Pro Lys Leu Leu Ile Tyr Ser Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
            100                 105                 110

Asp Tyr Ser Leu Ser Gly Tyr Val Phe Gly Gly Gly Thr Lys Leu Thr
    115                 120                 125

Val Leu
130

<210> SEQ ID NO 37
<211> LENGTH: 328
```

<212> TYPE: PRT
<213> ORGANISM: Mus musculus

<400> SEQUENCE: 37

```
Thr Thr Ala Pro Ser Val Tyr Pro Leu Ala Pro Val Cys Gly Asp Thr
1               5                   10                  15

Thr Gly Ser Ser Val Thr Leu Gly Cys Leu Val Lys Gly Tyr Phe Pro
            20                  25                  30

Glu Pro Val Thr Leu Thr Trp Asn Ser Gly Ser Leu Ser Ser Gly Val
        35                  40                  45

His Thr Phe Pro Ala Val Leu Gln Ser Asp Leu Tyr Thr Leu Ser Ser
    50                  55                  60

Ser Val Thr Val Thr Ser Ser Thr Trp Pro Ser Gln Ser Ile Thr Cys
65                  70                  75                  80

Asn Val Ala His Pro Ala Ser Ser Thr Lys Val Asp Lys Lys Ile Glu
                85                  90                  95

Pro Arg Gly Pro Thr Ile Lys Pro Cys Pro Pro Cys Lys Cys Pro Ala
            100                 105                 110

Pro Asn Leu Leu Gly Gly Pro Ser Val Phe Ile Phe Pro Pro Lys Ile
        115                 120                 125

Lys Asp Val Leu Met Ile Ser Leu Ser Pro Ile Val Thr Cys Val Val
130                 135                 140

Val Asp Val Ser Glu Asp Asp Pro Asp Val Gln Ile Ser Trp Phe Val
145                 150                 155                 160

Asn Asn Val Glu Val His Thr Ala Gln Thr Gln Thr His Arg Glu Asp
                165                 170                 175

Tyr Asn Ser Thr Leu Arg Val Val Ser Ala Leu Pro Ile Gln His Gln
            180                 185                 190

Asp Trp Met Ser Gly Lys Glu Phe Lys Cys Lys Val Asn Asn Lys Asp
        195                 200                 205

Leu Pro Ala Pro Ile Glu Arg Thr Ile Ser Lys Pro Lys Gly Ser Val
    210                 215                 220

Arg Ala Pro Gln Val Tyr Val Leu Pro Pro Pro Glu Glu Glu Met Thr
225                 230                 235                 240

Lys Lys Gln Val Thr Leu Thr Cys Met Val Thr Asp Phe Met Pro Glu
                245                 250                 255

Asp Ile Tyr Val Glu Trp Thr Asn Asn Gly Lys Thr Glu Leu Asn Tyr
            260                 265                 270

Lys Asn Thr Glu Pro Val Leu Asp Ser Asp Gly Ser Tyr Phe Met Tyr
        275                 280                 285

Ser Lys Leu Arg Val Glu Lys Lys Asn Trp Val Glu Arg Asn Ser Tyr
    290                 295                 300

Ser Cys Ser Val Val His Glu Gly Leu His Asn His His Thr Thr Lys
305                 310                 315                 320

Ser Phe Ser Arg Thr Pro Gly Lys
                325
```

<210> SEQ ID NO 38
<211> LENGTH: 107
<212> TYPE: PRT
<213> ORGANISM: Mus musculus

<400> SEQUENCE: 38

```
Arg Thr Val Ala Ala Pro Thr Val Ser Ile Phe Pro Pro Ser Ser Glu
1               5                   10                  15
```

```
Gln Leu Thr Ser Gly Gly Ala Ser Val Val Cys Phe Leu Asn Asn Phe
             20                  25                  30

Tyr Pro Lys Asp Ile Asn Val Lys Trp Lys Ile Asp Gly Ser Glu Arg
         35                  40                  45

Gln Asn Gly Val Leu Asn Ser Trp Thr Asp Gln Asp Ser Lys Asp Ser
     50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 39
<211> LENGTH: 330
<212> TYPE: PRT
<213> ORGANISM: Homo sapiens

<400> SEQUENCE: 39

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 40
<211> LENGTH: 107
<212> TYPE: PRT
<213> ORGANISM: Homo sapiens

<400> SEQUENCE: 40

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 41
<211> LENGTH: 326
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 42
<211> LENGTH: 377
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
```

```
            210                 215                 220
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
                355                 360                 365

Lys Ser Leu Ser Leu Ser Pro Gly Lys
            370                 375

<210> SEQ ID NO 43
<211> LENGTH: 327
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 44
<211> LENGTH: 245
<212> TYPE: PRT
<213> ORGANISM: Artificial Sequence
<220> FEATURE:
<223> OTHER INFORMATION: Hybrid Fc_Heavy region

<400> SEQUENCE: 44

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
                20                  25                  30

Thr Gln Pro Leu Gly Val Phe Leu Phe Pro Pro Lys Pro Lys Asp Thr
            35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
    115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
    195                 200                 205

Thr Val Asp Lys Ser Arg Trp Gln Glu Gly Asn Val Phe Ser Cys Ser
210                 215                 220

Val Met His Glu Ala Leu His Asn His Tyr Thr Gln Lys Ser Leu Ser
225                 230                 235                 240
```

Leu Ser Leu Gly Lys
            245

<210> SEQ ID NO 45
<211> LENGTH: 475
<212> TYPE: PRT
<213> ORGANISM: Artificial Sequence
<220> FEATURE:
<223> OTHER INFORMATION: A8 heavy chain_mouse IgG2 Fc_full sequence

<400> SEQUENCE: 45

Met Glu Thr Asp Thr Leu Leu Trp Val Leu Leu Trp Val Pro
1               5                   10                  15

Gly Ser Thr Trp Glu Val Gln Leu Leu Glu Ser Gly Gly Leu Val
            20                  25                  30

Gln Pro Gly Gly Ser Leu Arg Leu Ser Cys Ala Ala Ser Gly Phe Thr
        35                  40                  45

Phe Ser Asp Tyr Asp Met Ser Trp Val Arg Gln Val Pro Gly Lys Gly
    50                  55                  60

Leu Glu Trp Val Ser Trp Ile Ser His Gly Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Gly Leu Gly Leu Cys Lys Thr Gly Leu Cys
        115                 120                 125

Tyr Tyr Tyr Asp Ala Met Asp Val Trp Gly Gln Gly Thr Leu Val Thr
    130                 135                 140

Val Ser Ser Thr Thr Ala Pro Ser Val Tyr Pro Leu Ala Pro Val Cys
145                 150                 155                 160

Gly Asp Thr Thr Gly Ser Ser Val Thr Leu Gly Cys Leu Val Lys Gly
                165                 170                 175

Tyr Phe Pro Glu Pro Val Thr Leu Thr Trp Asn Ser Gly Ser Leu Ser
            180                 185                 190

Ser Gly Val His Thr Phe Pro Ala Val Leu Gln Ser Asp Leu Tyr Thr
        195                 200                 205

Leu Ser Ser Ser Val Thr Val Thr Ser Ser Thr Trp Pro Ser Gln Ser
    210                 215                 220

Ile Thr Cys Asn Val Ala His Pro Ala Ser Ser Thr Lys Val Asp Lys
225                 230                 235                 240

Lys Ile Glu Pro Arg Gly Pro Thr Ile Lys Pro Cys Pro Pro Cys Lys
                245                 250                 255

Cys Pro Ala Pro Asn Leu Leu Gly Gly Pro Ser Val Phe Ile Phe Pro
            260                 265                 270

Pro Lys Ile Lys Asp Val Leu Met Ile Ser Leu Ser Pro Ile Val Thr
        275                 280                 285

Cys Val Val Val Asp Val Ser Glu Asp Asp Pro Asp Val Gln Ile Ser
    290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
                325                 330                 335

Gln His Gln Asp Trp Met Ser Gly Lys Glu Phe Lys Cys Lys Val Asn
            340                 345                 350

```
Asn Lys Asp Leu Pro Ala Pro Ile Glu Arg Thr Ile Ser Lys Pro Lys
            355                 360                 365

Gly Ser Val Arg Ala Pro Gln Val Tyr Val Leu Pro Pro Glu Glu
370                 375                 380

Glu Met Thr Lys Gln Val Thr Leu Thr Cys Met Val Thr Asp Phe
385                 390                 395                 400

Met Pro Glu Asp Ile Tyr Val Glu Trp Thr Asn Asn Gly Lys Thr Glu
                405                 410                 415

Leu Asn Tyr Lys Asn Thr Glu Pro Val Leu Asp Ser Asp Gly Ser Tyr
            420                 425                 430

Phe Met Tyr Ser Lys Leu Arg Val Glu Lys Lys Asn Trp Val Glu Arg
        435                 440                 445

Asn Ser Tyr Ser Cys Ser Val Val His Glu Gly Leu His Asn His His
    450                 455                 460

Thr Thr Lys Ser Phe Ser Arg Thr Pro Gly Lys
465                 470                 475

<210> SEQ ID NO 46
<211> LENGTH: 237
<212> TYPE: PRT
<213> ORGANISM: Artificial Sequence
<220> FEATURE:
<223> OTHER INFORMATION: A8 light chain_mouse IgG2 Fc_full sequence

<400> SEQUENCE: 46

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Thr Gly Ser Ser Ser Asn
        35                  40                  45

Ile Gly Asn Asn Ser Val Thr Trp Tyr Gln Gln Leu Pro Gly Thr Ala
    50                  55                  60

Pro Lys Leu Leu Ile Tyr Ala Asp Asn Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Ser Ser Leu Ser Ala Tyr Val Phe Gly Gly Gly Thr Lys Leu Thr
        115                 120                 125

Val Leu Arg Thr Val Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
210                 215                 220

Thr Ser Pro Ile Val Lys Ser Phe Asn Arg Asn Glu Cys
225                 230                 235
```

```
<210> SEQ ID NO 47
<211> LENGTH: 464
<212> TYPE: PRT
<213> ORGANISM: Artificial Sequence
<220> FEATURE:
<223> OTHER INFORMATION: B8 heavy chain_mouse IgG2 Fc_full sequence

<400> SEQUENCE: 47

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asp Tyr Tyr Met Ser Trp Val Arg Gln Ala Pro Gly Lys Gly
    50                  55                  60

Leu Glu Trp Val Ser Gly Ile Ser His Asp Gly Ser Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg His Trp Thr Thr Phe Asp Tyr Trp Gly Gln
        115                 120                 125

Gly Thr Leu Val Thr Val Ser Ser Thr Thr Ala Pro Ser Val Tyr Pro
    130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
        195                 200                 205

Trp Pro Ser Gln Ser Ile Thr Cys Asn Val Ala His Pro Ala Ser Ser
    210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Leu Leu Gly Gly Pro Ser
                245                 250                 255

Val Phe Ile Phe Pro Pro Lys Ile Lys Asp Val Leu Met Ile Ser Leu
            260                 265                 270

Ser Pro Ile Val Thr Cys Val Val Val Asp Val Ser Glu Asp Asp Pro
        275                 280                 285

Asp Val Gln Ile Ser Trp Phe Val Asn Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Pro Ala Pro Ile Glu Arg Thr
            340                 345                 350

Ile Ser Lys Pro Lys Gly Ser Val Arg Ala Pro Gln Val Tyr Val Leu
        355                 360                 365
```

```
Pro Pro Pro Glu Glu Glu Met Thr Lys Lys Gln Val Thr Leu Thr Cys
    370                 375                 380
Met Val Thr Asp Phe Met Pro Glu Asp Ile Tyr Val Glu Trp Thr Asn
385                 390                 395                 400
Asn Gly Lys Thr Glu Leu Asn Tyr Lys Asn Thr Glu Pro Val Leu Asp
                405                 410                 415
Ser Asp Gly Ser Tyr Phe Met Tyr Ser Lys Leu Arg Val Glu Lys Lys
            420                 425                 430
Asn Trp Val Glu Arg Asn Ser Tyr Ser Cys Ser Val Val His Glu Gly
        435                 440                 445
Leu His Asn His His Thr Thr Lys Ser Phe Ser Arg Thr Pro Gly Lys
    450                 455                 460
```

<210> SEQ ID NO 48
<211> LENGTH: 237
<212> TYPE: PRT
<213> ORGANISM: Artificial Sequence
<220> FEATURE:
<223> OTHER INFORMATION: B8 light chain_mouse IgG2 Fc_full sequence

<400> SEQUENCE: 48

```
Met Glu Thr Asp Thr Leu Leu Leu Trp Val Leu Leu Leu Trp Val Pro
1               5                   10                  15
Gly Ser Thr Trp Gln Ser Val Leu Thr Gln Pro Pro Ser Ala Ser Gly
            20                  25                  30
Thr Pro Gly Gln Arg Val Thr Ile Ser Cys Ser Gly Ser Ser Ser Asn
        35                  40                  45
Ile Gly Ser Asn Asn Val Thr Trp Tyr Gln Gln Leu Pro Gly Thr Ala
    50                  55                  60
Pro Lys Leu Leu Ile Tyr Ala Asn Ser Asn Arg Pro Ser Gly Val Pro
65                  70                  75                  80
Asp Arg Phe Ser Gly Ser Lys Ser Gly Thr Ser Ala Ser Leu Ala Ile
                85                  90                  95
Ser Gly Leu Arg Ser Glu Asp Glu Ala Asp Tyr Tyr Cys Gly Ala Trp
            100                 105                 110
Asp Tyr Ser Leu Ser Ala Tyr Val Phe Gly Gly Gly Thr Lys Leu Thr
        115                 120                 125
Val Leu Arg Thr Val Ala Ala Pro Thr Val Ser Ile Phe Pro Pro Ser
    130                 135                 140
Ser Glu Gln Leu Thr Ser Gly Gly Ala Ser Val Val Cys Phe Leu Asn
145                 150                 155                 160
Asn Phe Tyr Pro Lys Asp Ile Asn Val Lys Trp Lys Ile Asp Gly Ser
                165                 170                 175
Glu Arg Gln Asn Gly Val Leu Asn Ser Trp Thr Asp Gln Asp Ser Lys
            180                 185                 190
Asp Ser Thr Tyr Ser Met Ser Ser Thr Leu Thr Leu Thr Lys Asp Glu
        195                 200                 205
Tyr Glu Arg His Asn Ser Tyr Thr Cys Glu Ala Thr His Lys Thr Ser
    210                 215                 220
Thr Ser Pro Ile Val Lys Ser Phe Asn Arg Asn Glu Cys
225                 230                 235
```

<210> SEQ ID NO 49
<211> LENGTH: 475
<212> TYPE: PRT
<213> ORGANISM: Artificial Sequence
<220> FEATURE:

<223> OTHER INFORMATION: D9 heavy chain_mouse IgG2 Fc_full sequence

<400> SEQUENCE: 49

```
Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Ala Met Ser Trp Val Arg Gln Ala Pro Gly Lys Gly
50                  55                  60

Leu Glu Trp Val Ser Ala Ile Tyr Pro Gly Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Ile Leu Pro Cys Pro Trp Gly Arg Cys
        115                 120                 125

Tyr Tyr Asp Tyr Ala Met Asp Val Trp Gly Gln Gly Thr Leu Val Thr
130                 135                 140

Val Ser Ser Thr Thr Ala Pro Ser Val Tyr Pro Leu Ala Pro Val Cys
145                 150                 155                 160

Gly Asp Thr Thr Gly Ser Ser Val Thr Leu Gly Cys Leu Val Lys Gly
                165                 170                 175

Tyr Phe Pro Glu Pro Val Thr Leu Thr Trp Asn Ser Gly Ser Leu Ser
            180                 185                 190

Ser Gly Val His Thr Phe Pro Ala Val Leu Gln Ser Asp Leu Tyr Thr
        195                 200                 205

Leu Ser Ser Ser Val Thr Val Thr Ser Ser Thr Trp Pro Ser Gln Ser
210                 215                 220

Ile Thr Cys Asn Val Ala His Pro Ala Ser Ser Thr Lys Val Asp Lys
225                 230                 235                 240

Lys Ile Glu Pro Arg Gly Pro Thr Ile Lys Pro Cys Pro Pro Cys Lys
                245                 250                 255

Cys Pro Ala Pro Asn Leu Leu Gly Gly Pro Ser Val Phe Ile Phe Pro
            260                 265                 270

Pro Lys Ile Lys Asp Val Leu Met Ile Ser Leu Ser Pro Ile Val Thr
        275                 280                 285

Cys Val Val Val Asp Val Ser Glu Asp Asp Pro Asp Val Gln Ile Ser
290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ala Pro Ile Glu Arg Thr Ile Ser Lys Pro Lys
        355                 360                 365

Gly Ser Val Arg Ala Pro Gln Val Tyr Val Leu Pro Pro Pro Glu Glu
370                 375                 380

Glu Met Thr Lys Lys Gln Val Thr Leu Thr Cys Met Val Thr Asp Phe
385                 390                 395                 400
```

```
Met Pro Glu Asp Ile Tyr Val Glu Trp Thr Asn Asn Gly Lys Thr Glu
                405                 410                 415

Leu Asn Tyr Lys Asn Thr Glu Pro Val Leu Asp Ser Asp Gly Ser Tyr
            420                 425                 430

Phe Met Tyr Ser Lys Leu Arg Val Glu Lys Lys Asn Trp Val Glu Arg
        435                 440                 445

Asn Ser Tyr Ser Cys Ser Val Val His Glu Gly Leu His Asn His His
    450                 455                 460

Thr Thr Lys Ser Phe Ser Arg Thr Pro Gly Lys
465                 470                 475

<210> SEQ ID NO 50
<211> LENGTH: 237
<212> TYPE: PRT
<213> ORGANISM: Artificial Sequence
<220> FEATURE:
<223> OTHER INFORMATION: D9 light chain_mouse IgG2 Fc_full sequence

<400> SEQUENCE: 50

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Asp Ser Ser Ser Asn
        35                  40                  45

Ile Gly Ser Asn Thr Val Ser Trp Tyr Gln Gln Leu Pro Gly Thr Ala
    50                  55                  60

Pro Lys Leu Leu Ile Tyr Ala Asp Asn Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
            100                 105                 110

Asp Tyr Ser Leu Ser Gly Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 51
<211> LENGTH: 475
<212> TYPE: PRT
<213> ORGANISM: Artificial Sequence
<220> FEATURE:
<223> OTHER INFORMATION: H6 heavy chain_mouse IgG2 Fc_full sequence

<400> SEQUENCE: 51
```

-continued

```
Met Glu Thr Asp Thr Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
            35                  40                  45

Phe Ser Asn Tyr Ala Met Ser Trp Val Arg Gln Ala Pro Gly Lys Gly
        50                  55                  60

Leu Glu Trp Val Ser Val Ile Ser His Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Val Ile Ser Asn Cys His Leu Gly Val Cys
        115                 120                 125

Tyr Tyr Ser Asn Gly Met Asp Val Trp Gly Gln Gly Thr Leu Val Thr
    130                 135                 140

Val Ser Ser Thr Thr Ala Pro Ser Val Tyr Pro Leu Ala Pro Val Cys
145                 150                 155                 160

Gly Asp Thr Thr Gly Ser Ser Val Thr Leu Gly Cys Leu Val Lys Gly
                165                 170                 175

Tyr Phe Pro Glu Pro Val Thr Leu Thr Trp Asn Ser Gly Ser Leu Ser
            180                 185                 190

Ser Gly Val His Thr Phe Pro Ala Val Leu Gln Ser Asp Leu Tyr Thr
        195                 200                 205

Leu Ser Ser Ser Val Thr Val Thr Ser Ser Thr Trp Pro Ser Gln Ser
    210                 215                 220

Ile Thr Cys Asn Val Ala His Pro Ala Ser Ser Thr Lys Val Asp Lys
225                 230                 235                 240

Lys Ile Glu Pro Arg Gly Pro Thr Ile Lys Pro Cys Pro Pro Cys Lys
                245                 250                 255

Cys Pro Ala Pro Asn Leu Leu Gly Gly Pro Ser Val Phe Ile Phe Pro
            260                 265                 270

Pro Lys Ile Lys Asp Val Leu Met Ile Ser Leu Ser Pro Ile Val Thr
        275                 280                 285

Cys Val Val Asp Val Ser Glu Asp Asp Pro Asp Val Gln Ile Ser
    290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ala Pro Ile Glu Arg Thr Ile Ser Lys Pro Lys
        355                 360                 365

Gly Ser Val Arg Ala Pro Gln Val Tyr Val Leu Pro Pro Pro Glu Glu
    370                 375                 380

Glu Met Thr Lys Lys Gln Val Thr Leu Thr Cys Met Val Thr Asp Phe
385                 390                 395                 400

Met Pro Glu Asp Ile Tyr Val Glu Trp Thr Asn Asn Gly Lys Thr Glu
                405                 410                 415
```

```
Leu Asn Tyr Lys Asn Thr Glu Pro Val Leu Asp Ser Asp Gly Ser Tyr
                420                 425                 430

Phe Met Tyr Ser Lys Leu Arg Val Glu Lys Lys Asn Trp Val Glu Arg
                435                 440                 445

Asn Ser Tyr Ser Cys Ser Val Val His Glu Gly Leu His Asn His His
                450                 455                 460

Thr Thr Lys Ser Phe Ser Arg Thr Pro Gly Lys
465                 470                 475

<210> SEQ ID NO 52
<211> LENGTH: 237
<212> TYPE: PRT
<213> ORGANISM: Artificial Sequence
<220> FEATURE:
<223> OTHER INFORMATION: H6 light chain_mouse IgG2 Fc_full sequence

<400> SEQUENCE: 52

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Ser Gly Ser Ser Ser Asn
            35                  40                  45

Ile Gly Asn Asn Asp Val Tyr Trp Tyr Gln Gln Leu Pro Gly Thr Ala
        50                  55                  60

Pro Lys Leu Leu Ile Tyr Ser Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
                100                 105                 110

Asp Tyr Ser Leu Ser Gly Tyr Val Phe Gly Gly Gly Thr Lys Leu Thr
            115                 120                 125

Val Leu Arg Thr Val Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 53
<211> LENGTH: 469
<212> TYPE: PRT
<213> ORGANISM: Artificial Sequence
<220> FEATURE:
<223> OTHER INFORMATION: A7 heavy chain

<400> SEQUENCE: 53

Met Glu Thr Asp Thr Leu Leu Leu Trp Val Leu Leu Leu Trp Val Pro
1               5                   10                  15
```

-continued

```
Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Gly Tyr Asp Met Ser Trp Val Arg Gln Ala Pro Gly Lys Gly
 50                  55                  60

Leu Glu Trp Val Ser Leu Ile Tyr Pro Asp Ser Gly Asn Lys Tyr Tyr
65                   70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Asp Ala Gly Leu Ser Trp Ala Gly Ala Phe
        115                 120                 125

Asp Tyr Trp Gly Gln Gly Thr Leu Val Thr Val Ser Ser Thr Thr Ala
130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Glu Met Thr Lys Lys Gln
370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430
```

```
Arg Val Glu Lys Lys Asn Trp Val Glu Arg Asn Ser Tyr Ser Cys Ser
            435                 440                 445

Val Val His Glu Gly Leu His Asn His His Thr Thr Lys Ser Phe Ser
    450                 455                 460

Arg Thr Pro Gly Lys
465

<210> SEQ ID NO 54
<211> LENGTH: 237
<212> TYPE: PRT
<213> ORGANISM: Artificial Sequence
<220> FEATURE:
<223> OTHER INFORMATION: A7 light chain

<400> SEQUENCE: 54

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Asn Tyr Val Thr Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Gln Ser Glu Asp Glu Ala Asp Tyr Tyr Cys Gly Ser Trp
            100                 105                 110

Asp Tyr Ser Leu Ser Ala Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 55
<211> LENGTH: 469
<212> TYPE: PRT
<213> ORGANISM: Artificial Sequence
<220> FEATURE:
<223> OTHER INFORMATION: C8 heavy chain

<400> SEQUENCE: 55

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30
```

-continued

Gln Pro Gly Gly Ser Leu Arg Leu Ser Cys Ala Ala Ser Gly Phe Thr
        35                  40                  45

Phe Ser Asn Tyr Tyr Met Ser Trp Val Arg Gln Ala Pro Gly Lys Gly
 50                  55                  60

Leu Glu Trp Val Ser Gly Ile Ser Pro Gly Asp Ser Ser Thr Tyr Tyr
 65                  70                  75                  80

Ala Asp Ser Val Lys Gly Arg Phe Thr Ile Ser Arg Asp Asn Ser Lys
                 85                  90                  95

Asn Thr Leu Tyr Leu Gln Met Asn Ser Leu Arg Ala Glu Asp Thr Ala
            100                 105                 110

Val Tyr Tyr Cys Ala Lys Gly Leu Tyr Ser Asn Pro Asn Glu Pro Phe
            115                 120                 125

Asp Tyr Trp Gly Gln Gly Thr Leu Val Thr Val Ser Ser Thr Thr Ala
        130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
        290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Pro Glu Glu Glu Met Thr Lys Lys Gln
370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
            450                 455                 460

Arg Thr Pro Gly Lys
465

<210> SEQ ID NO 56
<211> LENGTH: 237
<212> TYPE: PRT
<213> ORGANISM: Artificial Sequence
<220> FEATURE:
<223> OTHER INFORMATION: C8 light chain

<400> SEQUENCE: 56

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Thr Gly Ser Ser Ser Asn
        35                  40                  45

Ile Gly Ser Asn Tyr Val Ser Trp Tyr Gln Gln Leu Pro Gly Thr Ala
    50                  55                  60

Pro Lys Leu Leu Ile Tyr Asp Asp Ser Gln Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Thr Trp
            100                 105                 110

Asp Tyr Ser Leu Asn Gly Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 57
<211> LENGTH: 475
<212> TYPE: PRT
<213> ORGANISM: Artificial Sequence
<220> FEATURE:
<223> OTHER INFORMATION: E7 heavy chain

<400> SEQUENCE: 57

Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

```
Phe Ser Ser Tyr Asp Met Ser Trp Val Arg Gln Ala Pro Gly Lys Gly
        50                  55                  60

Leu Glu Trp Val Ser Gly Ile Ser Pro Asp Gly Ser Asn Ile Tyr Tyr
 65                  70                  75                  80

Ala Asp Ser Val Lys Gly Arg Phe Thr Ile Ser Arg Asp Asn Ser Lys
                 85                  90                  95

Asn Thr Leu Tyr Leu Gln Met Asn Ser Leu Arg Ala Glu Asp Thr Ala
            100                 105                 110

Val Tyr Tyr Cys Ala Lys Val Gly Leu Arg Cys Arg Tyr Glu Ala Cys
        115                 120                 125

Ser Tyr Ala Tyr Gly Met Asp Val Trp Gly Gln Gly Thr Leu Val Thr
130                 135                 140

Val Ser Ser Thr Thr Ala Pro Ser Val Tyr Pro Leu Ala Pro Val Cys
145                 150                 155                 160

Gly Asp Thr Thr Gly Ser Ser Val Thr Leu Gly Cys Leu Val Lys Gly
                165                 170                 175

Tyr Phe Pro Glu Pro Val Thr Leu Thr Trp Asn Ser Gly Ser Leu Ser
            180                 185                 190

Ser Gly Val His Thr Phe Pro Ala Val Leu Gln Ser Asp Leu Tyr Thr
        195                 200                 205

Leu Ser Ser Ser Val Thr Val Thr Ser Thr Trp Pro Ser Gln Ser
210                 215                 220

Ile Thr Cys Asn Val Ala His Pro Ala Ser Ser Thr Lys Val Asp Lys
225                 230                 235                 240

Lys Ile Glu Pro Arg Gly Pro Thr Ile Lys Pro Cys Pro Pro Cys Lys
                245                 250                 255

Cys Pro Ala Pro Asn Leu Leu Gly Gly Pro Ser Val Phe Ile Phe Pro
            260                 265                 270

Pro Lys Ile Lys Asp Val Leu Met Ile Ser Leu Ser Pro Ile Val Thr
        275                 280                 285

Cys Val Val Val Asp Val Ser Glu Asp Asp Pro Asp Val Gln Ile Ser
290                 295                 300

Trp Phe Val Asn Asn Val Glu Val His Thr Ala Gln Thr Gln Thr His
305                 310                 315                 320

Arg Glu Asp Tyr Asn Ser Thr Leu Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ala Pro Ile Glu Arg Thr Ile Ser Lys Pro Lys
        355                 360                 365

Gly Ser Val Arg Ala Pro Gln Val Tyr Val Leu Pro Pro Glu Glu
370                 375                 380

Glu Met Thr Lys Lys Gln Val Thr Leu Thr Cys Met Val Thr Asp Phe
385                 390                 395                 400

Met Pro Glu Asp Ile Tyr Val Glu Trp Thr Asn Asn Gly Lys Thr Glu
                405                 410                 415

Leu Asn Tyr Lys Asn Thr Glu Pro Val Leu Asp Ser Asp Gly Ser Tyr
            420                 425                 430

Phe Met Tyr Ser Lys Leu Arg Val Glu Lys Lys Asn Trp Val Glu Arg
        435                 440                 445

Asn Ser Tyr Ser Cys Ser Val Val His Glu Gly Leu His Asn His His
450                 455                 460
```

```
Thr Thr Lys Ser Phe Ser Arg Thr Pro Gly Lys
465                 470                 475
```

<210> SEQ ID NO 58
<211> LENGTH: 237
<212> TYPE: PRT
<213> ORGANISM: Artificial Sequence
<220> FEATURE:
<223> OTHER INFORMATION: E7 light chain

<400> SEQUENCE: 58

```
Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
                20                  25                  30

Thr Pro Gly Gln Arg Val Thr Ile Ser Cys Ser Gly Ser Ser Ser Asn
            35                  40                  45

Ile Gly Ser Asn Tyr Val Ser Trp Tyr Gln Gln Leu Pro Gly Thr Ala
50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Thr Trp
            100                 105                 110

Asp Ser Ser Leu Asn Gly Tyr Val Phe Gly Gly Gly Thr Lys Leu Thr
        115                 120                 125

Val Leu Arg Thr Val Ala Ala Pro Thr Val Ser Ile Phe Pro Pro Ser
130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
210                 215                 220

Thr Ser Pro Ile Val Lys Ser Phe Asn Arg Asn Glu Cys
225                 230                 235
```

<210> SEQ ID NO 59
<211> LENGTH: 469
<212> TYPE: PRT
<213> ORGANISM: Artificial Sequence
<220> FEATURE:
<223> OTHER INFORMATION: G3 heavy chain

<400> SEQUENCE: 59

```
Met Glu Thr Asp Thr Leu Leu Leu Trp Val Leu Leu Leu Trp Val Pro
1               5                   10                  15

Gly Ser Thr Trp Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asn Tyr Asp Met Ser Trp Val Arg Gln Ala Pro Gly Lys Gly
50                  55                  60
```

-continued

```
Leu Glu Trp Val Ser Ser Ile Ser Pro Ser Ser Gly Ser Ile Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Asp Leu Asp Ala Phe Trp Arg Pro Ser Phe
        115                 120                 125

Asp Tyr Trp Gly Gln Gly Thr Leu Val Thr Val Ser Ser Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
            260                 265                 270

Leu Met Ile Ser Leu Ser Pro Ile Val Thr Cys Val Val Val Asp Val
        275                 280                 285

Ser Glu Asp Asp Pro Asp Val Gln Ile Ser Trp Phe Val Asn Asn Val
    290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
            340                 345                 350

Pro Ile Glu Arg Thr Ile Ser Lys Pro Lys Gly Ser Val Arg Ala Pro
        355                 360                 365

Gln Val Tyr Val Leu Pro Pro Glu Glu Glu Met Thr Lys Lys Gln
    370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
            420                 425                 430

Arg Val Glu Lys Lys Asn Trp Val Glu Arg Asn Ser Tyr Ser Cys Ser
        435                 440                 445

Val Val His Glu Gly Leu His Asn His His Thr Thr Lys Ser Phe Ser
    450                 455                 460

Arg Thr Pro Gly Lys
465
```

-continued

```
<210> SEQ ID NO 60
<211> LENGTH: 237
<212> TYPE: PRT
<213> ORGANISM: Artificial Sequence
<220> FEATURE:
<223> OTHER INFORMATION: G3 light chain

<400> SEQUENCE: 60

Met Glu Thr Asp Thr Leu Leu Leu Trp Val Leu Leu Leu Trp Val Pro
1               5                   10                  15

Gly Ser Thr Trp Gln Ser Val Leu Thr Gln Pro Pro Ser Ala Ser Gly
            20                  25                  30

Thr Pro Gly Gln Arg Val Thr Ile Ser Cys Thr Gly Ser Ser Ser Asn
        35                  40                  45

Ile Gly Asn Asn Val Asn Trp Tyr Gln Gln Leu Pro Gly Thr Ala
    50                  55                  60

Pro Lys Leu Leu Ile Tyr Ser Asp Ser His Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Gly Ser Trp
            100                 105                 110

Asp Asp Ser Leu Ser Ala Tyr Val Phe Gly Gly Gly Thr Lys Leu Thr
        115                 120                 125

Val Leu Arg Thr Val Ala Ala Pro Thr Val Ser Ile Phe Pro Pro Ser
    130                 135                 140

Ser Glu Gln Leu Thr Ser Gly Gly Ala Ser Val Val Cys Phe Leu Asn
145                 150                 155                 160

Asn Phe Tyr Pro Lys Asp Ile Asn Val Lys Trp Lys Ile Asp Gly Ser
                165                 170                 175

Glu Arg Gln Asn Gly Val Leu Asn Ser Trp Thr Asp Gln Asp Ser Lys
            180                 185                 190

Asp Ser Thr Tyr Ser Met Ser Ser Thr Leu Thr Leu Thr Lys Asp Glu
        195                 200                 205

Tyr Glu Arg His Asn Ser Tyr Thr Cys Glu Ala Thr His Lys Thr Ser
    210                 215                 220

Thr Ser Pro Ile Val Lys Ser Phe Asn Arg Asn Glu Cys
225                 230                 235

<210> SEQ ID NO 61
<211> LENGTH: 24
<212> TYPE: DNA
<213> ORGANISM: Artificial Sequence
<220> FEATURE:
<223> OTHER INFORMATION: Mouse Lrig-1 forward primer

<400> SEQUENCE: 61
gacggaattc agtgaggaga acct                                      24

<210> SEQ ID NO 62
<211> LENGTH: 24
<212> TYPE: DNA
<213> ORGANISM: Artificial Sequence
<220> FEATURE:
<223> OTHER INFORMATION: Mouse Lrig-1 reverse primer

<400> SEQUENCE: 62
caactggtag tggcagcttg tagg                                      24
```

<210> SEQ ID NO 63
<211> LENGTH: 24
<212> TYPE: DNA
<213> ORGANISM: Artificial Sequence
<220> FEATURE:
<223> OTHER INFORMATION: Mouse Lrig-2 forward primer

<400> SEQUENCE: 63
tcacaaggaa cattgtctga acca                                          24

<210> SEQ ID NO 64
<211> LENGTH: 24
<212> TYPE: DNA
<213> ORGANISM: Artificial Sequence
<220> FEATURE:
<223> OTHER INFORMATION: Mouse Lrig-2 reverse primer

<400> SEQUENCE: 64
gcctgatcta acacatcctc ctca                                          24

<210> SEQ ID NO 65
<211> LENGTH: 24
<212> TYPE: DNA
<213> ORGANISM: Artificial Sequence
<220> FEATURE:
<223> OTHER INFORMATION: Mouse Lrig-3 forward primer

<400> SEQUENCE: 65
cagcaccttg agctgaacag aaac                                          24

<210> SEQ ID NO 66
<211> LENGTH: 24
<212> TYPE: DNA
<213> ORGANISM: Artificial Sequence
<220> FEATURE:
<223> OTHER INFORMATION: Mouse Lrig-3 reverse primer

<400> SEQUENCE: 66
ccagcctttg gtaatctcgg ttag                                          24

<210> SEQ ID NO 67
<211> LENGTH: 24
<212> TYPE: DNA
<213> ORGANISM: Artificial Sequence
<220> FEATURE:
<223> OTHER INFORMATION: Mouse FOXP3 forward primer

<400> SEQUENCE: 67
ctttcaccta tcccacccTt atcc                                          24

<210> SEQ ID NO 68
<211> LENGTH: 24
<212> TYPE: DNA
<213> ORGANISM: Artificial Sequence
<220> FEATURE:
<223> OTHER INFORMATION: Mouse FOXP3 reverse primer

<400> SEQUENCE: 68
attcatctac ggtccacact gctc                                          24

<210> SEQ ID NO 69
<211> LENGTH: 20
<212> TYPE: DNA
<213> ORGANISM: Artificial Sequence
<220> FEATURE:
<223> OTHER INFORMATION: ACTG1 forward primer

```
<400> SEQUENCE: 69
ggcgtcatgg tgggcatggg                                                    20

<210> SEQ ID NO 70
<211> LENGTH: 20
<212> TYPE: DNA
<213> ORGANISM: Artificial Sequence
<220> FEATURE:
<223> OTHER INFORMATION: ACTG1 reverse primer

<400> SEQUENCE: 70
atggcgtggg gaagggcgta                                                    20
```

The invention claimed is:

1. A binding molecule which specifically binds to Lrig-1 (leucine-rich and immunoglobulin-like domains 1) protein, wherein the binding molecule is selected from the group consisting of the following (1) to (4):
   (1) a binding molecule comprising a heavy chain variable region that contains a heavy chain CDR1 represented by SEQ ID NO: 5, a heavy chain CDR2 represented by SEQ ID NO: 6, and a heavy chain CDR3 represented by SEQ ID NO: 7; and a light chain variable region that contains a light chain CDR1 represented by SEQ ID NO: 8, a light chain CDR2 represented by SEQ ID NO: 9, and a light chain CDR3 represented by SEQ ID NO: 10;
   (2) a binding molecule comprising a heavy chain variable region that contains a heavy chain CDR1 represented by SEQ ID NO: 13, a heavy chain CDR2 represented by SEQ ID NO: 14, and a heavy chain CDR3 represented by SEQ ID NO: 15; and a light chain variable region that contains a light chain CDR1 represented by SEQ ID NO: 16, a light chain CDR2 represented by SEQ ID NO: 17, and a light chain CDR3 represented by SEQ ID NO: 18;
   (3) a binding molecule comprising a heavy chain variable region that contains a heavy chain CDR1 represented by SEQ ID NO: 21, a heavy chain CDR2 represented by SEQ ID NO: 22, and a heavy chain CDR3 represented by SEQ ID NO: 23; and a light chain variable region that contains a light chain CDR1 represented by SEQ ID NO: 24, a light chain CDR2 represented by SEQ ID NO: 25, and a light chain CDR3 represented by SEQ ID NO: 26;
   (4) a binding molecule comprising a heavy chain variable region that contains a heavy chain CDR1 represented by SEQ ID NO: 29, a heavy chain CDR2 represented by SEQ ID NO: 30, and a heavy chain CDR3 represented by SEQ ID NO: 31; and a light chain variable region that contains a light chain CDR1 represented by SEQ ID NO: 32, a light chain CDR2 represented by SEQ ID NO: 33, and a light chain CDR3 represented by SEQ ID NO: 34.

2. The binding molecule according to claim 1, wherein the binding molecule is selected from the group consisting of the following binding molecules:
   a binding molecule comprising a heavy chain variable region represented by SEQ ID NO: 11, and a light chain variable region represented by SEQ ID NO: 12;
   a binding molecule comprising a heavy chain variable region represented by SEQ ID NO: 19, and a light chain variable region represented by SEQ ID NO: 20;
   a binding molecule comprising a heavy chain variable region represented by SEQ ID NO: 27, and a light chain variable region represented by SEQ ID NO: 28; and
   a binding molecule comprising a heavy chain variable region represented by SEQ ID NO: 35, and a light chain variable region represented by SEQ ID NO: 36.

3. The binding molecule according to claim 1, further comprising:
   an Fc region or a constant region.

4. The binding molecule according to claim 3, wherein the Fc region is an Fc region of an IgG1, IgG2, IgG3, or IgG4 antibody, or a hybrid Fc region.

5. The binding molecule according to claim 1, further comprising:
   a heavy chain constant region consisting of an amino acid sequence selected from the group consisting of SEQ ID NOs: 37, 39, 41, 42, 43, and 44.

6. The binding molecule according to claim 1, further comprising:
   a light chain constant region consisting of an amino acid sequence represented by SEQ ID NO: 38 or 40.

7. The binding molecule according to claim 1, further comprising:
   a heavy chain constant region consisting of an amino acid sequence represented by SEQ ID NO: 37; and
   a light chain constant region consisting of an amino acid sequence represented by SEQ ID NO: 38.

8. The binding molecule according to claim 1, further comprising:
   a heavy chain constant region consisting of an amino acid sequence represented by SEQ ID NO: 39, 41, 42, or 43; and
   a light chain constant region consisting of an amino acid sequence represented by SEQ ID NO: 40.

9. The binding molecule according to claim 1, further comprising:
   a heavy chain constant region consisting of an amino acid sequence represented by SEQ ID NO: 44.

10. The binding molecule according to claim 1, wherein the binding molecule is selected from the group consisting of the following binding molecules:
    a binding molecule comprising a heavy chain represented by SEQ ID NO: 45, and a light chain represented by SEQ ID NO: 46;
    a binding molecule comprising a heavy chain represented by SEQ ID NO: 47, and a light chain represented by SEQ ID NO: 48;
    a binding molecule comprising a heavy chain represented by SEQ ID NO: 49, and a light chain represented by SEQ ID NO: 50; and a binding molecule comprising a heavy chain represented by SEQ ID NO: 51, and a light chain represented by SEQ ID NO: 52.

11. The binding molecule according to claim 1, wherein the binding molecule is an antibody or a fragment thereof.

12. The binding molecule according to claim 11, wherein the antibody is a chimeric antibody, a humanized antibody, a bivalent antibody, a minibody, a domain antibody, an antibody mimetic, a diabody, a triabody, or a tetrabody, or a fragment thereof.

13. A pharmaceutical composition, comprising as an active ingredient:
the binding molecule according to claim 1.

14. A method of treating cancer, comprising administering a binding molecule according to claim 1 into a subject as an active ingredient,
wherein the cancer is solid tumor.

15. A method of treating cancer, comprising administering a binding molecule according to claim 1 into a subject as an active ingredient,
wherein the cancer is gastric cancer, liver cancer, gliocytoma, ovarian cancer, colorectal cancer, head and neck cancer, bladder cancer, renal cell cancer, breast cancer, prostate cancer, pancreatic cancer, melanoma, or lung cancer.

* * * * *